US000001427H

United States Statutory Invention Registration [19]

[11] Reg. Number: H1427

Briet et al.

[43] Published: Apr. 4, 1995

[54] SUBSTITUTED FLAVONOID COMPOUNDS, THEIR SALTS, THEIR MANUFACTURE AND THEIR USE IN COMBINATION WITH INTERLEUKIN-2

[76] Inventors: Phillipe Briet, 216 Avenue Felix Faure, 69003 Lyon; Jean-Jacques Berthelon, 35 Rue Dr. Bonhomme, 69008 Lyon; Francois Collonges, LoEnement Le Grand Champ, Chemin de Halage 01700 Beynost, all of France; Robert H. Wiltrout, 5664 Farmhouse Dr., Frederick, Md. 21701; Ronald L. Hornung, 13202 Nittany Ct., Union Bridge, Md. 21791

[21] Appl. No.: 892,706

[22] Filed: May 29, 1992

Related U.S. Application Data

[63] Continuation of Ser. No. 233,423, Aug. 18, 1988, abandoned, which is a continuation-in-part of Ser. No. 178,315, Apr. 6, 1988, abandoned.

[51] Int. Cl.[6] ..... A61K 45/05; A61K 31/35; C07D 311/04

[52] U.S. Cl. ..... 424/85.2; 514/454; 514/456; 549/403

[58] Field of Search ..... 424/85.2; 549/403; 514/454, 456, 458

[56] References Cited

U.S. PATENT DOCUMENTS

| | | | |
|---|---|---|---|
| 4,352,792 | 10/1982 | Ishitsuka et al. | 546/269 |
| 4,602,034 | 7/1986 | Briet et al. | 514/456 |
| 4,713,465 | 12/1987 | Krämer et al. | 549/403 |
| 4,841,077 | 6/1989 | Ito et al. | 549/403 |
| 4,938,956 | 7/1990 | Howard et al. | 514/2 |
| 5,096,707 | 3/1992 | Wiltrout et al. | 424/85.2 |
| 5,116,954 | 5/1992 | Briet et al. | 548/154 |
| 5,126,129 | 6/1992 | Wiltrout et al. | 514/456 |

FOREIGN PATENT DOCUMENTS

| | | | |
|---|---|---|---|
| 0278176 | 6/1988 | European Pat. Off. . | |
| 0283761 | 9/1988 | European Pat. Off. . | |
| 137818 | 6/1986 | Japan | 514/456 |
| 9008143 | 7/1990 | WIPO . | |

OTHER PUBLICATIONS

Chemical Abstracts 89:108951n (1978).
Chemical Abstracts 97:138315r (1982).
Chemical Abstracts 104:122574b (1985).
Chemical Abstracts 107:146923c (1987).
Futami et al., Cancer Research (Dec. 15, 1990) vol. 50, pp. 7926–7931.
*Robert H. Wiltrout et al.*, "Flavone-8-Acetic Acid Augments Systemic Natural Killer Cell Activity And Synergizes With IL-2 For Treatment Of Murine Renal Cancer" The Journal Of Immunology, vol. 140, pp. 3261–3265 No. 9, May 1, 1988.
*Baguley et al* "1301" is the abstract of a poster session presentation made May 27, 1988, between 3:00 and 6:00 P.M., at the A.A.C.R. meeting in . . . .

*Primary Examiner*—Shean Wu

[57] ABSTRACT

The use of substituted flavonoid compounds which have the immunomodulatory activity of (1) boosting natural killer activity in vivo and (2) inducing interferon, and (3) belong to the family of flavonoids of the formula (I):

in conjunction with interleukin-2 in cancer therapy is disclosed.

5 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SUBSTITUTED FLAVONOID COMPOUNDS, THEIR SALTS, THEIR MANUFACTURE AND THEIR USE IN COMBINATION WITH INTERLEUKIN-2

This application is a continuation of application Ser. No. 07/233,423, filed on Aug. 18, 1988, now abandoned, which is a continuation-in-part of Ser. No. 07/178,315, filed on Apr. 6, 1988, now abandoned.

BACKGROUND OF THE INVENTION

1. Field of the Invention

This invention relates to the use of interleukin-2 (IL-2) in antitumorous cancer therapy.

2. Discussion of the Background:

Attempts have been made recently to develop immunotherapies for the treatment of cancer by stimulating the host immune response to the tumor. These approaches are based on attempts to immunize against specific tumor cells or with nonspecific stimulants in the hope that general immune stimulation would concomitantly increase the host anti-tumor response.

Although some experimental evidence has indicated that this approach might be feasible in the therapy of established tumor, the inability to stimulate sufficiently strong responses to putative tumor antigens and the general immunoincompetence of the tumor bearing host argues against the success of this approach.

An alternative therapeutic approach to the immunologic treatment of cancer is that of the adoptive transfer of immune cells. Adoptive immunotherapy is defined as the transfer to the tumor-bearing host of active immunologic reagents, such as cells with antitumor reactivity that can mediate, either directly or indirectly, antitumor effects.

Adoptive immunotherapy represents an attractive approach to cancer therapy and to other conditions related to immune dysfunction. Because active immunologic reagents are transferred to the host, complete host immunocompetence is not required. Thus, the immunosuppression generally associated with a tumor-bearing state does not represent a major problem to this therapeutic alternative. Since host immunocompetence is not required, and in fact could be beneficial to the effects of the adoptive transfer of immune cells, adoptive immunotherapy can be easily combined with other therapies such as chemotherapy and radiation therapy.

Since the transfered reagents are immunologically specific, this treatment modality predicts a high degree of specificity and consequently of low morbidity. Further, in contrast to most other therapies, no immunosuppression is likely to result from this treatment. A review of previous attempts to perform adoptive immunotherapy of cancer in animals and humans can be found in Rosenberg et al, Adv. Cancer Res. 1977; 25:323–388.

Studies have indicated that recombinant interleukin-2 (rIL-2) has notable anti-tumor activity when used alone in tumor-bearing mice. See, for example, Greenberg et al, J. Exp. Med. (1985) 161:1122; North, J. Exp. Med. (1982) 155:1063; Mule et al., Science (1984) 225:1487, and Salup et al., J. Immunol. (1987) 138:641. Recent studies have also indicated that rIL-2 has notable anti-tumor activity in certain human cancer patients. See, for example, Rosenberg et al., N. Engl. J. Med. (1985) 313:1485 and Lotze et al., JAMA (1986) 256:3117. The therapeutic efficacy of rIL-2 also appears to be enhanced when used in conjunction with adoptive immunotherapy (see Mule et al., Rosenberg et al,, and Salup et al., supra).

In humans, the administration of large amounts of rIL-2 induces a variety of severe and dose-limiting toxic side effects (Moertel, JAMA (1986) 256:3141). Therefore, much attention has recently focused on alternative strategies that could exploit the therapeutic benefits of rIL-2 while decreasing the expensive and logistic difficulties associated with adoptive immunotherapy, as well as decreasing the toxic sequelae associated with high dose rIL-2 therapy.

It has been previously noted that Renca murine renal cancer could be successfully treated by a therapeutic regimen that combined doxorubicin and adoptive immunotherapy with rIL-2 (Salup, supra, and Salup, Cancer Res. (1986) 46:3358). This approach offers the advantage of requiring daily adminstration of a moderate amount of rIL-2 instead of the larger amounts required for therapeutic effects with rIL-2 alone. However the discovery of agents, either cytokines, noncytokine biologic response modifiers (BRM), or chemotherapeutic drugs, which can successfully act in concert with moderate amounts of rIL-2 in the absence of adoptive immunotherapy is very much needed.

Recent studies have demonstrated that the adoptive transfer of specifically immune or broadly cytotoxic lymphocytes generated in the presence of human rIL-2 can result in the regression of established tumors in mice and humans. Similarly, the administration of rIL-2 alone, in the absence of adoptive immunotherapy, also has been shown to produce some anti-tumor effects in mice and humans. However, the use of adoptive immunotherapy in rIL-2 to treat cancer patients is a complicated, expensive, and toxic form of therapy.

Flavonoids are benzo-γ-pyrone derivatives which are ubiquitous in plants. Historically, flavonoid-containing preparations have been utilized for the treatment of a variety of human diseases.

These natural compounds have been reported to have pleiotropic biological effects (Havsteen B. Commentary: Flavonoids, a Class of Natural Products of High Pharmacological Potency. Biochem. Pharmacol. 1983; 32:1141–1148). These pleiotropic biological effects include binding to and inhibition of the activity of many biological macromolecules such as vital enzymes. Additionally, some flavonoids have been reported to bind divalent ions of heavy metals, influence the permeability of cell membranes, and intercalate into DNA because of their structural similarity with nucleosides. Since these biological effects could be deleterious to rapidly metabolizing cells, interest has arisen in the potential use of flavonoids as anticancer agents (see, for example, Zaharko et al., Cancer Treat. Rap. 1986; 70:1415–1421, and Corbett et al., Invest. New Drugs 1986; 4:207–220).

Thus U.S. Pat. Ser. No. 4,602,034 discloses (oxo-4-4H-(1)-benzopyran-8-yl) alkanoic acids and their derivatives, represented by the formula:

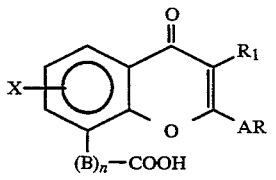

wherein, in the above formula, AR is hydrogen, a phenyl radical which may or may not be substituted, thenyl, furyl, naphthyl, a lower alkyl, cycloalkyl, aralkyl radical, B is a lower alkyl radical, $R_1$ is hydrogen or a phenyl radical, X is hydrogen or a lower alkyl or alkoxy radical, and n is equal to 1, as well as some salts, esters, amino esters and amides of these compounds.

Fifty-seven specific examples of this class of compounds are reported in U.S. Pat. No. 4,602,034. These compounds are disclosed to be useful in the control of tumors, however their reported anticancer activity is limited to P388 lymphocytic leukemia and carcinoma 38 of the colon.

While some flavonoids may well have direct anti-tumor effects, there is some evidence that one of these compounds can also act indirectly. Finlay et al., J. Natl. Cancer Inst. 1988; 80:241–245, present evidence that the pronounced anti-tumor effects achieved in vivo against Lewis lung carcinoma in mice with flavone-8-acetic acid are not mediated by direct toxicity. Finlay et al. note that the tumoricidal activity of flavone-8-acetic acid was more pronounced and occurs more rapidly in vivo than direct cytotoxic effects observed in vitro.

They also observed that Lewis lung carcinoma cells that were implanted in diffusion chambers in the peritoneum of (DBA/6/J X C57BL/6J)$F_1$ mice were not susceptible to the effects of flavone-8-acetic acid administered ip. These results were interpreted by Finlay et al. to mean that the anti-tumor effects of flavone-8-acetic acid are not mediated by soluble factors or of metabolites, but rather through stimulation of host cellular anti-tumor activity. Finlay et al. propose that flavone-8-acetic acid mediates at least some of its anti-tumor effects as a biological response modifier.

Some evidence exists in the literature supporting this conclusion. Ching et al., Eur. J. Cancer Clin. Oncol. 1987; 23:1047–1050, have reported that flavone-8-acetic acid augments splenic natural killer activity. Some of the inventors of the present invention have discovered that flavone-8-acetic acid could augment natural killer activity in nonlymphoid organs (liver and lungs) as well as in the spleen, and that flavone-8-acetic acid plus rIL-2 synergistically augmented natural killer activity in normal and tumor-bearing mice (Wiltrout et al. in "The Journal of Immunology", Vol. 140, No. 9, pp. 3261–3625 (1988)). These studies have shown that the combination of flavone-8-acetic acid plus interleukin-2 has synergistic anti-tumor effects for established murine renal cancer in BALB/c mice.

In another publication, Wiltrout et al., J. Natl. Cancer Inst. 1988; 80:220–222, state that preliminary studies have failed to detect induction of interferon or augmentation of natural killer activity by flavone-8-acetic acid in vitro. The authors state that this suggests the possibility that metabolites of flavone-8-acetic acid may be responsible for some of the biological response modifier-mediated anti-tumor effects of flavone-8-acetic acid in vivo, and that this raises the possibility that active metabolites or congeners of flavone-8-acetic acid may be even more effective. In this vein, the authors note that there has already been one clinical trial of another flavonoid compounds, coumarin, a compound of the formula:

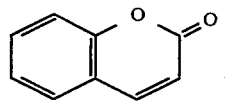

which has demonstrated anti-tumor activity against selected patients with metastatic renal cell cancer (Marshal et al., J. Clin. Oncol. 1987; 5:862–866). However, in preliminary preclinical experiments performed by some of the inventors (Robert Wiltrout and Ronald Hornung), no therapeutic synergy was observed between coumarin and rIL2.

In view of the wide variety of cancers found in animals, and in particular in humans, there is accordingly a strongly felt need for better regimens of the treatment of different types of cancers.

SUMMARY OF THE INVENTION

Accordingly, it is an object of this invention to provide a novel class of flavonoid compounds which can be advantageously used in combination with interleukin-2 (IL-2) in a program for the treatment of a cancer.

It is another object of this invention to provide a novel class of flavonoid compounds which can be used in combination with IL-2 in a program for the treatment of renal cancer.

It is another object of this invention to provide a novel class of flavonoid compounds which can be used in combination with IL-2 to augment natural killer cell activity in a patient in need of such a treatment.

It is another object of this invention to provide a novel class of flavonoid compounds possessing immunomodulatory properties where these properties include the property of stimulating the production of interferon (IFN), thus permitting a low dosage of administration of both the novel compound and IL-2.

It is another object of this invention to provide pharmaceutical compositions containing at least one of the novel flavonoid compounds provided by this invention in association with IL-2.

It is another object of this invention to provide a kit comprising (1) at least one, individually packaged, unit dose of at least one of the novel flavonoid compounds of the present invention, and (2) at least one, individually packaged, unit dose of interleukin-2.

The novel class of flavonoid compounds which have been discovered by the inventors to satisfy all of the above objects of the invention and other objects which will become apparent from the description of the invention given hereinbelow, are flavonoid compounds which possess the immunomodulating property of (1) boosting natural killer (NK) activity and (2) inducing interferon, and (3) belong to the family of flavonoids of the formula (I):

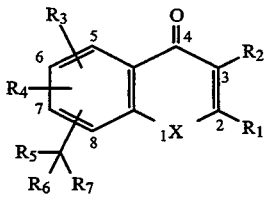

(I)

wherein:

X is N, O, Se, or $S(O)_n$, wherein n is 0, 1 or 2;

$R_1$ is H; $C_{1-7}$ alkyl; naphthyl; phenyl; phenyl substituted by at least one member selected from the group consisting of halogens, $C_{1-12}$ alkyl, trifluoromethyl, hydroxyl, $C_{1-6}$ alkyl, $-(C_{1-6}$-alkylene$)-COOR_{10}$, nitro, $C_{1-16}$(alkyl)carboylamino, benzoyl, $C_{1-6}$-(alkyl)-carboyl, $CONR_{10}R_{11}$, (where $R_{10}$ and $R_{11}$ are each independently H or $C_{1-6}$ alkyl), $NR_{10}R_{11}$, $-N=N-NR_{10}R_{11}$, phenyl substituted by at least one halogen atom, phenol, $O-(C_{1-6}$ alkylene$)-NR_{10}R_{11}$, thiazolyl, and thiazolyl substituted by $C_{1-6}$ alkyl or amino; or $R_1$ is pyridyl; pyridyl substituted by at least one member selected from the group consisting of $C_{1-6}$ alkyls and halogens; trifluoromethyl; benzoyl or benzyl;

$R_2$ is H; phenyl; OH; $C_{1-3}$ alkyl; or $C_{1-3}$ alkoxy;

$R_3$ and $R_4$ are each, independently of each other, H; $C_{1-6}$ alkyl; OH; $C_{1-6}$ alkoxy; or halogen;

$R_5$ is H; $C_{1-3}$ alkyl; CN; or $COOR_{10}$ $R_6$ is H; $C_{1-6}$ alkyl; OH; $-(C_{1-3}$ alkylene$)-CN$; $COOR_{10}$; $-O-CO-(C_{1-6}$ alkyl);

or $R_5$ and $R_6$ together are a group $=CR_{10}R_{11}$, or a group $=NOH$, or a group $=O$ or a group $=CHR_{12}$ (where $R_{12}$ is phenyl, pyridyl, phenyl substituted by at least one member selected from the group consisting of halogen atoms, trifluoromethyl and $C_{1-3}$ alkyls or pyridyl substituted by at least one member selected from the group consisting of halogen atoms, trifluoromethyl and $C_{1-3}$ alkyls);

$R_7$ is H; CHO; $COOR_{10}$; $-CH=CH-COOR_{10}$; $-P(O)(OR_{10}R_{11})_2$; $NR_{13}R_{14}$ (where $R_{13}$ and $R_{14}$ are independently H; phenyl; phenyl substituted by a halogen atom or a $C_{1-3}$ alkyl group or a group $-COOR_{10}$, $-CO-O-CH(CH_3)-COOR_{10}$, morpholinyl, $-C(CH_2OH)_2(CH_3)$, imidazolinyl, $-(C_{1-6}$ alkylene$)-OH$, $-(C_{1-6}$ alkylene$-COOR_{10}$, or $C_{1-3}$ alkoxy, or wherein $R_{13}$ and $R_{14}$ together with the nitrogen atom to which they are both bound from an imidazole or a $N-C_{1-3}$ alkyl-piperazinyl); or $R_7$ is $-CO-C_{1-6}$ alkyl); $-S-(C_{1-6}$ alkyl); $-SH$; $-S-CO-(C_{1-3}$ alkyl); $-S-(CH_2)_mCOOR_{10}$ (with $0<m\leqq 6$); $-CO-O-(C_{1-6}$ alkylene$)-NR_{10}R_{11}$: $-(O-C_{1-6}$ alkylene$)-NR_{10}R_{11}$; $-NR_{10}NR_{10}R_{11}$; $C_{1-6}$ alkyl; $-CONR_{10}R_{11}$; $-CSNR_{10}R_{11}$; thiazolyl; thiazolyl substituted by at least one member selected from the group consisting of $-NH_2$, $C_{1-3}$ alkyl, phenyl and $COOR_{10}$; $-NH-CO-(C_{1-3}$-alkyl); or $-(C_{1-3}-$alkylene$)-CH(NH_2(COOH)$; or $-CR_5R_6R_7$ is a group of one of the formulae

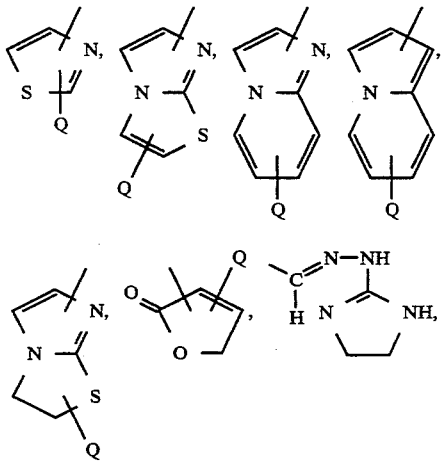

-continued

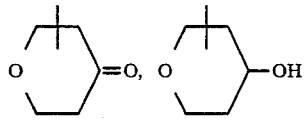

wherein Q is at least one member selected from the group consisting of H; $COOR_{10}$; phenyl; $-O-(C_{1-3}$-alkylene$)-COOR_{10}$; $C_{1-3}$ alkyl; $-O-CS-NR_{10}R_{11}$; $-O-(C_{1-3}$-alkylene$)-NR_{10}R_{11}$; OH: $C_{1-3}$ alkoxy; and $NR_{10}R_{11}$; or wherein any two of $R_3$, $R_4$, $R_5$, $R_6$ and $R_7$ together form a benzene ring; or a benzene ring substituted by $-(C_{1-3}$-alkylene$-COOR_{10}$; $-(C_{1-3}-$alkyl$)-OH$, $COOR_{10}$, or $-(C_{1-3}$-alkylene$)-O-(CO-C_{1-3}-$alkyl); or a naphthalene system; or a naphthalene system substituted by $-(C_{1-3}$-alkylene$)-COOR_{10}$, $-(C_{1-3}$-alky$)-OH$, $COOR_{10}$, or $-(_{1-3}$-alkylene$)-O-CO-(C_{1-3}$-alkyl); and physiologically acceptable salts thereof, with the proviso that when $-CR_5R_6R_7$ is situated at the 8-position of formula (I) and X is O (i) when $R_2$, $R_3$, $R_4$, $R_5$ and $R_6$ are all H and $R_7$ is CN, $R_1$ is other than phenyl, 2-thenyl, 3,4-dimethoxy phenyl, 3-methoxy phenyl, para-tolyl, 2-furyl, 2naphthyl, 4-methoxy phenyl, benzyl, methyl, or cyclohexyl;

(ii) when $R_2$, $R_3$, $R_4$, $R_5$ and $R_6$ are all H and $R_7$ is COOH, $R_1$ is other than phenyl, 2-thenyl, 3-methoxy phenyl, 3,4-dimethoxy phenyl, 2-furyl, para-tolyl, 2naphthyl, 4-methoxy phenyl, cyclohexyl, benzyl, or methyl;

(iii) when $R_2$, $R_3$, $R_4$, $R_5$ and $R_6$ are all H and $R_7$ is $-CO-O-CH_2CH_2-N(C_2H_5)_2$, $R_1$ is other than phenyl, 2thenyl, para-tolyl, or 4-methoxy phenyl;

(iv) when $R_2$, $R_3$, $R_4$, $R_5$ and $R_6$ are all H and $R_7$ is

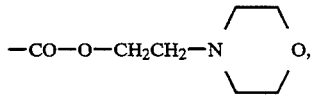

$R_1$ is other than phenyl;

(v) when $R_2$, $R_3$, $R_4$, $R_5$ and $R_6$ are all H and $R_7$ is $-CO-O-(CH_2)_3N(CH_3)_2$; $R_7$ is other than phenyl;

(vi) when $R_2$, $R_3$, $R_4$, $R_5$ and $R_6$ are all H and $R_7$ is $-CO-O-C_2H_5$, $R_1$ is other than phenyl;

(vii) when $R_2$, $R_3$, $R_4$, $R_5$ and $R_6$ are all H and $R_7$ is $-CO-O-CH_3$, $R_1$ is other than phenyl or 2-thenyl;

(viii) when $R_2$, $R_3$, $R_4$, $R_5$ and $R_6$ are all H and $R_7$ is $-CO-O-Na$, $R_1$ is other than phenyl;

(ix) when $R_2$, $R_3$, $R_4$, $R_5$ and $R_6$ are all H and $R_7$ is $-CO-O-CH_2CH_2OH$, $R_1$ is other than phenyl;

(x) when $R_2$, $R_3$, $R_4$, $R_5$ and $R_6$ are all H and $R_7$ is $-CO-NH-CH_2CH_2N(C_2H_5)_2$, $R_1$ is other than phenyl;

(xi) when $R_2$, $R_4$, $R_5$ and $R_6$ are all H, $R_3$ is methyl at the 6-position of formula (I) ($6-CH_3$) and $R_7$ is COOH, $R_1$ is other than phenyl;

(xii) when $R_2$, $R_4$, $R_5$ and $R_6$ are all H, $R_3$ is 6—$CH_3$ and $R_7$ is $COOH_3$, $R_1$ is other than phenyl;

(xiii) when $R_2$, $R_4$, $R_5$ and $R_6$ are all H, $R_3$ is 6—$CH_3$ or 6—$OCH_3$ and $R_7$ is —CO—O—$CH_2CH_2$—$N(CH_2H_5)_2$, $R_1$ is other than phenyl;

(xiv) when $R_2$ and $R_3$ are H, $R_4$ is H or 6-$CH_3$, $R_5$ is methyl, $R_6$ is —$COOC_2H_5$, and $R_7$ is —$COOC_2H_5$, $R_1$ is other than phenyl;

(xv) when $R_2$ and $R_3$ are H, $R_4$ is H or 6-$CH_3$, $R_5$ is H, $R_6$ is $CH_3$ and $R_7$ is COOH, $R_1$ is other than phenyl;

(xvi) when $R_2$, $R_3$, $R_4$ and $R_5$ are all H, $R_6$ is $CH_3$and $R_7$ is —CO—O—$CH_2CH_2N(C_2H_5)_2$, $R_1$ is other than phenyl;

(xvii) when $R_2$, $R_3$, $R_4$ and $R_7$ are all H, $R_5$ and $R_6$ are =O, $R_1$ is other than phenyl;

(xviii) when $R_2$, $R_3$, $R_4$, and $R_5$ are all H and —$CR_5R_6R_7$ is —CH=CH—$COOCH_2CH_2N(C_2H_5)_2$,

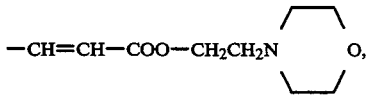

$CH_2CH(COOC_2H_5)_2$, or —$CH_2CH_2COOH$, $R_1$ is other than phenyl;

(xix) when $R_2$ and $R_3$ are both H, $R_4$ is 6-$CH_3$ or 6-$OCH_3$, $R_6$ and $R_7$ are H and $R_5$ is CN, $R_1$ is other than phenyl;

(xx) when $R_2$ and $R_3$ are H, $R_4$ is 6-$OCH_3$ or 6-OH, and $R_5$ and $R_6$ are H and $R_7$ is COOH, $R_1$ is other than phenyl;

(xxi) when $R_2$ is phenyl, $R_3$ and $R_4$ are H, $R_5$ and $R_6$ are =O, or $R_6$ is CN or COOH, $R_1$ is other than phenyl.

The present invention provides also a method and regiment for treating cancer, comprising coadministering at least one of the flavonoid compounds provided by this invention and interleukin-2 to a patient in need thereof.

BRIEF DESCRIPTION OF THE FIGURES

A more complete appreciation of the invention and many of its attendant advantages will be readily obtained as the same becomes better understood by reference to the following detailed description when considered in connection with the following FIGURES, wherein.

Figure 1:
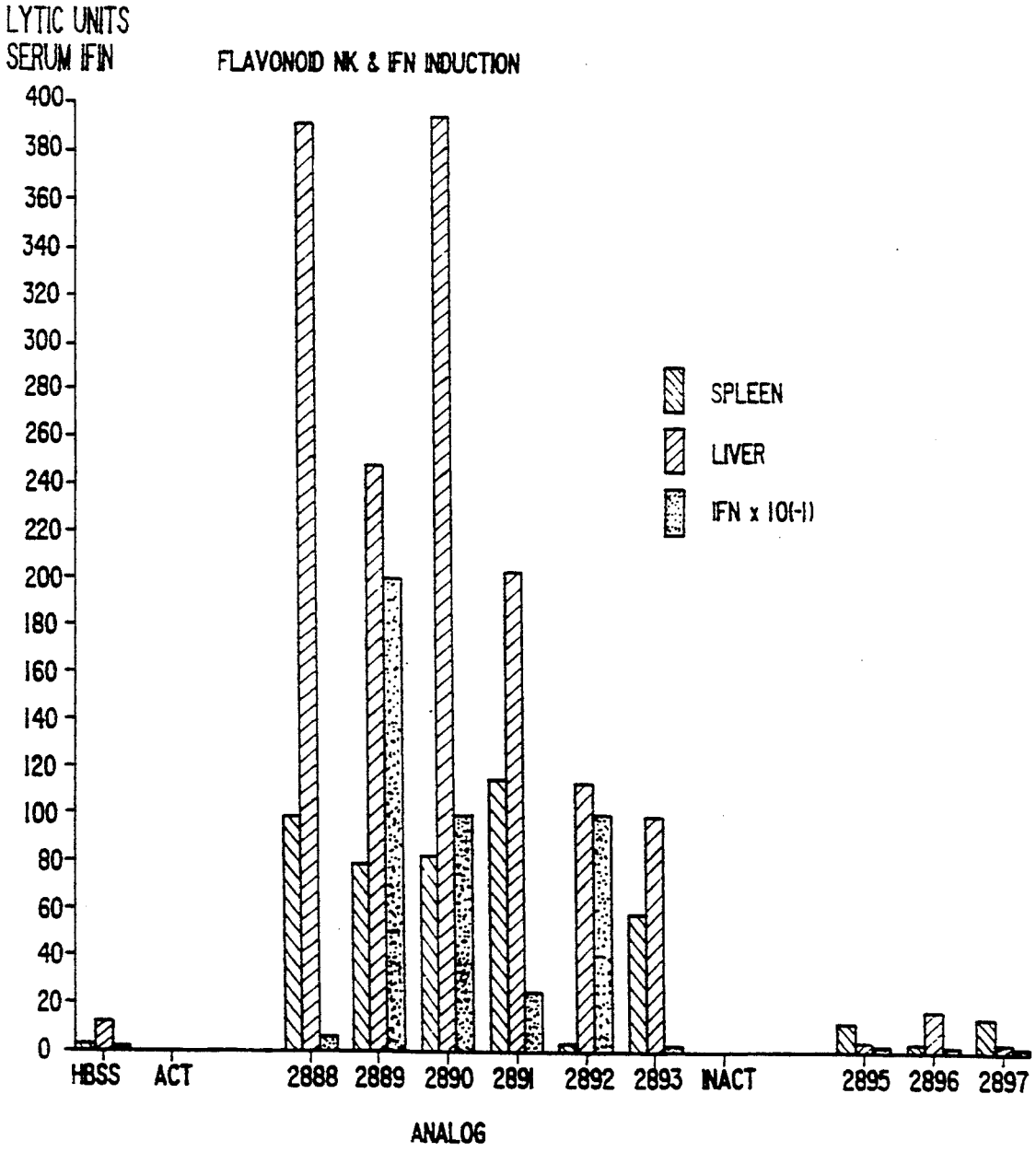
FIG. 1 illustrates the natural killer (NK) and interferon (IFN) induction in vivo for various flavonoid compounds.

FIGS. *2a* and *2b* show the effect on survival rate of treatment of Renca-bearing mice with various flavonoids without (a) or with interleukin-2 (IL-2) (d);

FIGS. *3a* and *3b* show the effect on survival rate of treatment of Renca-bearing mice with various flavonoids outside the present invention and/or IL-2.

DETAILED DESCRIPTION OF THE PREFERRED EMBODIMENTS

The flavonoid compounds of formula (I) are disclosed in U.S. patent application Ser. No. 07/178,315, filed Apr. 6, 1988.

All of the flavonoids used in the present invention must possess the immunomodulatory activity of (1) boosting NK activity, and (2) inducing interferon. Preferably they also demonstrate both in vivo and in vitro cytotoxic effect. All of these characteristics are readily determined by following the following protocols.

The immunomodulatory activity of boosting NK activity is readily determined in accordance with the protocol outlined by Wiltrout et al. in *J. Exp. Med.* (1984), vol. 160, p. 1431–1449, which is hereby incorporated by reference. Using this protocol, the flavonoid compounds of the present invention must be capable of boosting NK activity at least 2-fold, preferably at least 3-fold, and most preferably at least 4-fold, as measured in lytic units. (See "In Vitro Methods in Cell Mediated and Tumor Immunity", eds. Barry R. Bloom and John R. David, pub. Academic Press (1976), p. 427, for the definition of lytic units.)

The immunomodulatory activity of inducing IFN is readily determined in accordance with the protocol outlined by Degree et al. in *Acta Pathol. Microbio. and Immuno. Scan.* (1982), vol. 80, p. 863, which is hereby incorporated by reference. Using this protocol the IFN induction should provide at least 10 units of IFN per ml of serum, preferably at least 100 units of IFN per ml of serum, and most preferably at least 1,000 units of IFN per ml of serum.

It must be noted that these IFN induction values represent peak IFN concentrations. Using this test these peak values are reached generally within 5 hours after administration of the flavonoid so that the IFN level should be measured over approximately 6 hours, or longer, until the peak value is determined.

As noted above, preferably the present compounds should demonstrate a cytotoxic effect, both in in vitro and in in vivo assays.

This in vitro assay is performed as follows. The compound tested is placed on a paper disk which is set in the middle of an agar-agar base in which a culture of a selected tumor has been placed. The activity is measured by examining the inhibition of growth of the tumor being cultured. The growth is measured as a function of units (1 unit=25 microns) which are inhibited. These units represent the surface of the growth of the tumor culture. A product is considered to represent a notable level of activity if the number of zones which are inhibited is superior to 250. The tumors used in these tests can be adinocarcinomic pancreatic PO3 and colon CO8.

In the tests run by the inventors, in the inhibition of tumor PO3 the compounds of formulae 19, 58 and 70 at an application of 1000 micrograms per disk an inhibition value of from 900, 350 and 400, respectively. In the case of tumor CO8, the compounds of formulae 31, 19 and 70 administered at 1000 micrograms per disk displayed an inhibition value of 500, 450 and 500, respectively.

The in vivo assay is performed by evaluating the efficacy of the compound being tested on the C38 murine colon model described in U.S. Pat. No. 4,602,034.

It must thus be noted that not all flavonoids which fall within the generic formulae given in this text are used in the present invention. The flavonoids which are used in the invention are those (1) which fall within the formulae given and (2) which possess the immunomodulatory activity of (2.1) boosting NK activity, and (2.2) inducing interferon.

The flavonoids of this invention have been discovered by the inventors to surprisingly synergize with IL-2. IL-2 at near toxic dosages has been shown to induce antitumor effects in rodents and human. The present coadministration of IL-2 and the flavonoid allows for the augmentation of the therapeutic effect of IL-2 without the requirement of the administration of toxic doses of IL-2 to the patient. The present invention thus solves the problem of using IL-2 in antitumor therapy, where IL-2 had to be administered at near toxic or at toxic levels to obtain antitumor effects.

The interleukin-2 which can be used in accordance with the present invention includes all proteins which exhibit the activity of interleukin-2 in vivo. These proteins are well known. See, for example, Taniguchi et al., U.S. Pat. No. 4,738,927. In a preferred embodiment, recombinant interleukin-2 (rIL-2) is used, and most preferably recombinant human interleukin-2 is used.

As illustrated in FIG. 1 the inventors have discovered that some of the flavonoid compounds of the present invention potently augment both the natural killer activity and IFN activity in the spleen, liver, lungs and peritoneum in a dose-dependent manner following either intravenous or intraperitoneal administration.

In FIG. 1 the IFN levels reported were measured at approximately 24 hours after administration, and thus the values of IFN induction reported in the FIGURE are values lower than the peak values which are normally observed at 4 to 6 hours after administration.

Figure 2A:
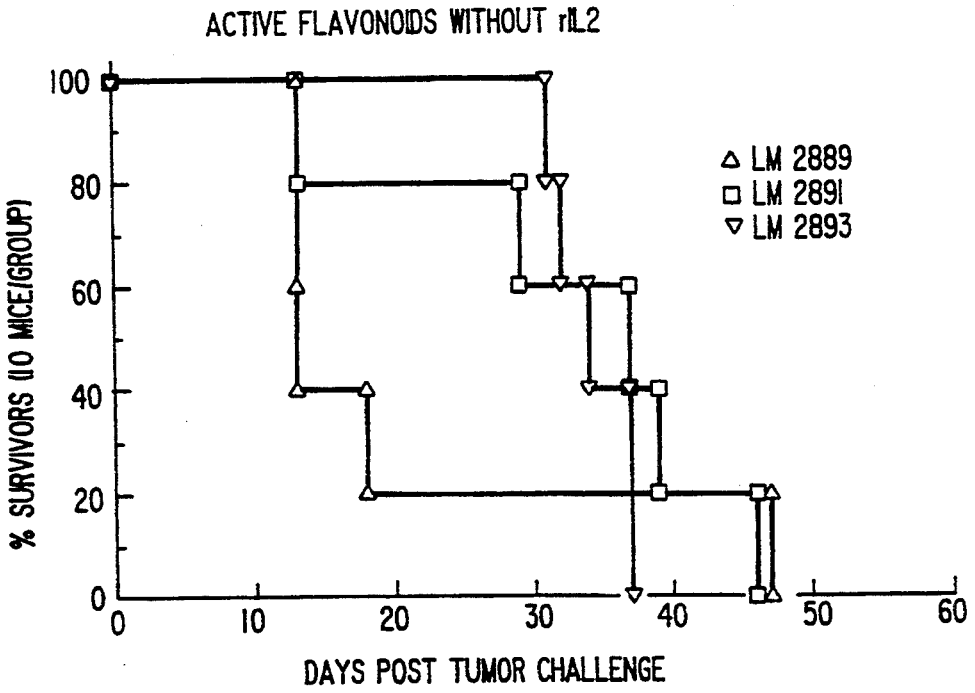
Figure 2B:
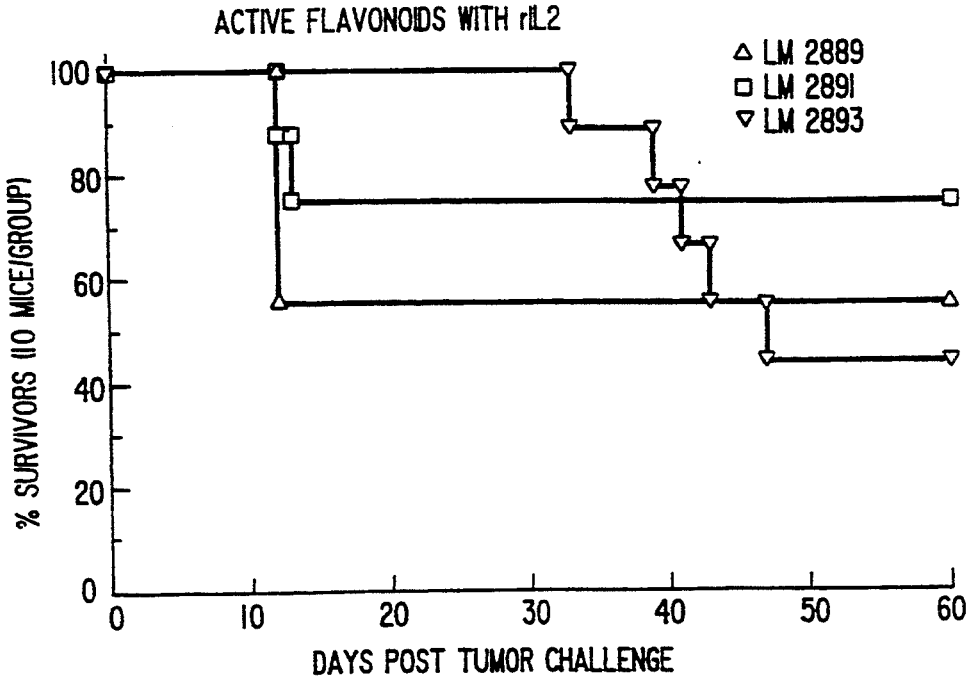

AS illustrated in FIGS. 2*a*, 2*b*, 3*a* and 3*b* combined treatment of established cancers with the present flavonoid compounds and IL-2 results in a dramatic increase in the long-term survival of patients, while the independent use of the flavonoid compounds or the interleukin-2 is unable to induce such long-term survival. FIGS. 2*a*, 2*b*, 3*a* and 3*b* illustrate the effect of treatment with different flavonoid compounds and/or rIL-2 on the survival of Renca-bearing mice. FIGS. 2*a* and 2*b* demonstrate the survival rate of these mice treated, on the one hand, simply with one of the flavonoids of the present invention (FIG. 2*a*), and, on the other hand, with a combination of one of the flavonoids of the present invention and rIL-2 (FIG. 2*b*). A comparison between these two figures demonstrates the notable improvement in survival rates due to the rIL-2 and flavonoid coadministration.

Figure 3A:
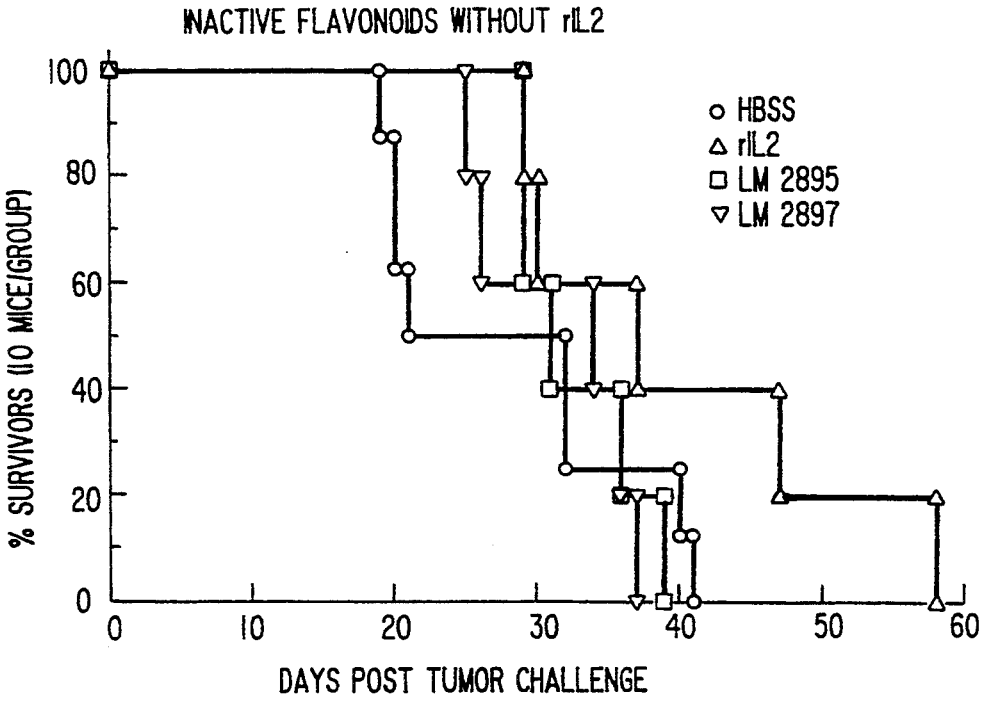
Figure 3B:
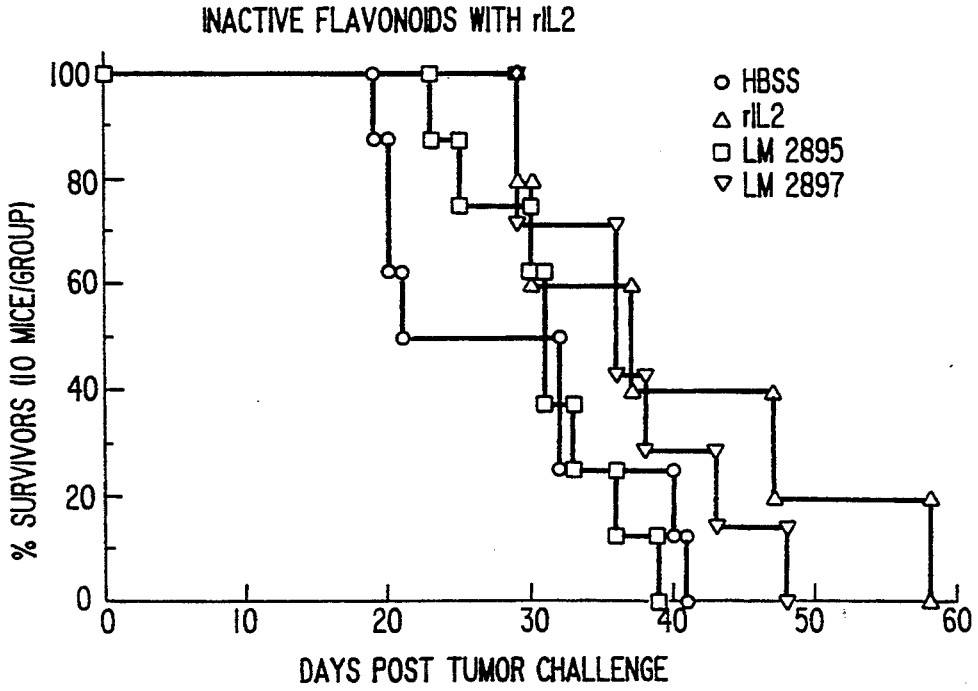

FIGS. 3*a* and 3*b* provide data obtained with flavonoids falling outside of the present invention. The flavonoid compounds used in obtaining the data reported in these figures do not possess either the immunomodulatory activity of boosting NK activity or of inducing interferon. FIG. 3*a* provides data obtained on Renca-bearing mice by administration of the flavonoid compound only. FIG. 3*b* provides data obtained by coadministration of a flavonoid compound falling outside of the present invention with rIL-2.

The combined use of the flavonoid compounds of the present invention and interleukin-2 thus provides a significant antitumor efficacy using subtoxic doses of IL-2 even without accompanying adoptive immunotherapy. The present invention thus also provides a treatment regimen for cancer which enhances the effectiveness of interleukin therapy. The cancers which can be treated in accordance with the present invention include renal cancer and melanoma. The present invention could also be used in the treatment of colon cancer, lung cancer, breast cancer, and cancers associated with the GI tract or the genital/urinary tract.

The flavonoid compounds can be desirably administered by bolus injection, continuous infusion, or delivery from an csmotic pump in close proximity to the administration of the interleukin-2 by any of the above routes to treat cancer in animals, and in particular, humans. The IL-2 is administered via any suitable known method.

The flavonoids and IL-2 can be conveniently administered intravenously or intraperitoneally, in a suitable carrier. Thus the present invention also provides pharmaceutical compositions containing at least one of the present flavonoids together with IL-2 or a kit having individualized packaged units of the flavonoid and IL-2. These pharmaceutical compositions are prepared in accordance with the general knowledge in the pharmaceutical art. They can be pharmaceutical compositions suitable for intravenous injection, oral administration, nasal administration (e.g. a nasal spray) or eye drops. The pH of these compositions is preferably at a value compatible with human administration, e.g. the pH is at a value of between 7 and 8. Preferably these carriers are aqueous. Salts of the flavonoids are preferred for use in these carriers because of their higher solubility therein.

Carriers which can be used in the present invention include suitable pharmaceutically acceptable carriers comprising excipients and auxiliaries which facilitate processing of the active compounds into preparations which can be used pharmaceutically. Solutions for administration intraperitoneally or intravenously contain from about 0.1 to about 99.5 percent by weight, and preferably from about 25 to 85 percent by weight, of active ingredient(s), together with the excipient. When a pharmaceutical composition contains a combination of flavonoid and IL-2 these two materials are present in amounts suitable to permit the desired administration dosage of each discussed infra.

Suitable formulations for parenteral, intraperitoneal, or intravenous administration of the active compounds may include suspensions of the active ingredients as appropriate oily injection suspensions. Suitable lipophilic solvents or vehicles include fatty oils, for example sesame oil, or synthetic fatty acid esters, such as ethyl oleate or triglycerides. Aqueous injection suspensions may contain substances which increase the viscosity of the suspension such as sodium carboxymethylcellulose, sorbitol, or dextran.

As noted above the flavonoid compound is preferentially administered by bolus injection, continuous infusion, or delivery from an osmotic pump in close proximity to the administration of IL-2. The optimal dose of IL-2 required for use with the flavonoid compound is in the range of from $10^5$ units per $m^2$ preferably $10^6$ units per $m^2$ to $30\times10^6$ units per $m^2$. The flavonoid is administered at dosages falling within the range of from about 10 mg per $m^2$ to about 20,000 mg per $m^2$, but preferably not more than 10,000 mg per $m^2$.

The administration of IL-2 must begin at the time of flavonoid administration or not more than 24 hrs thereafter. The IL-2 can be administered one time per day for at least two days beginning after the flavonoid compound treatment and the treatment can be continued up to patient recovery.

The dosage of the flavonoid compound in interleukin-2 used, the route of administration, and the carriers and/or adjuvants used may of course vary based on the tumor type being treated and in view of known procedures for treatment of such tumors, noting that the combination of the flavonoid compounds and IL-2 provides synergistic anti-tumor activity.

As noted above, the coadministration of these flavonoid compounds with IL-2 exhibits dramatically improved therapeutic effects which are generally better to those achieved previously with chemotherapeutic drugs and adoptive immunotherapy against renal cancer.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The terms "alkyl", "alkylene", and "alkoxy" used in this document refer to linear or branched or cyclic, saturated or unsaturated alkyl, alkylene, or alkoxy groups unless otherwise specified.

The term "halogen" in this document refers to fluoro, chloro, bromo and iodo, preferably fluoro and chloro, and most preferably fluoro, unless otherwise specified.

The term "salt" is used in this document in accordance with its accepted definition to include all possibilites in which the compound of the invention is either the cationic or the anionic component of the salt. The compounds of the invention have acidic and/or basic functionalities which can of course be both present in the same molecule.

With acidic functionalities, the salts of the compounds are obtainable through reaction with either an organic or an inorganic base. Such bases include all bases known to be useful to make physiologically acceptable salts, for example, $Na_2CO_3$, $NaHCO_3$, KOH, NaOH, $NH_3$ and bases of the formula $NR_{27}R_{28}R_{29}$ where $R_{27}$, $R_{28}$ and $R_{29}$ are H, $C_{1-6}$ alkyl, $C_{1-6}$ hydroxyalkyl, etc.

With basic functionalities, the salts of the compounds are obtained by reaction with inorganic or organic acids. The acids which can be used are all the acids known to be useful to make physiologically acceptable salts, for example, HC1, HBr, HI, phosphoric acid, phosphonic acid, para-toluene sulfonic acid, formic acid, oxalic acid, fumaric acid, etc. These salt forms of the compounds are generally readily soluble in water, and permit administration of the compounds in solution to a patient.

The flavonoid compounds of the present invention, when not in solution in a pharmaceutically suitable carrier, are preferably lyopholized before storage.

In lypholized form they are more easily dissolved in a pharmaceutical medium.

In a preferred embodiment, when $R_1$ is $C_{1-7}$ alkyl, the preferred alkyl groups are $C_{1-3}$ alkyl, e.g., methyl, ethyl, n-propyl or iso-propyl. When $R_1$ is a substituted phenyl group, the substituents are $C_{1-3}$ alkyl, halogen, trifluoromethyl, hydroxy, $C_{1-3}$ alkoxy or nitro. Phenyl substituted by one halogen atom is particularly preferred. When $R_1$ is a substituted pyridyl, the same preferred substituents for phenyl as given above, are also preferred.

The groups $R_2$, $R_3$ and $R_4$ are preferrably H. Groups $R_5$ and $R_6$ are preferably $=CR_{10}R_{11}$ with $R_{10}=R_{11}=H$.

Preferably $R_7$ is a group which is metabolized in vivo to leave an acidic function on the flavonoid nucleus for $R_7$. Accordingly, —CHO, $—COOR_{10}$, $P(O)(OR_{10}R_{11})$, $—CH_2CH—COOR_{10}$, and $—CONR_{10}R_{11}$ are preferred for $R_7$.

In another of its preferred embodiments, the present invention provides flavonoid compounds which possess the immunomodulating property of (1) boosting NK activity and (2) inducing interferon, and (3) belong to the family of flavonoids of the following formula (II)

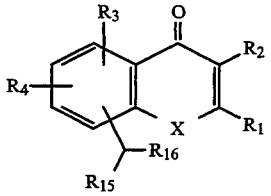

(II)

wherein:

X is N, O, Se, or $S(O)_n$ where n is 0, 1 or 2;

$R_1$ is methyl, phenyl, substituted phenyl, biphenyl, or trifluoromethyl;

$R_2$ is hydrogen or OH, or $R_1$ and $R_2$, together, form a naphthalene system fused to the hetero-ring of the flavonoid nucleus;

$R_3$ and $R_4$ are hydrogen, alkyl, $C_{1-6}$ alkoxy hydroxy, halogen, or $R_3$ and $R_4$ together form a benzene system fused to the benzene ring of the flavonoid nucleus;

$R_{15}$ is hydrogen when $R_{16}$ is a carboxylic radical, a carbamyl radical, a mercapto radical, a carboxymethylthio radical, an aminoether radical, a phosphonic group, a substituted hydrazino, an amino group, a substituted amino group, a lower alkyl group, $—CONH-R_{17}$, $—CS-NH-R_{18}$ (where $R_{17}$ and $R_{18}$ are $C_{1-6}$ alkyl), oximino, or a substituted thiazolyl, $NR_{19}R_{20}$, (wherein $R_{19}$ and $R_{20}$ are hydrogen, an aromatic group, a substituted aromatic group, an hydroxyalkyl group, a carboxymethylene group, or $R_{19}$ and $R_{20}$ together form an imidazole ring or N-methyl-piperazinyl);

when $R_{15}$ is R-CH=, $R_1$ is hydrogen, phenyl, 3-pyridyl, 4-pyridyl, and $R_{16}$ is COOH.

$R_{15}$ and $R_{16}$ can also be a tetronic moiety or a substituted tetronic moiety.

When $R_{16}$ is =O, $R_{15}$ is preferably —COOH, —CH=CH-COOH, $—CH_3$, $—CH_2$-Br, —CH=CH-AR, with AR being H, phenyl, 3-pyridyl or 4-pyridyl; or $R_{15}$ and $R_{16}$ can together form a tetronic moiety, a substituted thiazolyl moiety, indolizinyl, imidazo [2,1-b] thiazolyl, imidazo [1,2-a] pyridino, a tetrahydropyran which is substituted or a cyclic lactonic moiety.

When $R_4$ and $R_{15}$ together form a benzene system, $R_{16}$ is preferably COOH, or $CH_2COOH$.

When $R_1$ and $R_2$ together form a naphthalene system, preferably $R_{15}$ is hydrogen and $R_{16}$ is COOH.

When $R_3$ and $R_4$ form a benzene system, preferably $R_{15}$ is hydrogen and $R_{16}$ is COOH.

When $R_{15}$ is hydroxyl, $R_{16}$ is preferably COOH or $—CH_2CH_2COOH$.

When $R_{15}$ is =O, $R_{16}$ is preferably COOH, or $CH_2CH_2COOH$, —CH=CH-COOH.

Again preferably the compounds should also demonstrate a cytotoxic effect.

These compounds and their derivatives are particularily useful as antitumor agents, notably as antipancreatic cancer agents.

The compounds of formula (II) can be prepared in accordance with one of the methods of preparation generally outlined below which provides these compounds in good yields.

In a first process, a compound of (III)

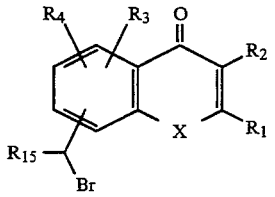

(III)

is reacted either with (1) alkaline nitrile component followed by hydrolysis, or (2) with an amine ($NR_{19}R_{20}$), or (3) with triethylphosphite followed by hydrolysis, or (4) with a compound of formula $R_{32}$—SH, or $R_{32}$—OH, wherein $R_{32}$ can be —$CH_2COOEt$ or —$CH_2CH_2$—$N(C_2H_5)_2$.

In another process to obtain the compounds of formula (II), the compound of formula (III) is reacted either with (1) potassium acetate followed by hydrolysis, oxidation, bromination and condensation with thiourea, thioacetamide, thiobenzamide, 2-amino thiazole, 2-methylpyridine, 2-aminothiazole, or ethoxycarbonyl acetamide.

Compounds of formula (II) can also be obtained by reacting appropriate compounds of formula (II) wherein $R_{15}$ is hydrogen and $R_{16}$ is COOH with an alpha halogenated ester followed by cyclization.

Compounds of formula (II) can also be obtained by reacting appropriate compounds of formula (III) with hexamethylene tetramine and condensation of the carbonylated compound obtained with thiosemicarbazide, hydrazinoimidazole, hydroxylamine, or malonic acid.

Compounds of formula (II) can also be obtained by reacting appropriate compounds of formula (II) wherein $R_{15}$ is hydrogen and $R_{16}$ is COOH with bromine followed by potassium acetate with subsequent hydrolysis and then oxidation.

Compounds of formula (II) can also be obtained from appropriate compounds of formula (II) wherein $R_{15}$ is methyl and $R_{16}$ is $COO(C_2H_5)$ by reaction with methyl iodide followed by hydrolysis.

Compounds of formula (II) can also be obtained by reacting compounds of formula (II) wherein $R_{15}$ is hydrogen and $R_{16}$ is CN or COOH with $H_2S$ or ammonia in the presence of carbonyldiimidazole.

In another of its embodiments, the present invention provides flavonoid compounds which possess the immunomodulating property of (1) boosting natural NK activity and (2) inducing interferon, and (3) belong to the family of flavonoids of the formula (IV)

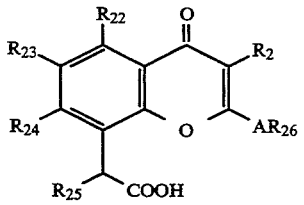

(IV)

wherein:

$AR_{26}$ is phenyl, substituted phenyl, biphenylyl, pyridyl, or trifl uoromethyl;

$R_2$ is hydrogen, hydroxyl, or $C_{1-3}$ alkoxy;

$R_{22}$ is hydrogen, hydroxyl, or $C_{1-6}$ alkoxy;

$R_{23}$ is hydrogen, or fluoro;

$R_{24}$ is hydrogen, or hydroxy;

$R_{25}$ is hydrogen, 2-methylpyridyl, benzylidene, 4-methylenepyridyl, or methylene; or $R_{22}$ and $R_{23}$ together form a benzene ring fused to the flavonoid nucleus;

$R_{23}$ and $R_{24}$ form a benzene ring fused to the flavonoid nucleus; or $R_{25}$ and $R_{24}$ form a benzene ring fused to the flavonoid nucleus.

Again, preferably the flavonoids also demonstrate a cytotoxic effect.

The compounds of (IV) can be obtained by the hydrolysis of the nitriles of formula (V):

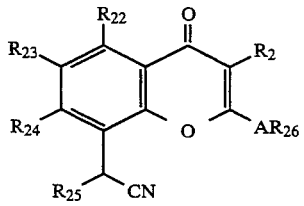

(V)

wherein $AR_{26}$, $R_2$, $R_{22}$, $R_{23}$, $R_{24}$ and $R_{25}$ are as defined above. The nitriles of formula (V) are obtained by the reaction of an alkali cyano compound with a compound of formula (VI):

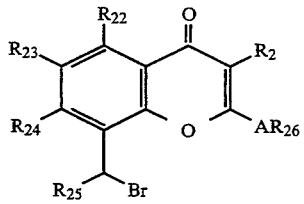

(VI)

wherein $AR_{26}$, $R_2$, $R_{22}$, $R_{23}$, $R_{24}$ and $R_{25}$ are as defined above.

With compounds of formula (IV) when $R_{25}$ is methylene or arylidene, the compounds are obtained by the reaction of compounds of formula (IV) wherein $R_{25}$ is hydrogen, with N,N,N,N-tetramethyldiaminomethane or with an aromatic aldehyde or an heteroaromatic aidehyde.

The compounds of formula (IV) have been discovered to surprisingly possess immunomodulating properties. The inventors have now discovered that the compounds of formula (IV) possessed a surprisingly high activity with the immune system and that in particular they stimulated the activity of killer cells and induce the formation of interferon (INF).

The inventors have also discovered that the following flavonoids can be used in accordance with the present invention:

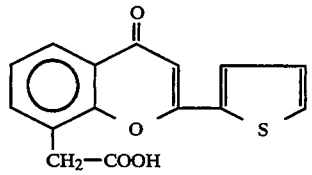

FORMULA 312

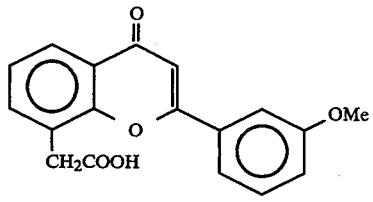

FORMULA 329

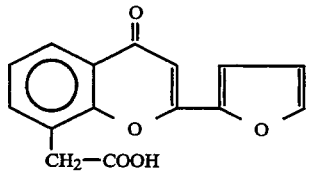

FORMULA 339

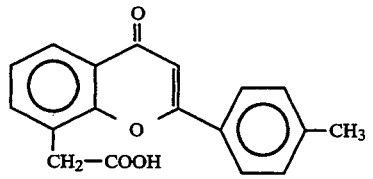

FORMULA 341

These compounds are, respectively, [oxo-4-(thenyl-2)-2-4H-[1]-benzopyran-8-yl]acetic acid (FORMULA 312), [(methoxy-3-phenyl)-2-oxo-4-4H-[1]-benzopyran-8-yl]acetic acid (FORMULA 329), [(furyl-2)-2-oxo-4-4H-[1]-benzopyran-8-yl]acetic acid (FORMULA 339), and [(methyl-4-phenyl)-2-oxo-4-4H-[1]-benzopyran-8-yl]acetic acid (FORMULA 341).

In the above compounds of formulae 312, 329, 339 and 341, the carboxylic acid group, —COOH, can be present either in free acid form, as the alkali metal derivative thereof, or as are any derivative which hydrolyzes in vivo to yield the free acid or its salt. These esters include groups wherein the carboxylic acid group, —COOH, is exchanged for one of the following groups: $—COOR_{10}$, —CO—O—($C_{1-6}$ alkylene)—$NR_{10}R11$, $—CONR_{10}R_{11}$.

Other features of the invention will become apparent in the course of the following descriptions of exemplary embodiments which are given for illustration of the invention and are not intended to be limiting thereof.

Assessment of NK activity. Augmentation of NK activity by a flavonoid compound and/or rIL-2 was assessed in a 4-hr $^{51}Cr$ release assay against the YAC-1 tumor target. Effector leukocytes were isolated from spleen, peritoneal cavity, lungs, and liver as previously described (*J. Exp. Med.*, vol. 160, 1431 (1984) and *J. Immunol.*, vol. 135, 1477 (1985)). NK activity was expressed as either $$\% \text{ specific cytotoxicity} = \frac{\text{cpm released from test well} - \text{cpm released from target cells alone}}{\text{total } SDS\text{-solubilized cpm}} \times 100$$

or LU/$1\times10^7$ cells, with one LU being the number of effector cells required to lyse 20% or 40% of the target cells. Statistical comparisons in NK activity were performed by the student's t-test.

Tumor model. The model used for these studies is the Renca renal adenocarcinoma, a tumor that originated spontaneously and is maintained by serial transplant in BALB/C mice (JNCI, vol. 50, 1013 (1973)). The growth characteristics of this tumor have been previously described in detail (*J. Immunol.*, vol. 138, 641 (1987)). After injection of $1\times10^5$ tumor cells under the renal capsule, the solid tumor mass develops rapidly with direct extension to the peritoneal cavity by days 7 to 9 and metastasis to regional lymph nodes and the liver shortly thereafter. Surgical resection of the primary tumor-bearing kidney is potentially curative before day 8 but not thereafter when mice succumb to peritoneal carcinomatosis and subsequent metastatic disease. Flavonoid was administered by injection of 125 mg/kg i.v. and 125 mg/kg i.p., whereas various doses of rIL-2 were delivered by the i.p. route. Routinely, flavonoid was administered 2 to 4 h after nephrectomy of the primary tumor-bearing kidney on day 11, and rIL-2 was administered once per day for 4 successive days beginning on the day after nephrectomy and FAA treatment. Statistical analysis of survival data was performed by the $\chi^2$ test.

Serum interferon activity

The flavonoid compounds, at concentrations of from 125 mg/kg to 250 mg/kg, were administered i.v. for various periods of time ranging from 1 hour to 6 days before harvesting serum for assessment of IFN activity. Serum IFN activity was determined by using the vesicular stomatitis viral inhibition assay described by Degre, N; Dahl, H. *Acta Pathol. Microbio. and Immuno. Scan.* (1982), vol. 80, p. 863.

IL-2 activity

The flavonoid compound was administered by injection of e.g. 125 mg/kg i.v. and e.g. 125 mg/kg i.p., whereas various doses of rIL-2 were delivered by the i.p. route. Routinely, flavonoid compound was administered 2 to 4 hours after nephrectomy of the primary tumor-bearing kidney on day 11 and rIL-2 was administered once per day for 4 successive days beginning on the day after nephrectomy and flavonoid treatment. Statistical analysis of survival data was performed by the $\chi^2$ test.

The results obtained from the studies are tabulated in Table 1 below.

TABLE 1

| Compound | NK | IFN | Synergistic Therapy With IL-2 |
|---|---|---|---|
| LM2888 | + | I | I |
| LM2889 | + | + | + |
| LM2890 | + | + | + |
| LM2891 | + | + | + |
| LM2892 | + | + | I |
| LM2893 | + | I | + |
| LM2895 | – | – | – |
| LM2896 | – | – | – |
| LM2897 | – | – | – |

+ = positive activity
– = no activity
I = inconclusive

The augmentation of NK in the spleen and the liver and IFN induction activity following administration of the flavonoid compounds tested is reported in FIG. 1.

The compounds listed in Table 1 and FIG. 1 are the following (note that in FIG. 1 the "LM" component is omitted for clarity).

LM2888: sodium salt of the compound of formula 339
LM2889: sodium salt of the compound of formula 329
LM2890: sodium salt of the compound of formula 19
LM2891: sodium salt of the compound of formula 42
LM2892: sodium salt of the compound of formula 67
LM2893: sodium salt of the compound of formula 25
LM2895: sodium salt of the compound of formula 92
LM2896: sodium salt of the compound of formula 12
LM2897: sodium salt of the compound of formula 23

FIGS. *2a, 2b, 3a* and *3b illustrate the effect of treatment with various flavonoids and/or rIL-2* on the survival of Renca-bearing mice. BALB/C mice (e.g. 10/group) were injected i.v. with $1\times10^5$ Renca tumor cells on day 0. On day 11 the tumor-bearing kidney was removed and 2 to 4 h later flavonoid (125 mg/kg i.v.+125 mg/kg i.p.) was administered to appropriate groups. Subsequently, beginning on day 12, some of the flavonoid pretreated mice and two groups of previously untreated mice received four daily i.p. injections of rIL-2 at doses of 30,000 U/day. Mice were then monitored for survival and statistical analyses performed by the $\chi^2$ test.

Overall, these results demonstrate that the use of the flavonoid compounds in association with moderate doses of rIL-2 affords appreciably improved long-term survival of mice bearing murine renal cancer as compared to treatment with either the flavonoid compound or rIL-2 alone.

The intravenous and/or intraperitoneal administration of therapeutic c=doses of flavonoid compound, ranging from about 110 mg/kg of body weight to about 500 mg/kg of body weight, resulted in potent augmentation of the rIL-2 in the spleen or liver. Peak levels of NK-mediated lysis were generally achieved by 24 hour post injection, with levels of NK activity decreasing to background by about day 6.

According to the present invention, the administration of the flavonoid compound in association with moderate doses of IL-2 is a more useful approach to the treatment of cancer than administration of high doses of IL-2 alone. The combination of the flavonoid compounds and rIL-2 is also effective in eradicating established experimental hepatic metastases, and the inclusion of adoptive immunotherapy in the treatment regimen does not further increase survival.

The mechanism by which the flavonoid compound and rIL-2 complement each other in the treatment of cancer is not known. The augmentation of NK activity by the flavonoid compound is an indirect effect, since this agent does not boost NK activity in mice or humans in vitro. Thus, it appears likely that the induction of NK activity, and perhaps the therapeutic effects thereof, are mediated by metabolites of the flavonoids or by cytokines induced by the flavonoids.

EXAMPLES

Example 1

| a) OXO-1-PHENYL-3-1H-NAPHTHO (2.1-b) PYRAN-5-ACETONITRILE | |
|---|---|
| $C_{21}H_{13}NO_2$ | MW = 311,344 |

A mixture of 8.2 g (0.0224 mole) of bromomethyl-5-phenyl-3-[1H]-naphtho(2.1-b)pyranon-1, of 4.9 g (0.031 mole) of tetraethylammonium cyanide in 250 ml of dichloroethane is stirred for 18 hours at room temperature. Evaporation is then carried out in a vacuum, the mixture is solidified using water, and the solid thus formed is filtered and dried. Weight obtained: 6.9 g (Yield: 98%); $PF_k$=260° C.; IR: $V_{c=o}$=7039 $cm^{-1}$, $V_{c=N}$=2160 and 2220 $cm^{-1}$.

OXO-1-PHENYL-3-(1H)-NAPHTHO(2.1-b)PYRAN-5-ACETIC ACID $C_{21}H_{14}O_4$ MW = 330.34 [Formula 1]

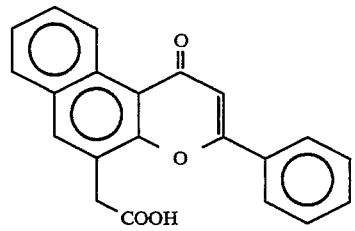

A mixture of 6.9 g (0.022 mole) of oxo-1-phenyl-3-[1H]-naphto(2.1-b)pyran-5-aceto-nitrile, 50 ml of acetic acid, 50 ml of water and 50 ml of $H_2SO_4$ in concentrated form is heated by reflux. The medium is then poured into water and frozen; the solid thus formed is centrifuged, dried, recrystallized in acetic acid. Weight obtained: 2.1 g (Yield: 28%); $PF_G$=291°-293° C.; IR: $V_{c=o}$ (acid)=1700 $cm^{-1}$, $V_{c=o}$ (pyrone)=1638 $cm^{-1}$; NMR (DMSO)δ in ppm in relation to TMS: 2H at 4.03 (s), 1H at 7.1 (s), 9H at 7.3 to 8.3 (m), 1H at 12.5 (exchangeable).

| | Elemental analysis | | |
|---|---|---|---|
| | C % | H % | O % |
| calculated | 76.35 | 4.27 | 19.37 |
| found | 73.85 | 4.01 | |

Using the same technique the following compounds are prepared:

OXO-4-PHENYL-2-4H-NAPHTHO(2.3-b)PYRAN-1-ACETIC ACID $C_{21}H_{14}O_4$ MW = 330.34 [Formula 2]

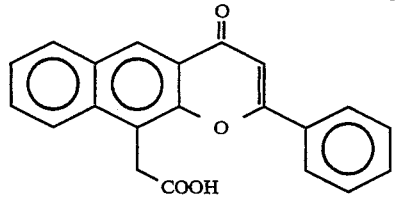

$PF_G$=276°-288° C.; IR: $V_{c=o}$ (acid)=1720 $cm^{-1}$, $V_{c=o}$ (pyrone)=7610 $cm^{-1}$; NMR (DMSO)δ in ppm in relation to TMS: 2H at 4.4 (s), 1H at 6.97 (s), 9H at 7.2 to 8.5 (m), 1H at 8.62 (s), 1H at 12.5 (exchangeable).

| | Elemental analysis | | |
|---|---|---|---|
| | C % | H % | O % |
| calculated | 76.39 | 4.27 | 19.38 |
| found | 79.89 | 4.39 | |

OXO-4-PHENYL-2-4H-NAPHTHO(1.2-b)PYRAN-10-ACETIC ACID $C_{21}H_{14}O_4$ MW = 330.34 [Formula 3]

-continued

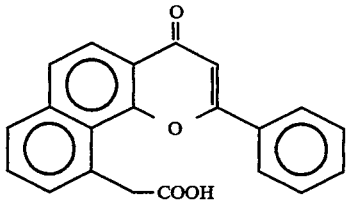

PF$_G$=259°-261° C., IR: $V_{c=o}$ (acid)=1710 cm$^{-1}$, $V_{c=o}$ pyrone)=7630 cm$^{-1}$; NMR (DMSO)δ in ppm in relation to TMS: 2H at 4.45(s), 1 H at 6.9 (s), 10H at 7.3 to 8.3 (m), 1H at 12.2 (exchangeable).

| | Elemental analysis | | |
|---|---|---|---|
| | C % | H % | O % |
| calculated | 76.39 | 4.27 | 19.38 |
| found | 76.24 | 4.07 | |

METHOXY-3-OXO-4-PHENYL-2H-(1)-BENZOPYRAN-8-ACETIC ACID $C_{18}H_{14}O_5$ MW = 310.292 [Formula 4]

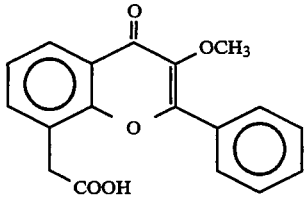

PF$_G$=187°−192° C.; IR $V_{c=o}$ (acid)=1720 cm$^{-1}$, $V_{c=o}$(pyrone)=1610 cm$^{-1}$; NMR (DMSO)δ in ppm in relation to TMS: 3H at 3.8 (s), 2H at 4 (s), 8H at 7.4 to 8.3 (m), 1H 11.9 (exchangeable).

| | Elemental analysis | | |
|---|---|---|---|
| | C % | H % | O % |
| calculated | 69.67 | 4.55 | 23.78 |
| found | 69.90 | 4.55 | |

METHOXY-5-OXO-4-PHENYL-2-4H-(1)-BENZOPYRAN-8-ACETIC ACID $C_{18}H_{14}O_5$ MW = 310.292 [Formula 5]

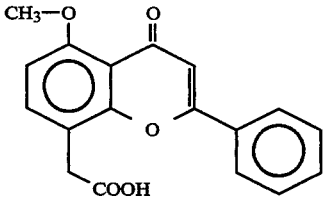

PF$_G$=245°−248° C.; IR $V_{c=o}$ (acid)=1720 cm$^{-1}$, $V_{c=o}$ (pyrone) 1640 cm$^{-1}$; NMR (DMSO)δ in ppm in relation to TMS: 5H at 4 (s), 1H at 7.2 (s), 7H at 7.7 to 8.7 (m), 1H at 12.2 (exchangeable).

| | Elemental analysis | | |
|---|---|---|---|
| | C % | H % | O % |
| calculated | 69.67 | 4.55 | 29.78 |
| found | 69.50 | 4.57 | |

(METHOXY-2-PHENYL)-2-OXO-4-4H-(1)BENZOPYRAN-8-ACETIC ACID $C_{18}H_{14}O_5$ MW = 310.292 [Formula 6]

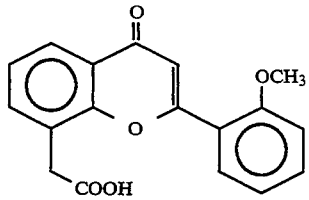

PF$_G$=203°-205° C.; IR $V_{c=o}$ (acid)=1730 cm$^{-1}$; $V_{c=o}$(pyrone)=1610 cm$^{-1}$; NMR (DMSO)δ in ppm in relation to TMS; 5H at 4 (s), 1H at 7 (s), 7H at 7.1 to 8.1 (m), 1H at 12.8 (exchangeable).

| | Elemental analysis | | |
|---|---|---|---|
| | C % | H % | O % |
| calculated | 69.67 | 4.55 | 25.78 |
| found | 69.72 | 4.39 | |

HYDROXY-3-OXO-4-PHENYL-2-4H-(1)-BENZOPYRAN-8-ACETIC ACID $C_{17}H_{12}O_3$ MW = 296.266 [Formula 7]

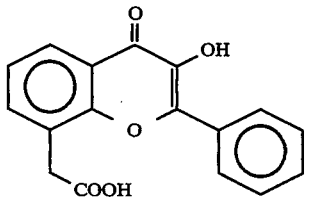

PF$_G$=221°-223° C.; IR $V_{c=o}$ (acid)=1700 cm$^{-1}$, $V_{c=o}$(pyrone)=1610 cm$^{-1}$; NMR (DMSO)δ in ppm in relation to the TMS; 2H at 4 (s), 8H) at 7.3-8.4 (m), 1H at 9.6 (exchangeable), 1H at 12.3 (exchangeable).

| | Elemental analysis | | |
|---|---|---|---|
| | C % | H % | O % |
| calculated | 68.92 | 4.08 | 27.00 |
| found | 68.86 | 4.01 | |

HYDROXY-5-OXO-4-PHENYL-2-4H-(1)-BENZOPYRAN-8-ACETIC ACID $C_{17}H_{12}O_5$ MW = 296.266 [Formula 8]

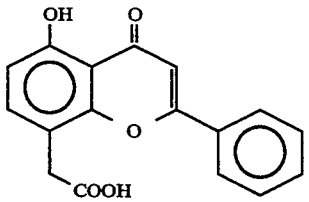

PF$_G$=233°-238° C.; IR $V_{c=o}$ (acid)=1700 cm$^{-1}$, $V_{c=o}$(pyrone)=1680 cm$^{-1}$; NMR (DMSO)δ in ppm in relation to TMS; 2H at 3.8 (s), 1H at 6.8 (d), 1H at 7.1 (s), 6H at 7.4 to 8.2 (m), 1H at 42.4 (exchangeable).

| | Elemental analysis | | |
|---|---|---|---|
| | C % | H % | O % |
| calculated | 68.92 | 4.08 | 27.00 |
| found | 68.85 | 4.22 | |

HYDROXY-7-OXO-4-PHENYL-2-4H-(1)-BENZOPYRAN-8-ACETIC ACID $C_{17}H_{12}O_5$ MW = 296.266 [Formula 9]

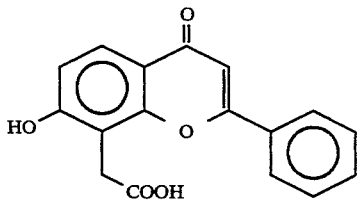

$PF_G$=227°-238° C.; IR $V_{c=o}$ (acid)=1700 $cm^{-1}$, $V_{c=o}$(pyrone)=1630 $cm^{-1}$; NMR (DMSO)δ in ppm in relation to TMS; 2H at 3.8 (s), 8H at 6.8 to 8.2 (m), 2H at 10.8 to 11.1 (exchangeable).

| | Elemental analysis | | |
|---|---|---|---|
| | C % | H % | O % |
| calculated | 68.92 | 4.08 | 27.00 |
| found | 68.92 | 4.00 | |

(HYDROXY-2-PHENYL)-2-OXO-4-4H-(1)-BENZOPYRAN-8-ACETIC ACID $C_{17}H_{12}O_3$ MW = 296.266 [Formula 10]

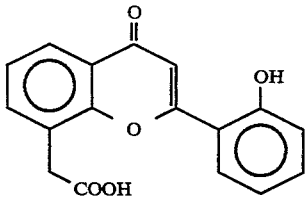

$PF_G$=288°-292° C.; IR $V_{c=o}$ (acid)=1700 $cm^{-1}$, $V_{c=o}$(pyrone)=1640 $cm^{-1}$; NMR (DMSO)δ in ppm in relation to TMS; 2H at 4 (s), 1H at 7 (S), 1H at 7 (s), 7H at 7.2 to 8.2 (m), 2H at 10.8 to 12.9 (exchangeable).

| | Elemental analysis | | |
|---|---|---|---|
| | C % | H % | O % |
| calculated | 68.92 | 4.08 | 27.00 |
| found | 68.75 | 3.88 | |

(HYDROXY-3-PHENYL)-2-OXO-4-4H-(1)-BENZOPYRAN-8-ACETIC ACID $C_{17}H_{12}O_5$ MW = 296.266 [Formula 11]

-continued

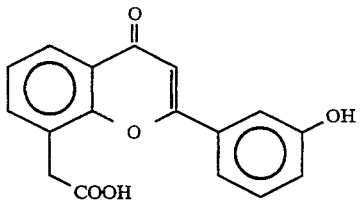

$PF_G$32 259°-288° C.; IR $V_{c=o}$ (acid)=1720 $cm^{-1}$, $V_{c=o}$(pyrone)=1630 $cm^{-1}$; NMR (DMSO)δ in ppm in relation to TMS; 2H at 4.1 (s), 1H at 7 (s), 7H at 7.1 to 8.2 (m), 1H at 10 at 10 (exchangeable), 1H at 12.8 (exchangeable).

| | Elemental analysis | | |
|---|---|---|---|
| | C % | H % | O % |
| calculated | 68.92 | 4.08 | 27.00 |
| found | 68.91 | 4.21 | |

(HYDROXY-4-PHENYL)-2-OXO-4-4H-(1)-BENZOPYRAN-8-ACETIC ACID $C_{17}H_{12}O_5$ MW = 296.266 [Formula 12]

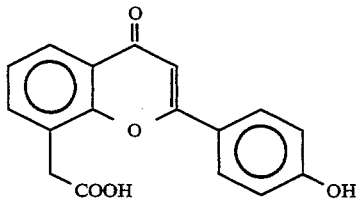

$PF_G$=261°-268° C.; IR $V_{c=o}$ (acid)=1690 $cm^{-1}$, Vc=0 (pyrone)=1620 $cm^{-1}$; NMR (DMSO)δ in ppm in relation to TMS; 2H at 3.8 (s), 8H at 6.7 to 8 (m), 1H at 10.3 (exchangeable), 1H at 12.2 (exchangeable).

| | Elemental analysis | | |
|---|---|---|---|
| | C % | H % | O % |
| calculated | 68.92 | 4.08 | 27.00 |
| found | 68.61 | 4.20 | |

CHLOROHYDRATE OF (DIETHYLAMINOETHOXY-3-PHENYL)-2-OXO-4-4H-BENZOPYRAN-8-ACETIC ACID $C_{23}H_{26}ClNO_3$ MW = 431.903 [Formula 13]

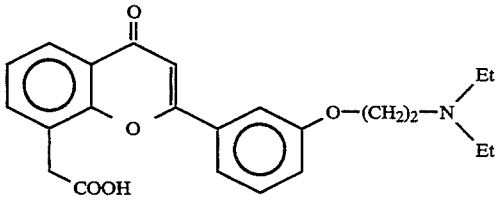

$PF_G$=176°-179° C.; IR $V_{c=o}$ (acid)=1720 $cm^{-1}$, $V_{c=o}$(pyrone)=1640 $cm^{-1}$; NMR (DMSO)δ in ppm in relation to TMS; 3H at 1.4 (t), 11H at 3 to 4.6 (m, of which 1H is exchangeable), 1H at 7.1 (s), 6H at 7.2 to 8.1 (m), 1H at 13.2 (exchangeable).

| | Elemental analysis | | | | |
|---|---|---|---|---|---|
| | C % | H % | Cl % | N % | O % |
| calculated | 63.96 | 6.07 | 8.21 | 3.24 | 18.32 |
| found | 63.69 | 5.88 | 8.09 | 3.01 | |

(PHENOXY-2-PHENYL-2-OXO-4-4H-(1)-BENZOPYRAN-8-ACETIC ACID $C_{23}H_{16}O_3$ MW = 372.38 [Formula 14]

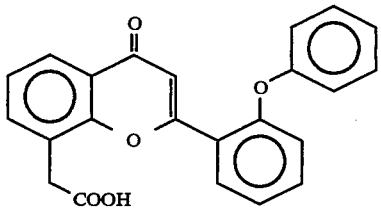

$PF_G$=218°-220° C.; IR $V_{c=o}$ (acid)=1680 $cm^{-1}$, $V_{c=o}$(pyrone)=1640 $cm^{-1}$; NMR (DMSO)δ in ppm in relation to TMS; 2H at 3.8 (s), 13H at 6.8 to 8 (m), 1H at 12.6 (exchangeable)

| | Elemental analysis | | |
|---|---|---|---|
| | C % | H % | O % |
| calculated | 74.19 | 4.33 | 21.48 |
| found | 73.88 | 4.56 | |

FLUORO-6-OXO-4-PHENYL-2-4H-(1)-BENZOPYRAN-8-ACETIC ACID $C_{17}H_{11}FO_4$ MW = 298.26 [Formula 15]

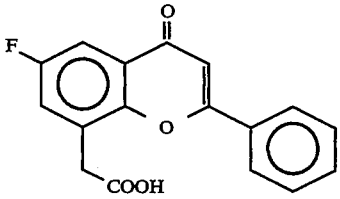

$PF_G$=225°-239° C.; IR $V_{c=o}$ (acid)=1720 $cm^{-1}$, $V_{c=o}$(pyrone)=1640 $cm^{-1}$; NMR (DMSO)δ in ppm in relation to TMS; 3H at 3 to 4 (m, of which 1H is exchangeable), 1H at 7 (s), 7H at 7, 1H at 8.4 (m).

| | Elemental analysis | | | |
|---|---|---|---|---|
| | C % | H % | F % | O % |
| calculated | 68.49 | 3.72 | 6.37 | 21.46 |
| found | 68.42 | 3.92 | 6.28 | |

(FLUORO-6-PHENYL)-2-OXO-4-4H-(1)-BENZOPYRAN-8-ACETIC ACID $C_{17}H_{11}FO_4$ MW = 298.26 [Formula 16]

-continued

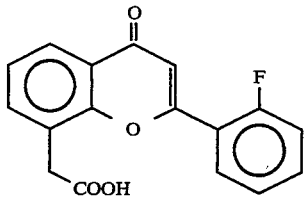

$PF_G$=193°-199° C.; IR $V_{c=o}$ (acid)=1720 $cm^{-1}$, $V_{c=o}$(pyrone)=1610 $cm^{-1}$; NMR (DMSO)δ in ppm in relation to TMS; 2H at 4 (s), 1H at 6.7 (s), 7H at 7.2 to 8.4 (m), 1H at 12.5 (exchangeable).

| | Elemental analysis | | | |
|---|---|---|---|---|
| | C % | H % | F % | O % |
| calculated | 68.49 | 3.72 | 6.37 | 21.46 |
| found | 68.42 | 3.92 | 6.28 | |

(FLUORO-6-PHENYL)-2-OXO-4H-(1)-BENZOPYRAN-8-ACETIC ACID $C_{17}H_{11}FO_4$ MW = 298.26 [Formula 17]

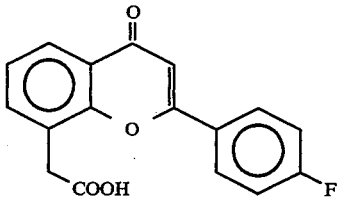

$PF_G$=215°-217° C.; IR $V_{c=o}$ (acid)=1720 $cm^{-1}$, $V_{c=o}$ (pyrone)=1640 $cm^{-1}$; NMR ($CF_3COOD$)δ in ppm in relation to TMS; 2H at 4 (s), 8H at 7 to 9 (m).

| | Elemental analysis | | | |
|---|---|---|---|---|
| | C % | H % | F % | O % |
| calculated: | 67.49 | 3.72 | 6.37 | 24.46 |
| found: | 68.54 | 3.80 | 6.33 | |

(FLUORO-3-PHENYL)-2-OXO-4-4H-(1)-BENZOPYRAN-8-ACETIC ACID $C_{17}H_{11}FO_4$ MW = 297.26 [Formula 18]

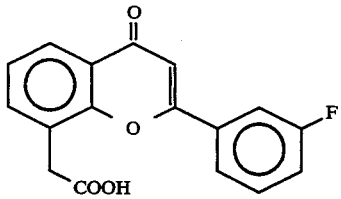

$PF_G$=201°-203° C.; IR $V_{c=o}$ (acid)=1700 $cm^{-1}$, $V_{c=o}$(pyrone)=1640 $cm^{-1}$; NMR (DMSO)δ in ppm in relation to TMS; 2H at 4 (s), 1H at 7.1 (s), 7H at 7.2 to 8 (m), 1H at 12.6 (exchangeable).

| | Elemental analysis | | | |
|---|---|---|---|---|
| | C % | H % | F % | O % |
| calculated: | 68.49 | 3.72 | 6.37 | 21.46 |

-continued

| | Elemental analysis | | | |
|---|---|---|---|---|
| | C % | H % | F % | O % |
| found: | 68.20 | 3.69 | 6.28 | |

(PHENYL-4-PHENYL)2-OXO-4-4H-(1)-BENZOPYRAN-8-ACETIC ACID $C_{23}H_{16}O_4$ MW = 356.36 [Formula 19]

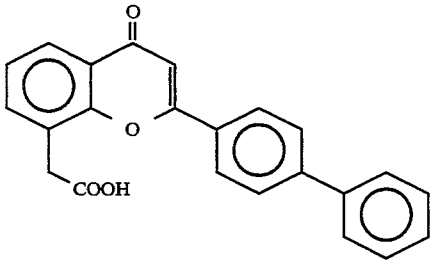

$PF_G$=229°-231° C.; IR $V_{c=o}$ (acid)=1710 $cm^{-1}$, $V_{c=o}$(pyrone)=1620 $cm^{-1}$; NMR (DMSO)δ in ppm in relation to TMS; 2H at 4 (s), 1H at 7 (s), 12H at 7.2 to 8.4 (m), 1H at 12.6 (exchangeable).

| | Elemental analysis | | |
|---|---|---|---|
| | C % | H % | O % |
| calculated: | 77.51 | 4.53 | 17.96 |
| found: | 77.42 | 4.41 | |

(CHLORO-4-PHENYL)-2-OXO-4-4H-(1)-BENZOPYRAN-8-ACETIC ACID $C_{17}H_{11}ClO_4$ MW = 314.71 [Formula 20]

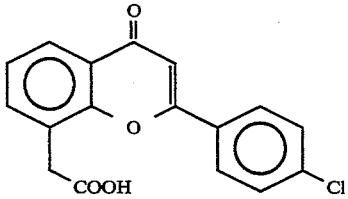

$PF_G$=238°-242° C.; IR $V_{c=o}$ (acid)=1720 $cm^{-1}$, $V_{c=o}$(pyrone)=1620 $cm^{-1}$; NMR (DMSO)δ in ppm in relation to TMS; 2H at 4 (s), 1H at 7 (s), 7H at 7.2 to 8.2 (m), 1H at 12.5 (exchangeable).

| | Elemental analysis | | | |
|---|---|---|---|---|
| | C % | H % | Cl % | O % |
| calculated: | 64.87 | 3.52 | 11.27 | 20.34 |
| found: | 64.83 | 3.37 | 11.55 | |

(CARBOXY-4-PHENYL)-2-OXO-4-4H-(1)-BENZOPYRAN-8-ACETIC ACID $C_{18}H_{12}O_6$ MW = 324.27 [Formula 21]

-continued

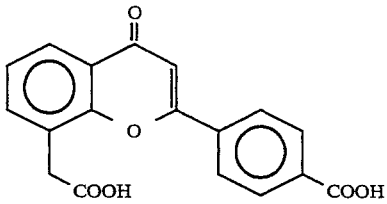

$PF_G$=312°-314° C.; IR $V_{c=o}$ (acid)=1700-1720 $cm^{-1}$, $V_{c=o}$(pyrone)=1640 $cm^{-1}$.

| | Elemental analysis | | |
|---|---|---|---|
| | C % | H % | O % |
| calculated: | 66.67 | 3.73 | 29.69 |
| found: | 66.76 | 3.73 | |

(FLUORO-2-PHENYL)-4-PHENYL)-2-OXO-4-4H-(1) BENZOPYRAN-8-ACETIC ACID $C_{23}H_{15}FO_4$ MW = 374.35 [Formula 22]

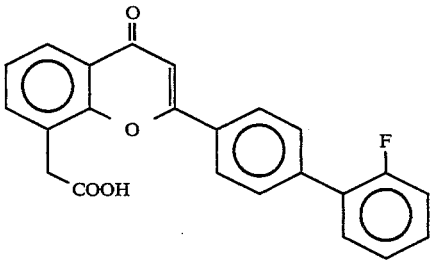

$PF_G$=226°-228° C.; IR $V_{c=o}$ (acid)=1720 $cm^{-1}$, $V_{c=o}$(pyrone)=1630 $cm^{-1}$; NMR (DMSO)δ in ppm in relation to TMS; 2H at 4 (S), 12H at 7 to 8.4 (m), 1H to 12.8 (exchangeable).

| | Elemental analysis | | | |
|---|---|---|---|---|
| | C % | H % | F % | O % |
| calculated: | 73.79 | 4.04 | 5.08 | 17.10 |
| found: | 73.80 | 4.14 | 4.87 | |

(NITRO-2-PHENYL)-2-OXO-4-4H-(1)-BENZOPYRAN-8-ACETIC ACID $C_{17}H_{11}NO_4$ MW = 325.28 [Formula 23]

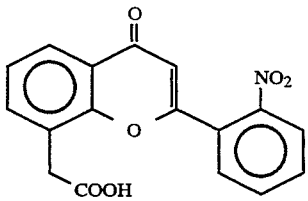

$PF_G$=180°-182° C.; IR $V_{C=o}$ (acid)=1700 $cm^{-1}$, $V_{c=o}$(pyrone)=1640 $cm^{-1}$; NMR (DMSO)δ in ppm in relation to TMS; 2H at 4 (s), 1H at 6.8 (s), 7H at 7.3 to 8.3 (m), 1H at 12.8 (exchangeable).

| | Elemental analysis | | | |
|---|---|---|---|---|
| | C % | H % | N % | O % |
| calculated: | 62.77 | 3.41 | 4.31 | 29.51 |

-continued

| | Elemental analysis | | | |
|---|---|---|---|---|
| | C % | H % | N % | O % |
| found: | 62.82 | 3.47 | 4.20 | |

(NITRO-3-PHENYL)-2-OXO-4-4H-(1)-BENZOPYRAN-8-ACETIC ACID $C_{17}H_{11}NO_6$ MW = 325.28 [Formula 24]

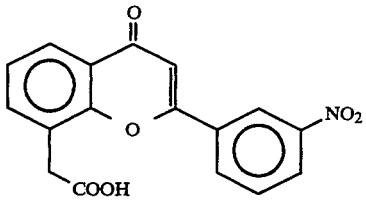

$PF_G$=203°-208° C.; IR $V_{c=o}$ (acid)=1720 $cm^{-1}$, $V_{c=o}$(pyrone)=1630 $cm^{-1}$; NMR (DMSO)δ in ppm in relation to TMS; 2H at 4 (s), 1H at 7.3 (s), 7H at 7.4 to 9 (m), 1H at 12.6 (exchangeable).

| | Elemental analysis | | | |
|---|---|---|---|---|
| | C % | H % | N % | O % |
| calculated: | 62.77 | 3.41 | 4.31 | 29.51 |
| found: | 62.49 | 3.40 | 4.31 | |

(NITRO-4-PHENYL)-2-OXO-4-4H-(1)-BENZOPYRAN-8-ACETIC ACID $C_{17}H_{11}NO_6$ MW = 325.28 [Formula 25]

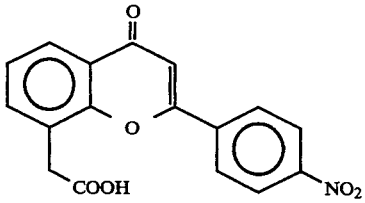

$PF_G$=242°-244° C.; IR $V_{c=o}$ (acid)=1720 $cm^{-1}$, $V_{c=o}$(pyrone)=1620 $cm^{-1}$; NMR (DMSO)δ in ppm in relation to TMS; 2H at 4 (s), 1H at 7 (s), 7H at 7.2 to 8.3 (m), 1H at 12.5 (exchangeable).

| | Elemental analysis | | | |
|---|---|---|---|---|
| | C % | H % | N % | O % |
| calculated: | 62.77 | 3.41 | 4.31 | 29.51 |
| found: | 62.92 | 3.38 | 4.28 | |

(AMINO-3-PHENYL)-2-OXO-4-4H-(1)-BENZOPYRAN-8-ACETIC ACID $C_{17}H_{13}NO_4$ MW = 295.28 [Formula 26]

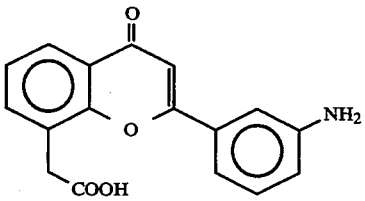

$PF_G$=227°-139° C.; IR $V_{c=o}$ (acid)=1720 $cm^{-1}$, $V_{c=o}$(pyrone)=1630 $cm^{-1}$; NMR (DMSO)δ in ppm in relation to TMS; 2H at 4 (s), 9H at 6.8 to 8 (m), 1H at 12.6 (exchangeable).

| | Elemental analysis | | | |
|---|---|---|---|---|
| | C % | H % | N % | O % |
| calculated: | 69.14 | 4.44 | 4.74 | 21.67 |
| found: | 69.20 | 4.70 | 4.94 | |

(AMINO-4-PHENYL)-2-OXO-4-4H-(1)-BENZOPYRAN-8-ACETIC ACID $C_{17}H_{13}NO_4$ MW = 295.28 [Formula 27]

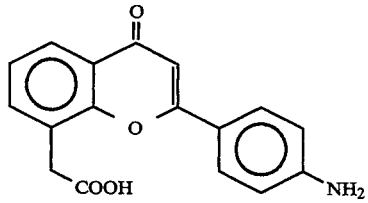

$PF_G$=189° C.; IR $V_{c=o}$ (acid)=1700 $cm^{-1}$, $V_{c=o}$ (pyrone)=1620 $cm^{-1}$.

| | Elemental analysis | | | |
|---|---|---|---|---|
| | C % | H % | N % | O % |
| calculated: | 69.14 | 4.44 | 4.74 | 21.67 |
| found: | 69.00 | 4.48 | 4.66 | |

OXO-4-PHENYL-2-4H-(1)-BENZOPYRAN-5-ACETIC ACID $C_{17}H_{12}O_4$ MW = 280.28 [Formula 28]

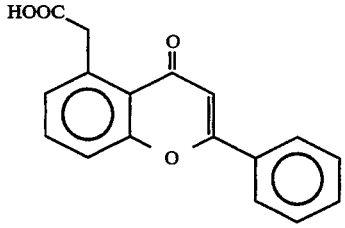

$PF_G$=240°-242° C.; IR $V_{c=o}$ (acid)=1740 $cm^{-1}$, $V_{c=o}$(pyrone)=1640 $cm^{-1}$; NMR (DMSO)δ in ppm in relation to TMS; 2H at 4 (s), 1H at 7 (s), 8H at 7.2 to 8.4 (m), 1H at 12.6 (exchangeable).

| | Elemental analysis | | |
|---|---|---|---|
| | C % | H % | O % |
| calculated: | 72.85 | 4.32 | 22.83 |
| found: | 73.00 | 4.16 | |

OXO-4-PHENYL-2-4H-(1) BENZOPYRAN-7-ACETIC ACID $C_{17}H_{12}O_4$ MW = 280.28 [Formula 29]

-continued

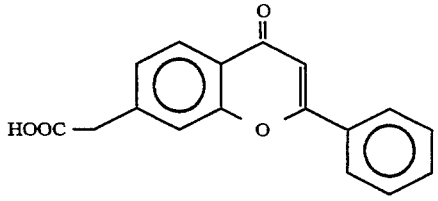

PF$_G$=237°-239° C.; IR $V_{c=o}$ (acid)=1740 cm$^{-1}$, $V_{c=o}$(pyrone)=1620 cm$^{-1}$; NMR (DMSO)δ in ppm in relation to TMS; 2H at 3.7 (s), 1H at 6.8 (s), 7H at 7.2 to 8 (m), 1H at 12.5 (exchangeable).

| | Elemental analysis | | |
|---|---|---|---|
| | C % | H % | O % |
| calculated: | 72.85 | 4.32 | 22.83 |
| found: | 72.73 | 4.33 | |

TRIFLUOROMETHYL-2-OXO-4-4H-(1)-BENZOPYRAN-8-ACETIC ACID $C_{12}H_7F_3O_4$ MW = 272.17 [Formula 30]

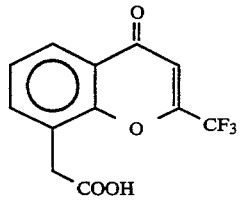

PF$_G$=141°-143° C.; IR $V_{c=0}$ (acid)=1700 cm$^{-1}$, $V_{c=o}$ (pyrone)=1650 cm$^{-1}$.

| | Elemental analysis | | | |
|---|---|---|---|---|
| | C % | H % | F % | O % |
| calculated: | 52.95 | 2.59 | 20.94 | 23.52 |
| found: | 52.72 | 2.64 | 20.35 | |

OXO-4-PHENYL-2-4H-(1)-BENZOTHIOPYRAN-8-ACETIC ACID $C_{17}H_{12}O_3S$ MW = 296.34 [Formula 31]

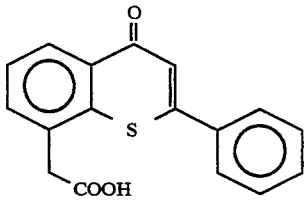

PF$_G$=198°-200° C.; IR $V_{c=o}$ (acid)=1720 cm$^{-1}$, $V_{c=o}$(pyrone)=1610 cm$^{-1}$; NMR (DMSO)δ in ppm in relation to TMS; 2H at 4 (s), 1H at 7.3 (s), 7H at 7.3 to 8.4 (m), 1H at 12.5 (exchangeable).

| | Elemental analysis | | | |
|---|---|---|---|---|
| | C % | H % | O % | S % |
| calculated: | 68.40 | 4.08 | 16.20 | 10.82 |
| found: | 69.04 | 4.29 | | 11.04 |

OXO-4-PHENYL-2-4H-(1)-BENZOTHIOPYRAN-8-ACETIC ACID-S,S-DIOXIDE $C_{17}H_{12}O_5S$ MW = 328.34 [Formula 32]

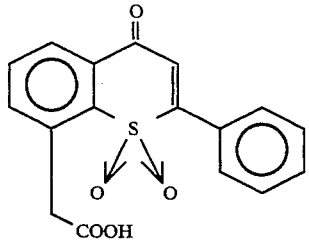

PF$_G$=184°-187° C.; IR $V_{c=o}$ (acid)=1700 cm$^{-1}$, $V_{c=o}$(pyrone)=1660 cm$^{-1}$; NMR (DMSO)δ in ppm in relation to TMS; 2H at 4 (s), 1H at 7 (s), 7H at 7.2 to 8.2 (m), 1H at 12.6 (exchangeable).

| | Elemental analysis | | | |
|---|---|---|---|---|
| | C % | H % | O % | S % |
| calculated: | 62.18 | 3.68 | 24.36 | 9.77 |
| found: | 62.29 | 3.68 | | 9.65 |

OXO-4-PHENYL-2-DIHYDRO-1-4-QUINOLINE-8-ACETIC ACID $C_{17}H_{13}NO_3$ MW = 279.29 [Formula 33]

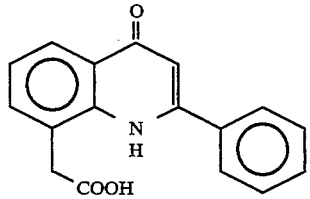

PF$_G$=236°-238° C.; IR $V_{c=o}$ (acid)=1680 cm$^{-1}$, $V_{c=o}$(pyrone)=1620 cm$^{-1}$; NMR (DMSO)δ in ppm in relation to TMS; 2H at 4 (s), 8H at 7 to 8.3 (m), 1H at 8.5 (exchangeable).

| | Elemental analysis | | | |
|---|---|---|---|---|
| | C % | H % | N % | O % |
| calculated: | 73.11 | 4.69 | 5.01 | 17.18 |
| found: | 73.10 | 4.62 | 5.04 | |

OXO-4-PHENYL-2-4H-(1)-BENZOSELENOPYRAN-8-ACETIC ACID $C_{17}H_{12}O_3Se$ MW = 343.24 [Formula 34]

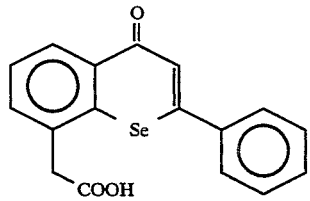

PF$_G$=182°-184° C.; IR $V_{c=o}$ (acid)=1700 cm$^{-1}$, $V_{c=o}$(pyrone)=1600 cm$^{-1}$; NMR (DMSO)δ in ppm in relation to TMS; 2H at 4 (s), 8H at 7.4 to 8.6 (m), 1H at 12.5 (exchangeable).

| | Elemental analysis | | | |
|---|---|---|---|---|
| | C % | H % | O % | Se % |
| calculated: | 59.49 | 3.52 | 13.98 | 23.00 |
| found: | 59.30 | 3.26 | | 22.91 |

OXO-7-7H-BENZO(c) XANTHENYL-11-ACETIC ACID $C_{19}H_{12}O_4$ MW = 304.31 [Formula 35]

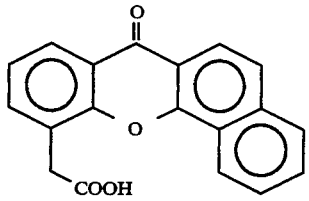

$PF_G$=270°-272° C.; IR $V_{c=o}$ (acid)=1720 $cm^{-1}$, $V_{c=o}$(pyrone)=1620 $cm^{-1}$; NMR (DMSO)δ in ppm in relation to TMS; 2H at 4 (s), 9H at 7.4 to 9.2 (m), 1H at 12.5 (exchangeable).

| | Elemental analysis | | |
|---|---|---|---|
| | C% | H% | O% |
| calculated: | 74.99 | 3.97 | 21.03 |
| found: | 74.34 | 3.93 | |

OXO-4-7-7H-DIBENZO(c,h) XANTHENYL-1-ACETIC ACID $C_{23}H_{14}O_4$ MW = 354.37 [Formula 36]

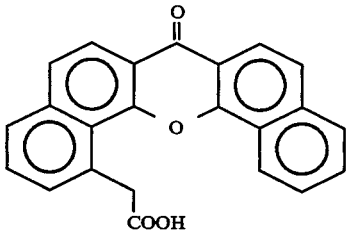

$PF_G$=276°-278° C.; IR $V_{c=o}$ (acid)=1700 $cm^{-1}$, $V_{c=o}$(pyrone)=1620 $cm^{-1}$; NMR (DMSO)δ in ppm in relation to TMS; 2H at 4 (s), 11H at 7.4 to 8.8 (m), 1H at 12.5 (exchangeable).

| | Elemental analysis | | |
|---|---|---|---|
| | C% | H% | O% |
| calculated: | 77.96 | 3.98 | 18.06 |
| found: | 77.94 | 3.97 | |

CARBOXYMETHYL-4-PHENYL)-2-4H-(1) BENZOPYRANONE-4

$C_{17}H_{12}O_4$ MW = 280.17 [Formula 37]

-continued

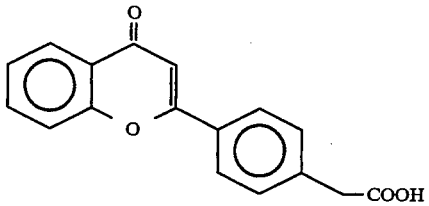

$PF_G$32 204°-C.; IR $V_{c=o}$ (acid)=1720 $cm^{-1}$, $V_{c=o}$ (pyrone)=1640 $cm^{-1}$.

| | Elemental analysis | | |
|---|---|---|---|
| | C% | H% | O% |
| calculated: | 72.84 | 4.32 | 22.84 |
| found: | 72.08 | 4.33 | |

(CARBOXYMETHYL-3-PHENYL)-2-4H-(1) BENZOPYRANONE-4

$C_{17}H_{12}O_4$ MW = 280.27 [Formula 38]

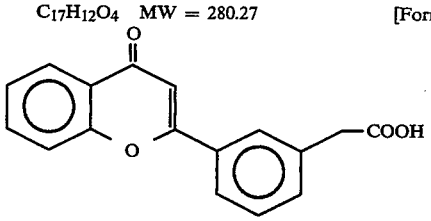

$PF_G$=281°-183° C.; IR $V_{c=o}$ (acid)=1720 $cm^{-1}$, $V_{c=o}$(pyrone)=1620 $cm^{-1}$; NMR (DMSO)δ in ppm in relation to TMS; 2H at 3.8 (s), 1H at 7 (s), 8H at 7.4 to 8.2 (m), 1H at 12.4 (exchangeable).

| | Elemental analysis | | |
|---|---|---|---|
| | C% | H% | O% |
| calculated: | 72.84 | 4.32 | 22.84 |
| found: | 73.08 | 4.41 | |

(CARBOXYMETHYL-2-PHENYL)-2-4H-(1) BENZOPYRANONE-4

$C_{17}H_{12}O_4$ MW = 280.27 [Formula 39]

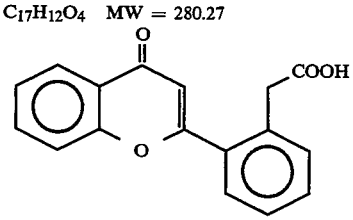

$PF_G$=179°-181° C.; IR $V_{c=o}$ (acid)=1730 $cm^{-1}$, $V_{c=o}$(pyrone)=1630 $cm^{-1}$; NMR (DMSO)δ in ppm in relatioo to TMS; 2H at 3.9 (s), 1H at 6.6 (s), 8H at 7.2 to 8.2 (m), 1H at 12.4 (exchangeable).

| | Elemental analysis | | |
|---|---|---|---|
| | C% | H% | O% |
| calculated: | 72.84 | 4.32 | 22.84 |
| found: | 73.79 | 4.34 | |

((OXO-4-PHENYL-2-4H-(1) BENZOPYRAN-8-YL) METHYL)

-continued

PHOSPHONATE OF DIETHYL $C_{20}H_{21}O_5P$ MW = 372.39 [Formula 40]

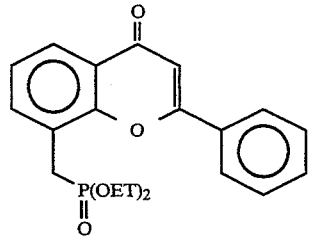

$PF_G$=107°-109° C.; IR $V_{c=o}$ (pyrone)=1640 $cm^{-1}$; NMR ($CDCl_3$)δ in ppm in relation to TMS; 6H at 1.2 (d), 2H at 3.57 (d), 4H at 3.7 to 4.4 (m), 1H at 6.85 (s), 8H at 7.2 to 8.4 (m).

| | Elemental analysis | | | |
|---|---|---|---|---|
| | C% | H% | O% | P% |
| calculated: | 64.51 | 5.69 | 21.48 | 8.32 |
| found: | 64.59 | 5.67 | | 8.17 |

((OXO-4-PHENYL-2-4H-(1) BENZOPYRAN-8-YL) METHYL) PHOSPHONIC ACID $C_{16}H_{13}O_5$ MW = 316.24 [Formula 41]

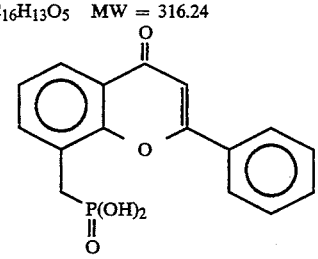

$PF_G$=331°-334° C.; IR V OH=3400 to 2200 $cm^{-1}$, $V_{c=o}$(pyrone)=1620 $cm^{-1}$; NMR (DMSO)δ in ppm in relation to TMS; 2H at 3.45 (d), 1H at 7.03 (s), 8H at 7.2 to 8.4 (m), 2H at 9.7 (exchangeable).

| | Elemental analysis | | | |
|---|---|---|---|---|
| | C% | H% | O% | P% |
| calculated: | 60.76 | 4.14 | 29.30 | 9.80 |
| found: | 60.77 | 4.17 | | 9.83 |

Example 2

(PHENYL-2-OXO-4-4H-(1) BENZOPYRAN-8-YL)-2-ACRYLIC ACID $C_{18}H_{12}O_4$ MW = 292.27 [Formula 42]

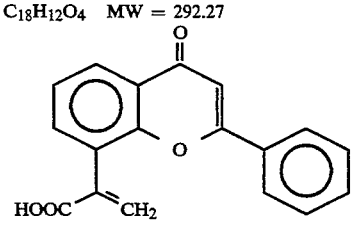

8.4 g (0.03 mole) of oxo-4-phenyl-2-4H-{4}-benzopyran-8acetic and 81 ml of N,N,N',N' tetramethyldiaminomethane are mixed. 81 ml acetic acid are then added to the reaction mixture cooled in an ice bath. The temperature rises to 65° C., then falls to 20° C. Stirring continues for one (1) hour, then the mixture is poured into water. The solid formed is centrifuged, dried, and recrystallized in acetic acid. Weight obtained: 3.4 g (yield: 38.6%); $PF_G$=240°-247° C.; IR $V_{c=o}$ (acid=1689 $cm^{-1}$, $V_{c=o}$ (pyrone)=1620 $cm^{-1}$; NMR (DMSO)δ in ppm in relation to TMS; 2H at 6.3 (d), 1H at 7 (s), 8H at 7.3 to 8.2 (m), 1H at 13 (exchangeable).

| | Elemental analysis | | |
|---|---|---|---|
| | C% | H% | O% |
| calculated: | 73.96 | 4.14 | 21.90 |
| found: | 74.21 | 4.05 | |

Example 3

PHENYL-3-(PHENYL-2-OXO-4-4H-[1]BENZOPYRAN-8-YL)-2-ACRYLIC ACID $C_{24}H_{16}O_4$ MW = 368.36 [Formula 43]

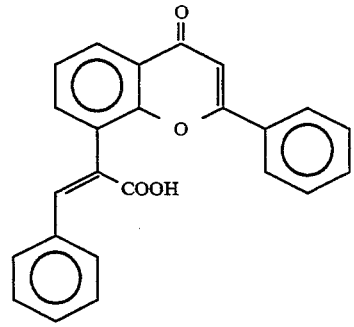

A mixture of 9.2 g (0.087 mole) of benzaldehyde, 16.8 g (0.06 mole) of oxo-4-phenyl-2-4H-[1]-benzopyranacetic acid, 30.9 ml of acetic anhydride, and 8.32 ml of triethylamine is refluxed for ten (10) minutes. The mixture is then poured into 30 ml of water. The precipitate formed centrifuged, dired and recrystallized in acetic acid. Weight obtained: 9.8 g (yield: 44.3%); $PF_G$=215°-220° C.; IR $V_{c=o}$ (acid)=1680 $cm^{-1}$, $V_{c=o}$ (pyrone)=1630 $cm^{-1}$; NMR (DMSO)δ in ppm in relation to TMS; 15H at 6.8 (m), 1H at 12.5 (exchangeable).

| | Elemental analysis | | |
|---|---|---|---|
| | C% | H% | O% |
| calculated: | 78.25 | 4.39 | 17.31 |
| found: | 77.90 | 4.11 | |

Using the same technique, the following compounds were prepared:

(BROMO-2-PHENYL)-3-(PHENYL-2-OXO-4-4H-[1] BENZOPYRAN-8-YL)-3-ACRYLIC ACID $C_{24}H_{15}BrO_4$ MW = 447.27 [Formula 44]

-continued

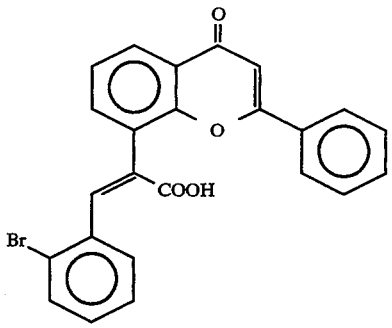

$PF_G$=217°-219° C.; IR $V_{c=o}$ (acid)=1680 $cm^{-1}$, $V_{c=o}$(pyrone)=1640 $cm^{-1}$; NMR (DMSO)δ in ppm in relation to TMS; 14H at 6.8 to 8.1 (m), 1H at 12.8 (exchangeable).

| | Elemental analysis | | | |
|---|---|---|---|---|
| | C% | H% | Br% | O% |
| calculated: | 64.44 | 3.38 | 17.87 | 14.31 |
| found: | 64.29 | 3.37 | 17.58 | |

(PYRIDINYL-4)-3-(PHENYL-2-OXO-4-4H-[1] BENZOPYRAN-8-YL)-3-ACRYLIC ACID $C_{23}H_{15}NO_4$ MW = 369.36 [Formula 45]

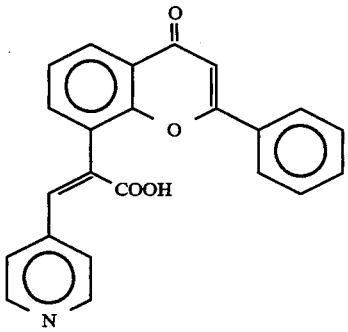

$PF_G$=272°-283° C.; IR $V_{c=o}$ (acid)=1700 $cm^{-1}$, $V_{c=o}$(pyrone)=1640 $cm^{-1}$; NMR (DMSO)δ in ppm in relation to TMS; 14H at 6.8 to 8.4 (m), 1H at 12.8 (exchangeable).

| | Elemental analysis | | | |
|---|---|---|---|---|
| | C% | H% | N% | O% |
| calculated: | 74.79 | 4.09 | 3.79 | 17.33 |
| found: | 74.54 | 4.00 | 3.79 | |

(PYRIDINYL-3)-3-(PHENYL-2-OXO-4-4H-[1] BENZOPYRAN-3-ACRYLIC ACID $C_{23}H_{15}NO_4$ MW = 369.36 [Formula 46]

-continued

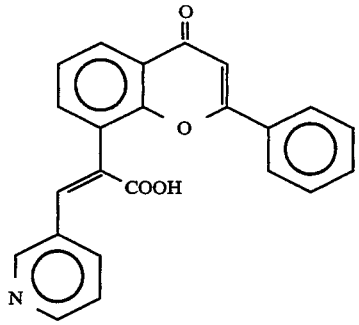

$PF_G$=118°-124° C.; IR $V_{c=o}$ (acid)=1720 $cm^{-1}$, $V_{c=o}$(pyrone)=1630 $cm^{-1}$; NMR (DMSO)δ in ppm in relation to TMS; 14H at 7 to 8.5 (m), 12.5 (exchangeable).

| | Elemental analysis | | | |
|---|---|---|---|---|
| | C% | H% | N% | O% |
| calculated: | 74.79 | 4.09 | 3.79 | 17.33 |
| found: | 74.36 | 4.09 | 3.50 | |

Example 4

CHLOROHYDRATE OF [(METHYL-4-PIPERAZINYL) METHYL]-8-PHENYL-2-4H-[1] BENZOPYRANONE-4

$C_{21}H_{23}ClN_2O_2$ MW = 370.87 [Formula 47]

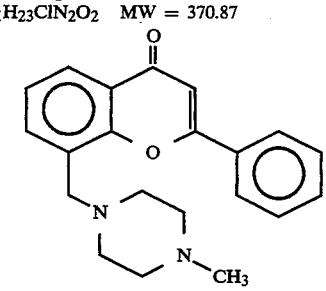

18.9 g (0.06 mole) of Bromomethyl-8-oxo-4-phenyl-2-4H-[1] Benzopyranone, 6.57 g (0.066 mole) of N-methyl piperazine, and 8.3 g (0.06 mole) of potassium carbonate in 200 ml of toluene are refluxed for 8 hours. Insolubles are filtred, and the solvent is evaporated in a vacuum. The solid obtained is recrystallized in hexane. Weight obtained: 9.69 g. $PF_G$=139° C.; IR $V_{c=o}$ (pyrone)=1640 $cm^{-1}$. Using an HCl treatment in $CHCl_3$, the chlorohydrate is obtained: $PF_G$=244°-246° C.

| | Elemental analysis | | | | |
|---|---|---|---|---|---|
| | C% | H% | Cl% | N% | O% |
| calculated: | 68.00 | 6.25 | 9.56 | 7.56 | 8.63 |
| found: | 68.34 | 5.86 | 9.80 | 7.61 | |

Using the same technique, the following compounds were prepared:

BROMOHYDRATE OF N[IMIDAZOLINYL-2], N [(OXO-4-PHENYL-2-4H-[1] BENZOPYRAN-8-YL) METHYL]-DICHLORO-2-6-ANILINE $C_{25}H_{20}BrCl_2N_3O_2$ MW = 545.26 [Formula 48]

-continued

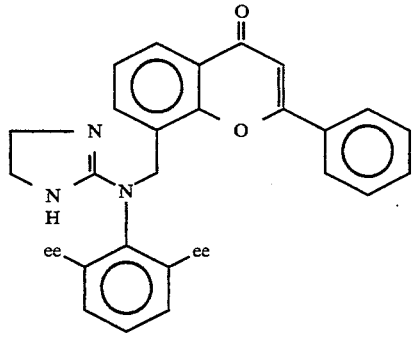

PF$_G$=289°-290° C.; IR $V_{c=o}$ (pyrone)=1640 cm$^{-1}$; V NH=3000-3200 cm$^{-1}$; NMR (DMSO)δ in ppm in relation to TMS; 4H at 3.4 (s), 2H at 5.5 (s), 1H at 7 (s), 11H at 7.2 to 8.3 (m), 2H at 8.5 to 9.5 (exchangeable).

| | Elemental analysis | | | | | |
|---|---|---|---|---|---|---|
| | C% | H% | Br% | Cl% | N% | O% |
| calculated: | 55.06 | 3.70 | 14.66 | 13.00 | 7.71 | 5.87 |
| found: | 55.14 | 3.63 | 14.56 | 13.09 | 7.07 | |

[(OXO-4-PHENYL-2-4H-(1) BENZOPYRAN-8-YL) METHYL AMINO]-4-BENZOIC ACID $C_{23}H_{17}NO_4$ MW = 371.396 [Formula 49]

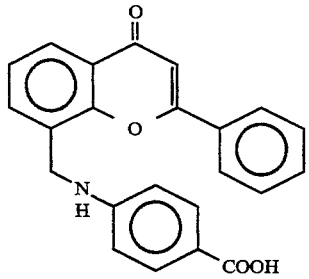

PF$_G$=269°-271° C.; IR $V_{c=o}$ (acid)=1710 cm$^{-1}$, $V_{c=o}$ (pyrone)=1640 cm$^{-1}$; NMR (DMSO)δ in ppm in relation to TMS; 2H at 4.8 (m), 13H at 6.9 to 8.27 (m), 1H at 12.6 (exchangeable).

| | Elemental analysis | | | |
|---|---|---|---|---|
| | C% | H% | N% | O% |
| calculated: | 74.38 | 4.61 | 3.77 | 17.24 |
| found: | 74.08 | 4.59 | 3.91 | |

N-[(OXO-4-PHENYL-2-4H-(1) BENZOPYRAN-8-YL) METHYL] N-METHYL, AMINO-4-BENZOIC ACID $C_{24}H_{19}NO_4$ MW = 385.424 [Formula 50]

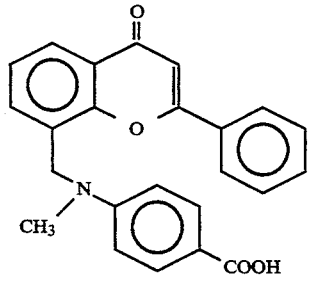

PF$_G$=260°-262° C.; IR $V_{c=o}$ (acid)=1710 cm$^{-1}$, $V_{c=o}$ (pyrone)=1640 cm$^{-1}$; NMR (DMSO)δ in ppm in relation to TMS; 3H at 3.2 (s), 2H at 5 (s), 13H at 6.8 to 8.4 (m), 1H at 12.6 (exchangeable).

| | Elemental analysis | | | |
|---|---|---|---|---|
| | C% | H% | N% | O% |
| calculated: | 74.79 | 4.97 | 3.63 | 16.60 |
| found: | 74.51 | 4.81 | 3.47 | |

[(OXO-4-PHENYL-2-4H-[1] BENZOPYRAN-8-YL) METHYLAMINO]-3, METHYL-3, PROPANEDIOL-1-3

$C_{20}H_{24}NO_4$ MW = 339.398 [Formula 51]

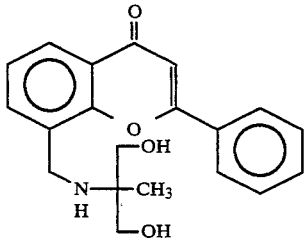

PF$_G$=150°-152° C.; IR $V_{c=o}$ (pyrone)=1630 cm$^{-1}$; V OH=3380 cm$^{-1}$; NMR (DMSO)δ in ppm in relation to TMS; 3H at 1 (s), 4H at 3.2 (d), 2H at 4 (s), 2H at 4.5 (t, exchangeable), 1H at 7 (s), 8H at 7.2 to 8.2 (m).

| | Elemental analysis | | | |
|---|---|---|---|---|
| | C% | H% | N% | O% |
| calculated: | 70.78 | 6.24 | 4.13 | 18.25 |
| found: | 70.51 | 6.42 | 4.37 | |

CHLOROHYDRATE OF (AMINOMETHYL)-8-PHENYL-2-4H-[1] BENZOPYRANONE-4

$C_{16}H_{14}ClNO_4$ MW = 287.19 [Formula 52]

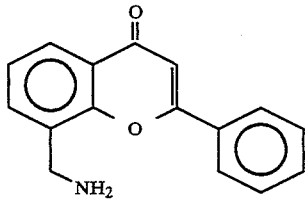

PF$_G$=275°-279° C.; IR V $NH_3$+=3100 to 2600 cm$^{-1}$; Vc-(pyrone)=1620 cm$^{-1}$; NMR (DMSO)δ in ppm in relation to TMS; 2H at 4.4(s), 1H at 7.1(s), 8H at 7.3 to 8.4 (m), 3H at 8.8 (exchangeable).

| | Elemental analysis | | | | |
|---|---|---|---|---|---|
| | C% | H% | Cl% | N% | O% |
| calculated: | 64.76 | 5.1 | 11.95 | 4.72 | 13.48 |
| found: | 65.05 | 4.73 | 12.08 | 4.46 | |

PHENYL-2-(TRIMETHOXY-3,4,5-PHENYLAMINOMETHYL)-8-4H-[1] BENZOPYRANONE-4

$C_{24}H_{23}NO_5$ MW = 417.47 [Formula 53]

-continued

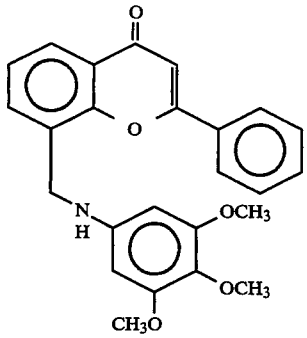

$PF_G$=219°-2221° C.; IR V NH=3350 $cm^{-1}$, $V_{c=o}$ (pyrone)=1620 $cm^{-1}$; NMR ($CF_3COOD$)δ in ppm in relation to TMS; 6H at 3.15 (s), 3H at 3.35 (s), 2H at 4.93 (s), 1H at 6.1 (s), 11H at 7 to 8.3 (m).

| | Elemental analysis | | | |
|---|---|---|---|---|
| | C % | H % | N % | O % |
| calculated | 74.93 | 5.55 | 3.35 | 19.16 |
| found | 71.65 | 5.58 | 3.35 | |

Example 5

(ACETYLOXY-1-ETHYL)-8-PHENYL-2-4H-[1] BENZOPYRANONE-4

$C_{19}H_{16}O_4$ MW = 308.32 [Formula 54]

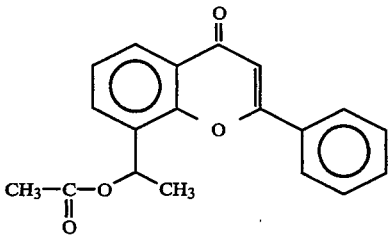

61.2 g (0.186 mole ) of (bromo-1-ethyl)-8-phenyl-2-4H-[1] benzopyranone-4 and 20.1 g (0.204 mole) of potassium acetate in 290 ml of DMF are mixed and heated, with stirring to 45° C. Heating is topped and the reaction mixture is returned to room temperature for 3 hours, with stirring. After one night at rest, the mixture is poured into ice water. Teh precipitate formed is filtered and recrystallized in alcohol. Weight obtained: 51 g (yield: 88.9%);

$PF_G$=137° C.; IR $V_{c=o}$ (ester)=1740 $cm^{-1}$, $V_{c=o}$ (pyrone)=1640 $cm^{-1}$; NMR ($DCDCl_3$)δ ppm in relation to TMS; 3H at 1.7 (d), 3H at 2.1 (s), 1H at 6.6 (g), 1H at 6.8, 8H at 7.2 to 8.4 (m).

Example 6

(HYDROXY-1-ETHYL)-8-PHENYL-2-4H-[1] BENZOPYRANONE-4

$C_{17}H_{14}O_3$ MW = 266.3 [Formula 55]

-continued

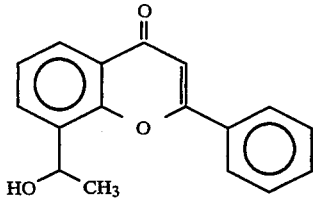

194.3 g (0.63 mole) of (acetyloxy-1-ethyl)-8-phenyl-2-4H-[1] benzopyranone-4 68.8 g (0.818 mole) of sodium bocarbonate are mixed in 239 ml of ethanol and 1628 ml of water. The mixture is kept under reflux for 5 hours. the mixture is heat-filtered, the filtrate is evaporated in a vacuum the residue to taken up in water and recrystallized in toluene. Weight obtained: 152.9 g (yield: 91%);

$PF_G$=154°-157° C.; IR V OH=3350 $cm^{-1}$, $V_{c=o}$ (pyrone)=1620 $cm^{-1}$; NMR ($CDCl_3$)δ in ppm in relation to TMS; 3H at 1.62 (d), 1H at 2.8 (exchangeable), 1H at 5.2 (q), 1H at 6.8 (s), 8H at 7.2 to 8.2 (m).

| | Elemental analysis | | |
|---|---|---|---|
| | C % | H % | O % |
| calculated | 76.67 | 5.30 | 18.03 |
| found | 76.50 | 5.19 | |

Example 7

ACETYL-8-PHENYL-2-4H-1 BENZOPYRANONE-4

$C_{17}H_{12}O_3$ MW = 264.28 [Formula 56]

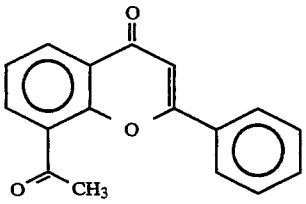

59.5 g (0.223 mole) of (hydroxy-1-ethyl)-8-phenyl-2-4H-[1] benzopyranone-4 are placed in 670 ml of dioxane. The medium is heated until a solution is obtained. This is then cooled to 20° C., and a reagent solution, prepared using 19.7 g (0.19 mole) of $CrO_3$, 50 ml of water, 13.6 ml of concentrated $H_2SO_4$ is addedin a dropwise manner. This mixture is kept for three hours at room temperature while being stirred, the insoluble is filtered, the filtrate is evaporated in a vacuum and the residue obtained is recrystallized in methyl isobutylcetone. Weight obtained: 43.3 g (yield: 73.4%);

$PF_G$=125°-126° C.; IR $V_{c=o}$ (cetone)=1675 $cm^{-1}$, $V_{c=o}$ (pyrone)=1690 $cm^{-1}$; NMR ($CDCl_3$)δ in ppm in relation to TMS; 3H at 2.8 (s), 1H at 6.8 (s), 8H at 7.3 to 8.6 (m).

| | Elemental analysis | | |
|---|---|---|---|
| | C % | H % | O % |
| calculated | 77.26 | 4.58 | 18.16 |
| found | 77.23 | 4.53 | |

Example 8

(BROMOACETYL)-8-PHENYL-2-4H-[1] BENZOPYRANONE-4

$C_{17}H_{11}BrO_3$ MW = 343.18 [Formula 57]

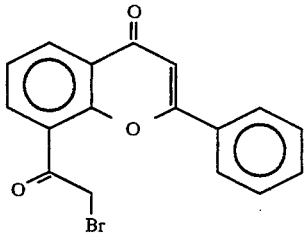

To a solution of 40 g (0.19 mole) of acetyl-8-phenyl-2-4H-[1] benzopyranone-4 in 750 ml of dioxane, 56.9 g (0.151 mole) of phenyltriethylammoniumtribromide are added. The mixture is stirred for 48 hours at room temperature, filtered, and the precipitate obtained is washed in water and recrystallized in acetone. Weight obtained: 42.9 g (yield: 82%);

$PF_G$=142° C.; IR $V_{c=o}$=1630 $cm^{-1}$, NMR ($CDCl_3$)δ in ppm in relation to TMS; 2H at 4.64 (s), 1H at 6.8 (s), 8H at 7.2 to 8.6 (m).

Example 9

(AMINO-2-THIAZOL-4-YL)-8-PHENYL-2-4H-[1] BENZOPYRANONE-4

$C_{18}H_{12}N_2O_2S$ MW = 320.37 [Formula 58]

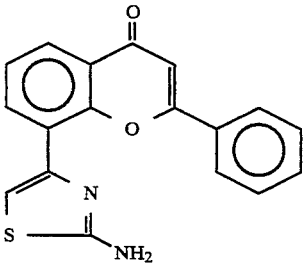

A mixture of 5 g (0.0146 mole) of (bromoacetyl)-8-phenyl-2-4H-[1] benzopyranone-4 and 2.22 g g (0.029 mole) thiourea in 100 ml of ethanol is heated for three hours under reflux, then poured into 200 ml of ice water. The precipitate formed is filtered, washed in water and rerystallized in a mixture of water and DMF. Weight obtained: 2.8 g (yield: 59%); IR V $NH_2$=3300 to 3500 $cm^{-1}$ $V_{c=o}$=1630 $cm^{-1}$; NMR ($CDCl_3$)δ in ppm in relation to TMS; 2H at 3.34 (exchangeable).

| | Elemental analysis | | | | |
|---|---|---|---|---|---|
| | C % | H % | N % | O % | S % |
| calculated | 67.48 | 3.78 | 8.74 | 9.99 | 10.01 |
| found | 67.57 | 3.65 | 8.84 | | 10.06 |

Using this same technique, the following compounds were prepared:

[METHYL-2-THIAZOL-4YL)-8-PHENYL-2-4H-[1] BENZOPYRANONE-4

$C_{19}H_{13}NO_2S$ MW = 319.37 [Formula 59]

-continued

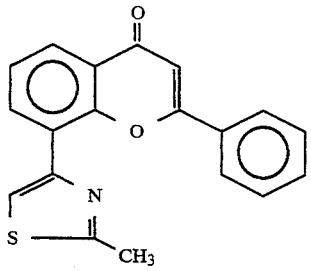

$PF_G$32 148°-153° C.; IR $V_{c=o}$ (acid)=1639 $cm^{-1}$, NMR ($CDCl_3$)δ in ppm in relation to TMS; 3H at 2.8 (s), 1H at 6.8 (s), 9H at 7.2 to 8.5 (m).

| | Elemental analysis | | | | |
|---|---|---|---|---|---|
| | C % | H % | N % | O % | S % |
| calculated | 71.45 | 4.10 | 4.39 | 10.02 | 10.04 |
| found | 71.39 | 4.03 | 4.36 | | 10.30 |

(IMIDAZO [2,1-B] THIAZOL-6-YL)-8-PHENYL-2-4H-[1] BENZOPYRANONE-4

$C_{20}H_{12}N_2O_2$ S MW = 344.39 [Formula 60]

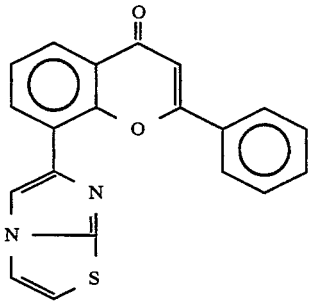

$PF_G$=229°-233° C.; IR $V_{c=o}$=1630 $cm^{-1}$, NMR (DMSO+$CF_3COOD$)δ in ppm in realtion to TMS; 1H at 7 (s), 11H at 7.4 to 8.8 (m).

| | Elemental analysis | | | | |
|---|---|---|---|---|---|
| | C % | H % | N % | O % | S % |
| calculated | 69.75 | 3.51 | 8.14 | 9.28 | 9.31 |
| found | 69.50 | 3.59 | 8.01 | | 9.37 |

[IMIDAZO [1,2-A] PYRIDIN-2-YL]-8-PHENYL-2-4H-[1] BENZOPYRANONE-4

$C_{22}H_{14}N_2O_2$ MW = 338.35 [Formula 61]

-continued

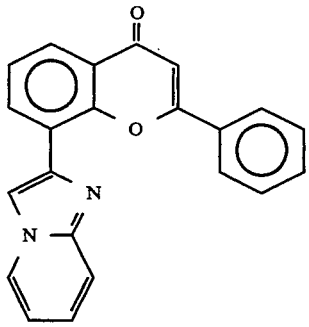

$PF_G$=203°-205° C.; IR $V_{c=o}$=1635 $cm^{-1}$, NMR ($CDCl_3$)δ in ppm in relation to TMS; 1H at 6.8 (s), 13H at 7 to 8.7 (m).

| | Elemental analysis | | | |
|---|---|---|---|---|
| | C % | H % | N % | O % |
| calculated | 78.09 | 4.17 | 8.28 | 9.46 |
| found | 78.16 | 4.12 | 8.26 | |

(INDOLIZIN-2-YL)-8-PHENYL-2-4H-[1] BENZOPYRANONE-4

$C_{23}H_{15}NO_2$ MW = 337.36 [Formula 62]

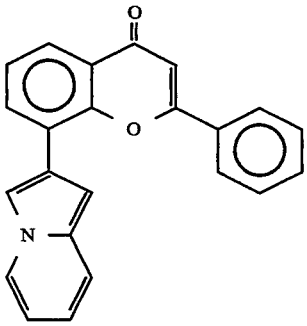

$PF_G$=204°-207° C.; IR $V_{c=o}$1639 $cm^{-1}$, NMR ($CDCl_3$)δ in ppm in relation to TMS; 1H at 6.8 (s), 1H at 7.3 to 8.3 (m).

| | Elemental analysis | | | |
|---|---|---|---|---|
| | C % | H % | N % | O % |
| calculated | 81.88 | 4.48 | 4.15 | 9.49 |
| found | 82.03 | 4.60 | 4.16 | |

PHENYL-2-(PHENYL-2-THIAZOL-4-YL)-8-4H-[1] BENZOPYRANONE-4

$C_{24}H_{15}O_2S$ MW = 381.46 [Formula 63]

-continued

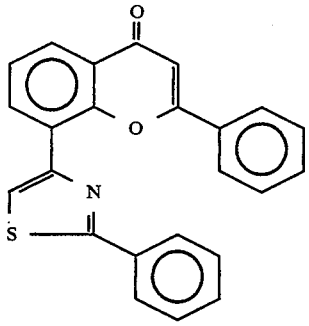

$PF_G$=199°-202° C.; IR $V_{c=o}$=1650 $cm^{-1}$, NMR ($CF_3COOD$)δ in ppm in relation to TMS; 15H at 7.4 to 8.8.

| | Elemental analysis | | | | |
|---|---|---|---|---|---|
| | C % | H % | N % | O % | S % |
| calculated | 75.57 | 3.96 | 3.67 | 8.39 | 8.41 |
| found | 75.42 | 4.03 | 3.64 | | 8.15 |

(DIHYDRO-2-3-IMIDAZO [2,1-B] THIAZOL-6-YL)-8-PHENYL-2-4H-[1] BENZOPYRANONE-4

$C_{20}H_{14}N_2O_2S$ MW = 346.40 [Formula 64]

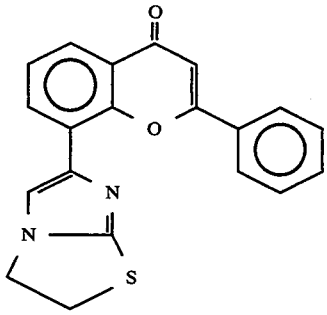

$PF_G$=226°-230° C.; IR $V_{c=o}$=1635 $cm^{-1}$, NMR (DMSO)δ in ppm in relation to TMS; 4H at 4 to 5 (m), 1H at 7 (s), 9H at 7.4 to 8.3 (m).

| | Elemental analysis | | | | |
|---|---|---|---|---|---|
| | C % | H % | N % | O % | S % |
| calculated | 69.34 | 4.07 | 8.09 | 9.24 | 9.26 |
| found | 69.21 | 4.19 | 8.32 | | 9.02 |

Example 10

ACETOXYMETHYL-10-PHENYL-2-4H-NAPHTO [1,2-b] PYRANONE-4

$C_{22}H_{16}O_4$ MW = 334.37 [FORMULA 65]

-continued

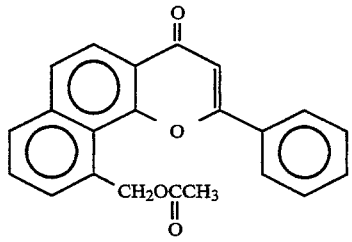

A mixture of 19.8 g (0.054 mole) of bromomethyl-10-phenyl-2-4H-naphto[1,2-b]pyranone-4, 5.3 g (0.054 mole) of potassijm acetate, and 110 ml of DMF is heated to 45° with stirring. This mixture is allowed to return to room temperature while still being stirred for one hour. It is poured into a mixture of water and ice, and the solid obtained is then filtred and used in the following step, without further purification. Weight obtained: 18.5 g (quantitative yield); $PF_G$=170° C.; IR $V_{c=o}$ (ester)=1740 $cm^{-1}$, $V_{c=o}$ (pyrone)=1635 $cm^{-1}$; NMR ($CDCl_3$)δ in ppm in relation to TMS; 3H at 2.1 (s), 2H at 5.9 (s), 1H at 6.9 (s), 10H at 7.2 to 8.6 (m).

HYDROXYMETHYL-10-PHENYL-2-4H-NAPHTO[1,2-b]PYRANONE-4

$C_{20}H_{14}O_3$ MW = 302.33 [FORMULA 66]

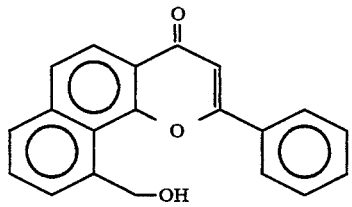

A mixture of 18.9 G (0.054 mole) of acetoxymethyl-10-phenyl-2-4H-naphto [1,2-b pyranone-4, 100 ml of ethanol and 39 g (0.07 mole) of potassium in table form is heated in a reflux for two hours. It is then poured into a water-ice mixture and acidified using 6N HCl. The precipitate obtained is filtered, dried, and used in the following step without further purification. Weight obtained: 16.2 g (yield=99%): $I_R$ V OH=3400 $cm^{-1}$; $V_{c=o}$=1630 $cm^{-1}$; NMR (DMSO) δ in ppm in relation to TMS: 1H at 3.5 (s, large), 2H at 5.4 (s), 1H at 7 (s), 10H at 7.2 to 8.4.

CARBOXY-10-PHENYL-2-4H-NAPHTO[1,2-b]PYRANONE-4

$C_{20}H_{12}O_4$ MW = 316.31 [FORMULA 67]

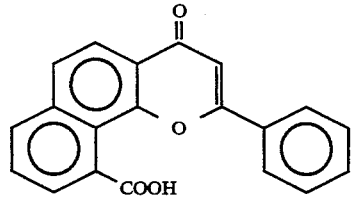

A mixture of 16.2 g (0.0536 mole) of hydroxymethyl-10-phenyl-2-4H-naphto [1,2-b]pyranone 4, 430 ml of pyridine, and 100 ml of water is heated to 60° C. 31.7 g (0.2 mole) of potassium permanganate is added over two hours in portions, then the mixture is heated for 4 hours in a reflux. It is then cooled, and treated with a watery solution of sodium metasulfite, until discoloration is obtained. It is poured into 1 liter of water, the insoluble is filtered, and the organic phase is poured off. After evaporation in a vacuum, the residue is taken up again by the water, acidified using 6N HCl. The precipitate obtained is filtered and recrystallized in acetic acid. Weight obtained: 1.1 g (yield 6.5%); mp=278°-280° C.; IR $V_{c=o}$ (acid)=1700 $cm^{-1}$, $V_{c=o}$ (pyrone)=1620 $cm^{-1}$; NMR (DMSO) δ in ppm in relation to TMS: 1H at 7.15 (s), 10H at 7.4 to 8.4 (m). 1H at 13.5 (exchangeable).

| | Elemental Analysis | | |
|---|---|---|---|
| | C % | H % | O % |
| calculated | 75.96 | 3.82 | 20.24 |
| found | 75.58 | 3.77 | |

Example 11

OXO-4-PHENYL-1-4H-[1]-BENZOPYRAN-8-ACETATE OF (ETHOXYCARBONYL)-1-ETHYL $C_{20}H_{20}O_6$ MW = 380.38 [FORMULA 68]

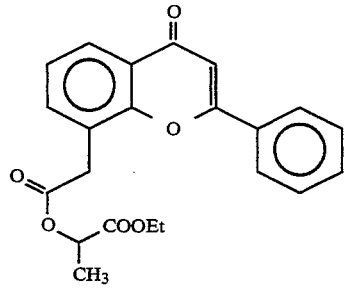

To a suspension of 30.6 g (0.109 mole) of oxo-4-phenyl-2-4H-l-benzopyran-8-acetic acid in 1.9 1 of boiling ethanol is added dropwise a solution of 7.2 g (0.109 mole) of potassium in 100 ml of ethanol. The solution obtained is stirred for 30 minutes, allowed to return to room temperature, and evaporated in a vacuum. The residum is taken up using 300 ml of ethanol and evaporated in a vacuum, then taken up agin using 30 ml of benzene and evaporated in a vacuum. 546 ml of methyl isobutylketone (MIBK) is added to the residuum, followed by a solution of 21.7 g (0.12 mole) of ethyl α-bromopropionate in 55 ml of MIBK. This mixture is heated in a reflux for 3 hours; next, 12 g (0.066 mole) of ethyl α-bromopropionate is added before continuing heating for 5 hours in a reflux. Heat-filtratioin is carried out, and the filtrate is evaporated in a vacuum. The residuum is triturated in hexane in order to obtain a precipitate which is filtered, washed with hexane and recrystallized in isopropanol. Weight obtained: 36.2 g (yield: 87%); mp =104°-106° C.; IR $V_{c=o}$ (pyrone) =1730 $cm^{-1}$, $V_{c=o}$ (pyrone)=1640 $cm^{-1}$; NMR ($CDCl_3$) δ in ppm in relation to TMS: 3H at 1.2 (t), 3H at 1.46 (d), 2H at 4.1 (s), 2H at 4.18 (q), 1H at 5.18 (q), 1H at 6.8 (s), 8H at 7.2 to 8.4 (m). (exchangeable).

HYDROXY-4-METHYL-5-(OXO-4-PHENYL-2-4H-[1]-BENZOPYRAN-8-YL)-3-5H-FURANONE-2

$C_{20}H_{14}O_5$ MW = 334.31 [FORMULA 69]

-continued

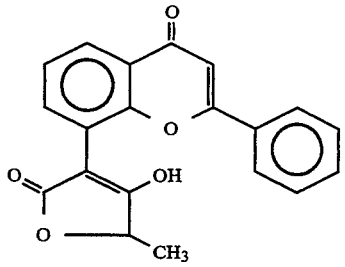

To a suspension of 2.62 g (0.109 mole) of sodium hydride in 226 ml of HMPT, is added dropwise to a solution of 41.7 g (0.109 mole) of oxo-4-phenyl-2-4H-[1]-benzopyran-8-acetate of (ethylcarbonyl)-1-ethyl in 260 ml of HMPT. This mixture is stirred overnight in an atmosphere of argon at room temperature, and is then carefully hydroiized using 2 l of 6N HCl. The precipitate obtained is filtered and recrystallized. Weight obtained: 28.3 g (yield 77%); mp =265°-268° C.; IR V OH=3400 to 2200 $cm^{-1}$ Vc=o (lactone) =1740 $cm^{-1}$; $V_{c=o}$(pyrone)=1600 $cm^{-1}$; NMR (DMSO) δ in ppm in relation to TMS: 3H at 1.6 (d), 1H at 5.2 (q), 1H at 7.1 (s), 9H at 7.2 to 8.6.

| | Elemental Analysis | | |
|---|---|---|---|
| | C % | H % | O % |
| calculated | 71.85 | 4.22 | 23.93 |
| found | 71.55 | 4.11 | |

Using the same technique, the following compounds were obtained:

(CHLORO-4-PHENYL)-5-HYDROXY-4-(OXO-4-PHENYL-2-4H-[1]-BENZOPYRAN-8-YL)-3-5H-FURANONE-2

$C_{25}H_{15}ClO_5$ MW = 430.83 [FORMULA 70]

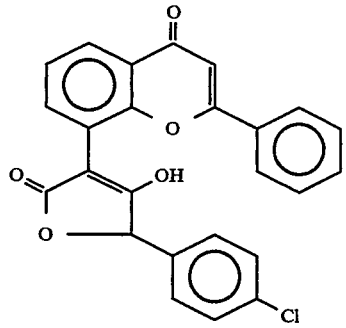

mp=266°-273° C.; IR $V_{c=o}$ (lactone)=1750 $cm^{-1}$, $V_{c=o}$ (pyrone)=1660 $cm^{-1}$, NMR (DMSO) δ in ppm in relation to TMS: 1H at 6.16 (s), 1H, at 7(s), 13H at 7.1 to 8.4.

| | Elemental Analysis | | | |
|---|---|---|---|---|
| | C % | H % | Cl % | O % |
| calculated | 69.69 | 3.51 | 8.23 | 18.57 |
| found | 69.41 | 3.52 | 8.27 | |

METHYL-3-HYDROXY-4-(OXO-4-PHENYL-2-4H-[1]-BENZOPYRAN-8-YL)-5-5H-FURANONE-2

-continued $C_{20}H_{14}O_5$ MW = 334.31 [FORMULA 71]

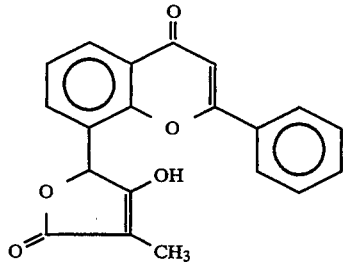

mp=160° C.; $I_R$ $V_{c=o}$ (lactone)=1760 $cm^{-1}$, $V_{c=o}$ (pyrone)=1640 $cm^{-1}$; NMR (DMSO) δ in ppm in relation to TMS: 3H at 1.8 (s), 1H at 6.55 (s), 1H at 7.75 (s), 9H at 7.5 to 8.3 (m).

| | Elemental Analysis | | |
|---|---|---|---|
| | C % | H % | O % |
| calculated | 71.85 | 4.22 | 23.93 |
| found | 71.80 | 4.22 | |

Example 12

CHLORHYDRATE OF [(N,N-DIETHYLAMINO)-2-ETHOXY]-4-METHYL-5-[OXO-4-PHENYL-2-4H-[1]-BENZOPYRAN-8-YL]-3-5H-FURANONE-2

$C_{26}H_{28}ClNO_5$ MW = 469.95 [FORMULA 72]

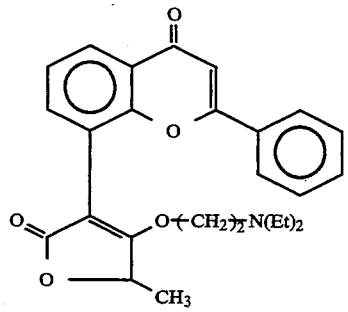

A mixture of 20 g (0.06 mole) of hydroxy-4-methyl-5-(oxo-4-phenyl-2-4H-[1]-benzopyran-9.93 g (0.72 mole) of potassium carbonate, and 0.36 g (0.002 mole) of potassium iodide in 490 ml of MIBK is heated for 1 hour at reflux. Next, a solution of 10.6 g (0.078 mole) of 2-(diethylamino)ethyl chloride in 90 ml of MIBK is added, and heating is continued for 7 hours. The minerals are heat filtered and the liltrate is evaporated in a vacuum. The residum is washed twice in hexane then solubilized in the minimum amount of acetone and diluted using hexane. A light insoluble is filtered, the filtrate is evaporated in a vacuum and the residuum is dissolved in 200 ml of ethanol. This product is cooled in an ice bath and HC1 is bubbled through until a pH of 2 is achieved. By adding ether, a precipitate is obtained, which is filtered and recrystallized in an ethanol-ether mixture. Weight obtained: 16.9 g (yield 60%); mp=168°-169° C.; IR $V_{c=o}$ (lactone)=1740 $cm^{-1}$, $V_{c=o}$ (pyrone)=1640 $cm^{-1}$; NMR (DMSO-$CDCl_3$) δ in ppm in relation to TMS: 6H at 0.9 (t), 3H at 1.5 (d), 6H at 2.6 to 3.3 (m), 2H at 4.2 (t), 1H at 5.2 (q), 1H at 6.75 (s), 8H at 7.3 to 8.2.

| | Elemental Analysis | | | | |
|---|---|---|---|---|---|
| | C % | H % | Cl % | N % | O % |
| calculated | 66.45 | 6.00 | 7.55 | 2.98 | 17.02 |
| found | 66.30 | 6.20 | 7.55 | 2.83 | |

Using the same technique, the following compounds were obtained:

[DIHYDRO-2-5-METHY-5-OXO-2-(OXO-4-PHENYL-2-4H-[1]-BENZOPYRAN-8-YL)-3-FURAN-4-YL] ETHYL OXYACETATE $C_{24}H_{20}O_7$ MW = 420.4 [FORMULA 73]

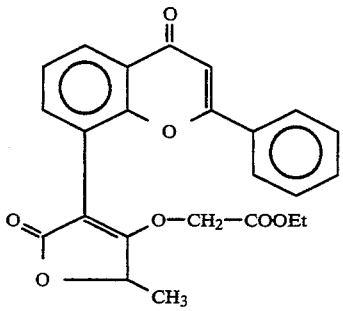

mp=153° C.; IR Vc=o NMR (ester and lactone)=1755 $cm^{-1}$, $V_{c=o}$ (pyrone)=1640 $cm^{-1}$ NMR ($CDCl_3$) δ in ppm in relation to TMS: 3H at 1 (t), 3H at 1.7 (d), 2H at 3 9 (q), 2H at 4.5 (s), 1 H at 5.18 (q), 1H at 6 9 . (s), 8H at 7.2 to 8.5.

[DIHYDRO-2-5-METHYL-5-OXO-2-(OXO-4-PHENYL-2-4H-[1]-BENZOPYRAN-8-YL)-3-FURAN-4-YL] OXYACETIC ACID $C_{22}H_{16}O_7$ MW = 392.39 [FORMULA 74]

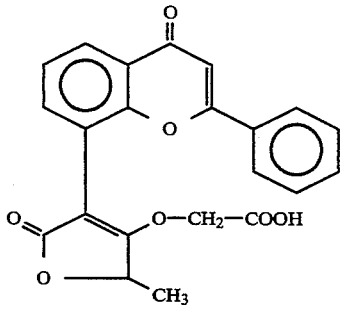

mp=257°-259° C.; IR V OH=2400 $cm^{-1}$ Vc=o (lactone)=1740 $cm^{-1}$, $V_{c=o}$ (acid)=1710 $cm^{-1}$, $V_{c=o}$ (pyrone)=1620 $cm^{-1}$; NMR (DMSO) δ in ppm in relation to TMS: 3H at 1.6 (d), 1H at 4 (exchangeable), 2H at 4.66 (s), 1H at 5.4 (q), 1H at 7.08 (s), 8H at 7.2 to 8.4 (m).

| | Elemental Analysis | | |
|---|---|---|---|
| | C % | H % | O % |
| calculated | 67.34 | 4.11 | 28.55 |
| found | 67.20 | 4.00 | |

DIMETHYL CARBAMOTHIOATE OF O-[DIHYDRO-2,5-METHYL-5-OXO-2-(OXO-4-PHENYL-2-4H-[1]-BENZOPYRAN-8-YL)-3-FURN-4-YL]

$C_{23}H_{19}NO_5S$ MW = 421.46 [FORMULA 75]

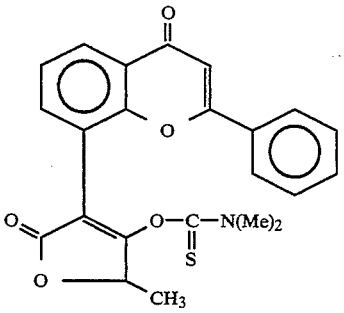

mp=173°-175° C.; IR $V_{c=o}$ (lactone)=1740 $cm^{-1}$, $V_{c=o}$ (pyrone)=1630 $cm^{-1}$; NMR ($CDCl_3$) δ in ppm in relation to TMS: 3H at 1.66 (d), 6H at 2.8 (s), 1H at 6.16 (q), 1H at 6.8 (s), 8H at 7.2 to 8.4 (m).

| | Elemental Analysis | | | | |
|---|---|---|---|---|---|
| | C % | H % | N % | O % | S % |
| calculated | 65.54 | 4.70 | 3.32 | 18.98 | 7.61 |
| found | 65.42 | 4.52 | 3.32 | | 7.64 |

Example 13

ACETYLTHIOMETHYL-8-OXO-4-PHENYL-2-4H-[1]-BENZOPYRANE $C_{18}H_{14}O_3S$ MW = 310.38 [FORMULA 76]

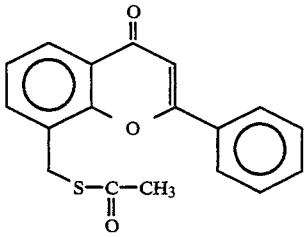

To a mixture of 17.4 g (0.152 mole) of potassium thioacetate in 120 ml of DMF is added 48 g (0.152 mole) of bromomethyl-8-phenyl-2-4H-[1]-benzopyranone-4, by portions while being stirred. This is stirred for 1 hour at room temperature and then poured into a water-ice mixture. The precipitate obtained is filtered and recrystallized in ethyl acetate. Weight obtained: 38 g (yield: 80%); mp=160° C.; IR $V_{c=o}$(ester)=1690 $cm^{-1}$, $V_{c=o}$ (pyrone)=1655 $cm^{-1}$; NMR ($CDCl_3$) δ in ppm in relation to TMS: 3H at 2.4 (s), 2H at 4.5 (s), 1H at 6.9 (s), 8H at 7.2 to 8.4 (m).

Example 14

MERCAPTOMETHYL-8-PHENYL-2-4H-[1]-BENZO-PYRANONE-4

$C_{16}H_{12}O_2S$ MW = 268.34 [FORMULA 77]

-continued

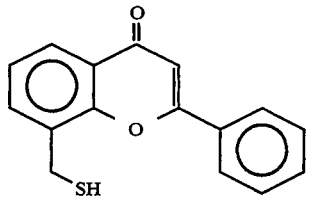

To a mixture of 38 g (0.122 mole) of thioacetylmethyl-8-phenyl-2-4H-[1]-benzopyranone-4 and 230 ml of ethanol are added at one time 150 ml of saturated ethanol in anhydrous HCl. This is heated for 18 hours in a reflux. This mixture is cooled and the precipitate obtained is heated and recrystallized in ethanol. Weight obtained: 39.7 g (yield: 97%); mp=162° C.; IR $V_{c=o}$=1640 $cm^{-1}$; NMR ($CDCl_3$) δ in ppm in relation to TMS: 1H at 2 (t), 2H at 4.1 (d), 1H at 6.8 (s), 8H at 7.2 to 8.4 (m) (exchangeable).

| Elemental Analysis | C % | H % | O % | S % |
|---|---|---|---|---|
| calculated | 71.62 | 4.51 | 11.92 | 11.95 |
| found | 71.45 | 4.48 | | 11.84 |

Using the same technique, the following compounds were prepared:

(OXO-4-PHENYL-2-4H-[1]-BENZOPYRAN-8-YL)-METHYL] METHYL THIOACETATE $C_{19}H_{16}O_4S$ MW = 340.4 [FORMULA 78]

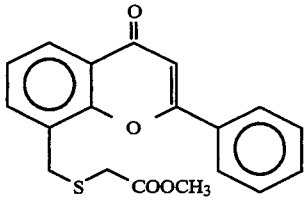

mp=110° C.; IR $V_{c=o}$ (ester)=1720 $cm^{-1}$; $V_{c=o}$ (pyrone)=1650 $cm^{-1}$ NMR ($CDCl_3$) δ in ppm in relation to TMS: 2H at 3.2 (s), 3H at 3.7 (s), 2H at 4.2 (s), 1H at 6.8 (s), 8 H at 7.2 to 8.4 (m).

(OXO-4-PHENYL-2-4H-[1]-BENZOPYRAN-8-YL) METHLTHIOACETIC ACID $C_{18}H_{14}O_4S$ MW = 326.37 [FORMULA 79]

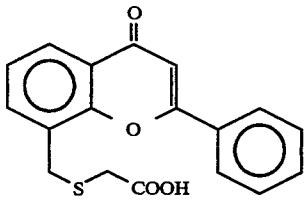

mp=200°-204° C.; IR V OH=3100-2400 $cm^{-1}$, IR $V_{c=o}$ (acid)=1720 $cm^{-1}$, $V_{c=o}$ (pyrone)=1640 $cm^{-1}$, NMR (DMSO) δ in ppm relation to TMS: 2H at 3.2 (s), 2H at 4.25 (s), 1H at 6.8 (s), 9H at 7.2 to 8.4 (m).

| Elemental Analysis | C % | H % | O % | S % |
|---|---|---|---|---|
| calculated | 66.24 | 4.32 | 19.61 | 9.81 |
| found | 66.51 | 4.34 | | 10.11 |

OXALATE OF DIETHYLAMINO-2-ETHOXYMETHYL)-8-PHENYL-2-4H-[1]-BENZOPYRANONE-4

$C_{24}H_{27}NO_7$ MW = 441.48 [FORMULA 80]

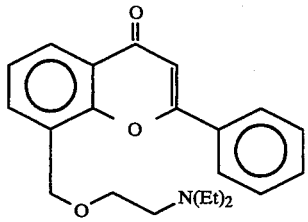

mp=162°-164° C.; IR $V_{c=o}$=1660 $cm^{-1}$; NMR (DMSO) δ in ppm in relation to TMS: 3H at 1.2 (t), 6H at 2.95 to 3.5 (m), 1H at 3.8 to 4.2 (m), 2H at 5.05 (s), 2H at 5.4 (exchangeable), 1H at 7.1 (s), 8H at 7.5 to 8.5 (m).

| Elemental Analysis | C % | H % | N % | O % |
|---|---|---|---|---|
| calculated | 65.29 | 6.16 | 3.17 | 25.37 |
| found | 65.18 | 6.10 | 3.07 | |

[[HYDROXY-2-(HYDROXYMETHYL)-1-ETHOXY] METHYL]-8-PHENYL-2-4H-[1]-BENZOPYRANONE-4

$C_{19}H_{18}O_5$ MW = 326.33 [FORMULA 81]

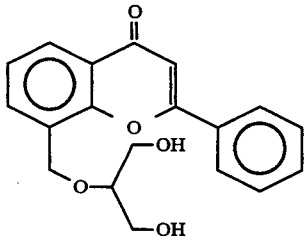

mp=162° C.; IR V OH=3300 $cm^{-1}$; IR $V_{c=o}$ 1620 $cm^{-1}$, NMR (DMSO) δ in ppm in relation to TMS: 5H at 3.3 to 3.7 (m), 2H at 4.5 (exchangeable), 2H at 5 (s), 1H at 6.93 (s), 8H at 7.2 to 8.2 (m).

| Elemental Analysis | C % | H % | O % |
|---|---|---|---|
| calculated: | 69.93 | 5.56 | 24.51 |
| found: | 70.00 | 5.57 | |

Example 15

OXO-4-PHENYL-2-4H-[1]-BENZOPYRAN-8-ACETAMIDE $C_{17}H_{13}NO_3$ MW = 279.28 [Formula 82]

-continued

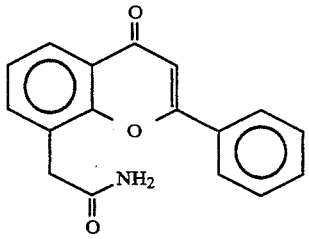

A suspension of 5 G (0.0178 mole) of oxo-4-phenyl-2-4H-[1]-benzopyran-8-acetic acid in 180 ml of dioxane is heated until it dissolves. A solution of 3.5 g (0.0124 mole) of N,N'-carboxyldiamidazole in 30 ml of dioxane is added and the mixture is heated for 1 hour to 80° C. It is then cooled to 20° C. and approximately 10 ml (0.4 mole) liquified anhydrous ammonia at −33° C. is slowly added. The mixture is stirred for 10 minutes at 20° C., then for 3 hours at 80° C. This is left overnight, filtered, washed with hexane, then with hot 5% sodium bicarbonate solution, then with water; it is next recrystallized in ethanol. Weight obtained: 3.3 g (yield 66%); mp=232°–258° C.; IR V NH=3370 to 3200 $cm^{-1}$; IR $V_{c=o}$ (acid)=1660 $cm^{-1}$, $V_{c=o}$ (pyrone)=1630 $cm^{-1}$; NMR ($CDCl_3+CF_3COOD$) δ in ppm in relation to TMS: 2H at 4.33 (s), 9H at 7.5 to 8.7 (m), 2H at 11.5.

| Elemental Analysis | C % | H % | N % | O % |
|---|---|---|---|---|
| calculated: | 73.13 | 4.69 | 5.01 | 17.19 |
| found: | 73.13 | 4.69 | 5.00 | |

Example 16

OXO-4-PHENYL-2-4H-[1]-BENZOPYRAN-8-THIOACETAMIDE $C_{17}H_{13}NO_2S$ MW = 295.35 [FORMULA 83]

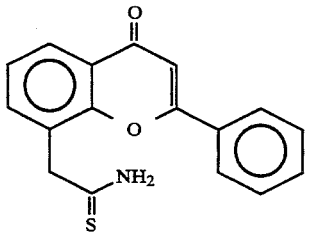

In a mixture of 60 g (0.229 mole) of oxo-4-phenyl-2-4H-[1]-benzopyran-8-acetonitrile, 16.2 ml (0.116 mole) of triethylamine and 900 ml of pyridine, a stream of $H_2S$ is bubbled through for 3 hours. A nitrogen stream is then passed through this mixture and it si poured into 5 l of ice water, acidified to a pH 5–6 with HCl, filtered, washed in ether, dried, and crystallized in DMF. Weight obtained: 24.7 g (yield: 36%); mp=223°–224° C.; IR V NH=3250 and 3080 $cm^{-1}$; IR $V_{c=o}$=1620 $cm^{-1}$; NMR (DMSO) δ in ppm in relation to TMS: 2H at 4.15 (s), 1H at 6.9 (s), 8H at 7.2 to 8.4 (m), 2H at 9.4 (s).

| Elemental Analysis | C % | H % | N % | O % | S % |
|---|---|---|---|---|---|
| calculated: | 69.13 | 4.44 | 4.74 | 10.83 | 10.86 |
| found: | 69.22 | 4.38 | 4.80 | | 10.68 |

Example 17

PHENYL-2-[(PHENYL-4-THIAZOL-2-YL)METHYL]-8-4H-[1]-BENZOPYRANONE-4

$C_{25}H_{17}NO_2$ MW = 395.46 [Formula 84]

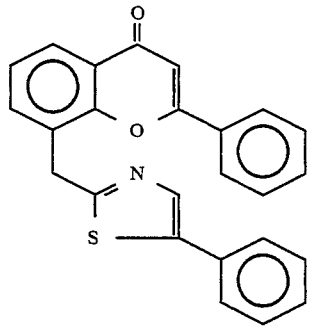

A mixture of 5 g (0.0169 mole) of oxo-4-phenyl-2-4H-[1]-benzopyran-8-thioacetamide, 4 g (0.0203 mole) of d-bromoacetophenone and 120 ml of methoxyethanol is heated for five hours of reflux, then cooled and left overnight at −20° C. The solid obtained is filtered and recrystallized in MIBK then in acetone. Weight obtained: 3.3 g (yield: 49%); IR $V_{c=o}$ 1620 $cm^{-1}$; NMR ($CDCl_3$) δ in ppm in relation to TMS: 2H at 4.7 (s), 1H at 6.75 (s), 14 H at 7.1 to 8.3 (m).

| Elemental Analysis | C % | H % | N % | O % | S % |
|---|---|---|---|---|---|
| calculated | 75.92 | 4.33 | 3.54 | 8.09 | 8.11 |
| found | 75.73 | 4.23 | 3.52 | | 8.31 |

Using this same technique, the following compounds were prepared:

[(OXO-4-PHENYL-2-4H-[1]-BENZOPYRAN-8-YL) METHYL]-2-THIAZOL-4-ETHYL CARBOXYLATE $C_{22}H_{17}NO_4S$ MW = 391.43 [FORMULA 85]

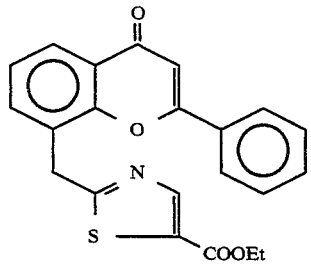

mp=152°–153° C.; IR $V_{c=o}$ (ester)=1710 $cm^{-1}$, $V_{c=o}$ (pyrone)=1640 $cm^{-1}$; NMR ($CDCl_3$) δ in ppm in relation to TMS: 3H at 1.3 (t) 2H at 4.4 (q), 2H at 4.73 (s), 1H at 6.7 (s), 9H at 7.1 to 8.3 (m).

[(OXO-4-PHENYL-2-4H-{12}-BENZOPYRAN-8-YL) METHYL-2-THIAZOL-4-CARBOXYLIC ACID $C_{20}H_{13}NO_4S$ MW = 362.38 [FORMULA 86]

-continued

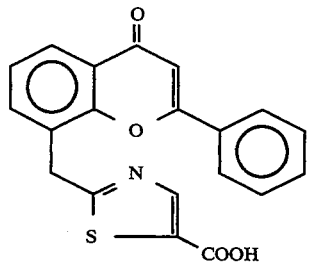

mp=237°-240° C.; IR V OH=3100 to 2400 $cm^{-1}$; IR $V_{c=o}$ (acid)=1720 $cm^{-1}$, $V_{c=o}$ (pyrone)=1620 $cm^{-1}$ NMR (DMSO) δ in ppm in relation to TMS: 1H at 3.4 (exchangeable), 2H at 4.7 (s), 1H at 6.9 (s), 8H at 7.2 to 8.15 (m), 1H at 8.2 (s).

| Elemental Analysis | C % | H % | N % | O % | S % |
|---|---|---|---|---|---|
| calculated: | 66.10 | 3.61 | 3.85 | 17.61 | 8.82 |
| found: | 69.83 | 3.60 | 3.87 | | 8.60 |

Example 18

[OXO-4-PHENYL-2-4H-[1]-BENZOPYRAN-8-YL) METHYLENE]-2-HYDRAZINE CARBOTHIOAMIDE $C_{17}H_{13}N_3O_2S$ MW = 323.36 [FORMULA 87]

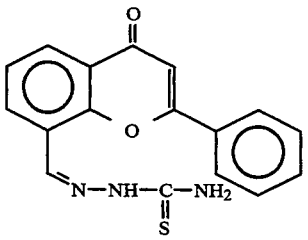

A suspension of 5 g (0.02 mole) of (oxo-4-phenyl-2-4H-[1]-benzopyran-8-yl ) carboxaldehyde in 120 ml of dioxane was heated until dissolution. This was cooled to 25° C., a solution of 2 g (0.022 mole) of thiosemicarbazide in 40 ml of dioxane was added and this was heated for 5 minutes at 90° C., then left to return to 25° C. while stirring. The precipitate was filtered and recrystallized in methoxyethanol. Weight obtained: 48 g (yield: 41%); mp=258°-262° C.; IR V NH=3400 to 3100 $cm^{-1}$, $V_{c=o}$: 7640 $cm^{-1}$.

| Elemental Analysis | C % | H % | N % | O % | S % |
|---|---|---|---|---|---|
| calculated: | 63.14 | 4.05 | 13.00 | 9.90 | 9.92 |
| found: | 63.12 | 4.04 | 13.00 | | 9.87 |

Using the same method, the following compound was prepared:

DIHYDRO-4,5-[1H]-IMIDAZOL-2-YL-HYDRAZONE BROMHYDRATE OF (OXO-4-PHENYL-2-4H-[1]-BENZOPYRAN-8-YL) CARBOXALDEHYDE $C_{19}H_{17}BrN_4O_4$ MW = 413.28 [FORMULA 88]

-continued

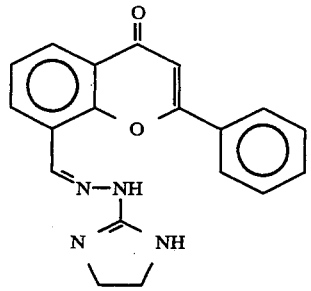

mp=301°-303° C.; IR: V NH=3300 $cm^{-1}$; V C=N−C=O=1660 and 1640 $cm^{-1}$; NMR (DMSO) δ in ppm in relation to TMS: 2H to 3.4 (s), 4H to 3.8 (s), 1H to 7.1 (s), 10H from 7.3 to 9 (m of which 1H is exchangeable).

| Elemental Analysis | C % | H % | Br % | N % | O % |
|---|---|---|---|---|---|
| calculated: | 55.21 | 4.15 | 19.34 | 13.56 | 7.74 |
| found: | 54.96 | 4.09 | | 13.62 | |

Example 19

(OXO-4-TETRAHYDRO-2,3,5,6-4H-PYRAN-2-YL)-8-PHENYL-2-4H-[1]-BENZOPYRANONE-4

$C_{20}H_{16}O_4$ MW = 320.33 [FORMULA 89]

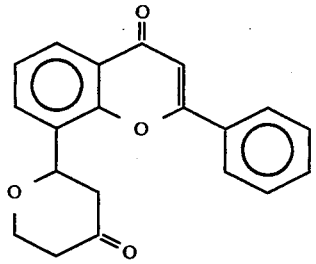

20 g (0.08 mole) of oxo-4-phenyl-2-4H-[1]-benzopyran-8-carboxaldehyde were added in parts to a mixture of 22.8 g (0.16 mole) of trimethylsilyloxy-2-butadiene-1-3 and 12 g (0.088 mole) of anhydrous $ZnCl_2$ in 500 ml of anhydrous dioxane. This was brought to reflux for 8 hours under nitrogen and then left under stirring for 48 hours at room temperature. A slight insoluble product was filtered and 1 liter of a solution of 5% $NaHCO_3$ was added to the liltrate. The insoluble product formed was filtered and the liltrate was extracted using ethyl acetate, then dried and evaporated under a vacuum. The residue was dissolved in 300 ml of methanol and brought to reflux for 3 hours. After having been cooled to 25° C., 3.6 ml of acetic acid were added and this was left under stirring for one night. This was evaporated under a vacuum and the residue was recrystallized in MIBK. Weight obtained: 9.2 g (yield: 30%); mp=220°-221° C.; IR $V_{c=o}$ (pyranone)=7695 $cm^{-1}$ V C=O (pyrone)=1640 $cm^{-1}$; NMR ($CDCl_3$) δ in ppm in relation to TMS: 4H from 2.3 to 3.2 (m), 2H from 3.7 to 4.7 (m), 1H to 5.3 (dd), 1H to 6.8 (s), 8H from 7.1 to 8.3 (m).

| Elemental Analysis | C % | H % | O % |
|---|---|---|---|
| calculated: | 74.98 | 5.03 | 19.98 |

-continued

| Elemental Analysis | C % | H % | O % |
|---|---|---|---|
| found: | 75.03 | 4.81 | |

Example 20

(HYDROXY-4-TETRAHYDRO-3,4,5,6-2H-PYRAN-2-YL)-8-PHENYL-2-4H-[1]-BENZOPYRANONE-4

$C_{20}H_{18}O_4$ MW = 322.34 [FORMULA 90]

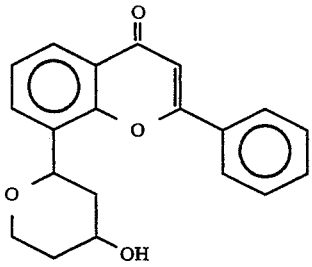

A mixture of 6.8 g (0.021 mole) of the compound of Example 18,116 ml of dioxane and 58 ml of methanol was heated until dissolution. It was cooled to 35° C. and 0.9 g (0.023 mole) of $NABH_4$ were added in parts. This was then brought to reflux for 3 hours. After having been cooled, water was added and the precipitate obtained was filtered and recrystallized in isopropanol. Weight obtained: 3 g (yield: 43%); mp=187°-190° C.; IR VOH 3400-3200 $cm^{-1}$; $V_{c=o}$=1610 $cm^{-1}$ NMR $CDCP_3$) δ in ppm in relation to TMS: 4H at 1 to 2.76 m; 4H from 3.2 to 4.4 (m, of which 1H is exchangeable), 1H to 4.9 (dd) 1H to 6.8 (s), 8H from 7.2 to 8.2 (m).

| Elemental Analysis | C % | H % | O % |
|---|---|---|---|
| calculated: | 74.52 | 5.63 | 19.85 |
| found: | 74.82 | 5.52 | |

Example 21

OXO-4-(OXO-4-PHENYL-2-4H-[1]-BENZOPYRAN-8-YL)-4-BUTEN-2-OIC ACID $C_{19}H_{12}O_5$ MW = 320.29 [FORMULA 91]

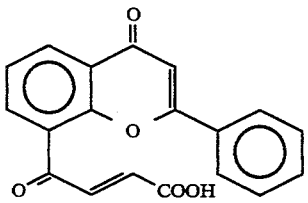

A mixture of 2 g (0.0076 mole) of acetyl-8-phenyl-2-4H-[1]-benzopyranone-4, 1.4 g (0,019 mole) of glyoxylic acid and 25 ml of acetic acid was brought to reflux for 2 hours. This was then poured into water and the precipitate formed was filtered. This was heat dissolved with a solution of 5% $NaHCO_3$ and acidified using acetic acid. The precipitate was filtered, washed with water and recrystallized in the dioxanehexane mixture. Weight obtained: 0.5 g (yield: 20 6%); mp=217°-218° C.; IR $V_{c=o}$ (acid) 1710 $cm^{-1}$, $V_{c=o}$ (ketone)=1760 $cm^{-1}$, $V_{c=o}$(pyrone)=1620 $cm^{-1}$; NMR (DMSO) δ in ppm in relation to TMS 1H to 3.8 (exchangeable), 11H from 6.5 to 8.5 (m).

| Elemental Analysis | C % | H % | O % |
|---|---|---|---|
| calculated: | 71.24 | 3.78 | 24.98 |
| found: | 71.17 | 3.52 | |

Example 22

(OXO-4-PHENYL-2-4H-[1]-BENZOPYRAN-8-YL)-2-HYDROXY-2-ACETIC ACID $C_{17}H_{12}O_5$ MW = 296.28 [FORMULA 92]

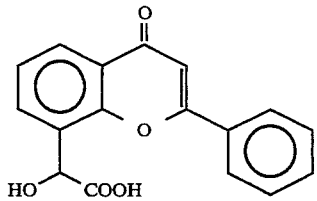

A mixture of 8.75 g (0.134 mole) of potassium cyanide, 125 ml of water, 1.25 1 of dioxane, 53 g (0.5 mole) of $Na_2CO_3$ and 15.32 g (0.061 mole) of oxo-4-phenyl-2-4H-benzopyran-8-carboxaldehyde was stirred at room temperature for 1 hour. 75 ml of acetic acid were then added and this was stirred for 6 hours at room temperature. It was poured into 4 liters of water. The precipitate obtained was washed with water and recrystallized in an acetic acid-water mixture. Weight obtained: 2.5 g (Yield: 14%); IR V OH=3450 $cm^{-1}$, $V_{c=o}$ (acid)=1720 $cm^{-1}$, $V_{c=o}$ (pyrone)=1620 $cm^{-1}$; NMR (DMSO) δ in ppm in relation to TMS: 1H at 3.4 (exchangeable), 1H at 5.6 (s), 1H at 7(s), 9H at 7.3 to 8.3 (m, of which 1H is exchangeable).

| Elemental Analysis | C % | H % | O % |
|---|---|---|---|
| calculated: | 68.92 | 4.08 | 27.00 |
| found: | 68.98 | 4.19 | |

Example 23

(OXO-4-PHENYL-2-4H-[1]-BENZOPYRAN-8-YL)-2-HYDROXY-2-ETHYL ACETATE $C_{19}H_{16}O_5$ MW = 324.32 [FORMULA 93]

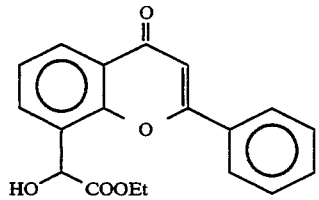

A mixture of 29 g (0.098 mole) of (oxo-4-phenyl-2-4H-[1]-benzopyran-8-yl)-2-hydroxy-2 acetic acid and 35 ml of concentrated $H_2SO_4$ in 585 ml of ethanol are brought to reflux for 5 hours. The mixture was then poured into water, extracted using ethyl acetate, dried, evaporated and the white solid obtained was recrystallized in MIBKhexane. Weight obtained: 20.3 g (Yield: 64%); $MP_K$=135° C.; IR: V OH=3420 $cm^{-1}$, $V_{c=o}$ (ester)=1730 $cm^{-1}$, $V_{c=o}$ (pyrone)=1640 $cm^{-1}$.

Example 24

(OXO-4-PHENYL-2-4H-[1]BENZOPYRAN-8-YL)-2-OXO-2-ETHYL ACETATE $C_{19}H_{14}O_5$ MW = 322.3 [FORMULA 94]

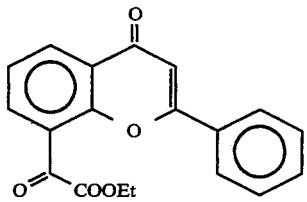

0.79 g (0.0077 mole) of $CrO_3$ and 0.84 g (0.0077 mole) of chlorotrimethylsilane were dissolved in 10 ml of methylene chloride. A solution of 2.5 g (0.0077 mole) of (oxo-4-phenyl-2-4H-[1]benzopyran-8-yl)-2-hydroxy-2-ethyl acetate in 20 ml of methylene chloride was added while cooling the red solution obtained. This was stirred at room temperature for 3 hours 50 minutes. The medium was then passed on a silica column and eluted with $CHCl_3$. This was evaporated and the residue was recrystallized in hexane. Weight obtained: 0.9 g (Yield: 36.3%); $MP_K$=85°-90° C.; IR $V_{c=o}$ (ester)=1730 $cm^{-1}$, $V_{c=o}$ketone)=1690 $cm^{-1}$, $V_{c=o}$(pyrone)=1640 $cm^{-1}$, NMR ($CDCl_3$), δ in ppm in relation to TMS: 3H to 1.3 (t), 2H to 4.3 (q), 1H to 6.8 (s), 8H to 7.25 to 8.7 (m).

Example 25

(OXO-4-PHENYL-2-4H[1]BENZOPYRAN-8-YL)-2-OXO-2-ACETATE ACID $C_{17}H_{10}O_5$ MW = 294.25 [FORMULA 95]

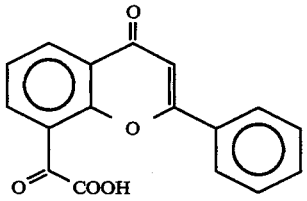

The mixture of 9.3 g (0.0288 mole) of (oxo-4-phenyl-2-4H-[1]benzopyran-8-yl)-2-oxo-2 acetate, 4.85 g (0.057 mole) of sodium bicarbonate, 150 ml of ethanol and 115 ml of water was refluxed for 4 hours 30 minutes. The ethanol was then evaporated, 150 ml of water were added, the mixture was acidified with ½ HCl and the precipitate obtained was filtered and recrystallized in dioxane. Weight obtained: 2.3 g (Yield 27%), $MP_G$=232°-235° C., IR $V_{c=o}$ (acid)=1740 $cm^{-1}$, $V_{c=o}$ (ketone)=1690 $cm^{-1}$, $V_{c=o}$ (pyrone)=1660 $cm^{-1}$. NMR (DMSO) δ in ppm in relation to TMS: 1H to 7.3 (s), 9H to 7.4 to 8.5 (m, 1H of which is exchangeable).

| Elemental Analysis | C % | H % | O % |
|---|---|---|---|
| calculated: | 69.39 | 3.91 | 27.19 |
| found: | 69.11 | 3.95 | |

Example 26

METHYL-2-(OXO-4-PHENYL-2-4H-[1]BENZOPYRAN-8-Y)-2-METHYL PROPANOATE $C_{20}H_{18}O_4$ MW = 322.34 [FORMULA 96]

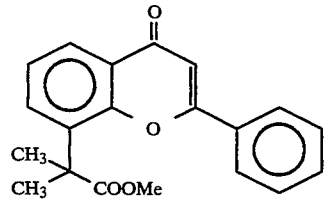

A solution of 6.7 g (0.023 mole) of oxo-4-phenyl-2-4H-[1]benzopyran-8-methyl acetate in 120 ml of DMF was added slowly to a suspension of 2.33 g (0.0485 mole of sodium hydride in 10 ml of DMF. This was stirred for one hour at room temperature, then 6.6 cm (0.1 mole) of methyl iodide in 5 ml of DMF was added dropwise. This was stirred for 6 hours at room temperature and then 6.6 ml of $ClH_3$ in 5 ml of DMF was added. This was stirred for one night, 15 ml of acetic acid were added, it was concentrated to 50 ml, water was added and the ethyl acetate was extracted. This was dried, evaporated under a vacuum and recrystallized in methanol. Weight obtained: 3.5 g (Yield 42%); $MP_K$=157° C.; IR $V_{c=o}$ (ester)=1720 $cm^{-1}$, $V_{c=o}$ (pyrone)=1650 $cm^{-1}$; NMR ($CDCl_3$) δ in ppm in relation to TMS: 6H to 1.75 (s), 3H to 3.6 (s), 1H to 6.87 (s), 8H to 7.2 to 8.4 (m).

Example 27

METHYL-2-(OXO-4-PHENYL-2-4H-[1]-BENZOPYRAN-8-YL)-2-PROPIONIC ACID $C_{19}H_{16}O_4$ MW = 308.318 [Formula 97]

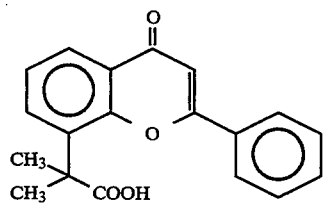

A mixture of 5.7 g (0.0177 mole) of methyl2-(oxo-4-phenyl-2-4H-[1]benzopyran-8-yl)-2-methyl propanoate, 95 ml of acetic acid, 95 ml of concentrated sulfuric acid and 95 ml of concentrated hydrochloric acid were refluxed for 2 hours. This was then stirred for 12 hours at room temperature and brought again to reflux for 3 hours. It was cooled and the precipitate formed was filtered and stabilized in 250 ml of a 5% bicarbonate solution. It was acidified with ½ HCl and the precipitate was dried, washed with water and recrystallized in acetic acid. Weight obtained: 3.1 g (Yield: 56.8%); $MP_G$=255-260; IR $V_{c=o}$ (acid)=1720 $cm^{-1}$, $V_{c=o}$ (pyrone)=1620 $cm^{-1}$; NMR ($CF_3COOD$) δ in ppm in relation to TMS: 6H to 2 (s), 9H from 7.6 to 8.6 (m), 1H to 11.7 (exchangeable).

| Elemental Analysis | C % | H % | O % |
|---|---|---|---|
| calculated: | 74.01 | 5.23 | 20.76 |

-continued

| Elemental Analysis | C % | H % | O % |
|---|---|---|---|
| found: | 73.93 | 5.25 | |

Example 28

OXO-4-PHENYL-2-4H[1]-BENZOPYRAN-8-CARBOXALDEHYDE OXIME (8)

$C_{16}H_{11}NO_3$ MW = 265.256 [Formula 98]

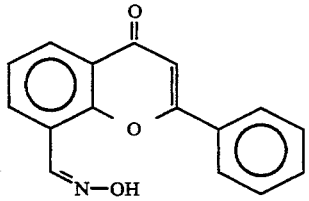

A mixture of 10 g (0.04 mole) of oxo-4-phenyl-2-4H-[1]benzopyran-8-carboxaldehyde, 3.7 g (0.054 mole) of hydroxylamine hydrochlorate, 7.1 g (0.10 mole) of sodium acetate, 20 ml of water and 40 ml of ethanol was brought to reflux for 1 hours. After cooling, the product formed was dried and recrystallized in dioxane. Weight obtained: 6.3 g (Yield: 59.4%); $MP_G$=230°-238° C.; IR V OH=3200 to 2800 $cm^{-1}$, $V_{c=0}$; NMR ($CF_3COOD$), δ in ppm in relation to TMS: 10 H from 7.8 to 9.5 (m).

| Elemental Analysis | C % | H % | N % | O % |
|---|---|---|---|---|
| calculated: | 72.44 | 4.18 | 5.28 | 18.10 |
| found: | 72.74 | 4.24 | 5.03 | |

Using the same method, the following compound was prepared:

ACETYL-8-PHENYL-2-4H-[1]-BENZOPYRANONE-4-OXIME (8)

$C_{17}H_{13}NO_3$ MW = 279.282 [Formula 99]

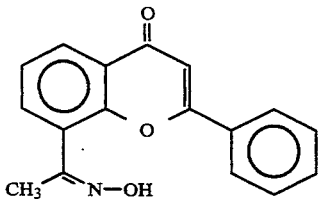

| Elemental Analysis | C % | H % | N % | O % |
|---|---|---|---|---|
| calculated: | 73.10 | 4.69 | 5.02 | 17.19 |
| found: | 73.00 | 4.70 | 4.99 | |

Example 29

(MORPHOLIN-4-YL)-3-(OXO-4-PHENYL-2-4H-[1]-BENZOPYRAN-8-YL)-2-GLUTARONITRILE $C_{24}H_{21}N_3O_3$ MW = 399.43 [Formula 100]

-continued

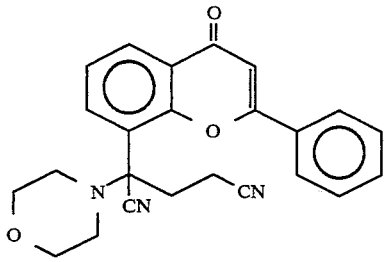

A solution of 1.33 g (0.025 mole) of acrylonitrile in 10 ml of dioxane was added dropwise to a mixture of 7 g (0.02 mole) of (morpholin-4-yl)-3-(oxo-4-phenyl-2-4H-[1]benzopyran-8-yl)-2 acetonitrile. After 18 hours at room temperature, a slightly insoluble material was filtered and evaporated under a vacuum. The residue was recrystallized in isopropanol. Weight obtained: 3.1 g (Yield: 38.8%); $MP_K$=110° C.; IR V C=N=2250 $cm^{-1}$, V C=1640 $cm^{-1}$; NMR ($CDCl_3$) δ in ppm in relation to TMS: 8H from 1.8 to 3.2 (m); 4H to 3.9 (t), 1H to 7 (s), 8H from 7.4 to 8.6 (m).

Example 30

OXO-4-(OXO-4-PHENYL-2-4H-[1]-BENZOPYRAN-8-YL)-4-BUTYRIC ACID $C_{19}H_{14}O_5$ MW = 322.3 [Formula 101]

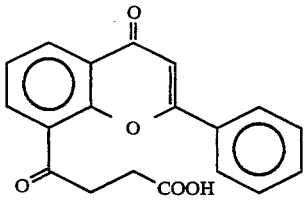

A mixture of 3 g (0.0075 mole) of the compounf od Example 29, 30 ml of 6N hydrochloric acid and 30 ml of acetic acid was refluxed for 4 hours. This was then poured into water and ice, the product was dried, it was replaced in a solution of 5% $NaHCO_3$ and acidified. The precipitate formed was dried and recrystallized in the MIBK-dioxane mixture. Weight obtained: 1.1 g (Yield: 45.5%); $MP_F$=207°-209° C.; IR $V_{c=o}$ (acid=1720 $cm^{-1}$, $V_{c=o}$ (ketone)=1680 $cm^{-1}$, $V_{c=o}$ (pyrone)=1620 $cm^{-1}$; NMR (DMSO) δ in ppm in relation to TMS: 4H from 2.4 to 3.6 (m), 1H to 7.1 (s), 8H from 7.4 to 8.4 (m), 1H to 12.1 (exchangeable).

| | Elemental analysis | | |
|---|---|---|---|
| | C% | H% | O% |
| calculated: | 70.80 | 4.38 | 24.82 |
| found: | 70.50 | 4.43 | |

Example 31

HYDROXY-4-(OXO-4-PHENYL-2-4H-[1]-BENZOPYRAN-8-Y)-BUTYRIC ACID $C_{19}H_{16}O_5$ MW = 324.32 [Formula 102]

-continued

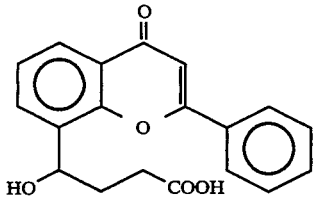

By treating 5 g (0.0155 mole) of the product of Example 30 with 9.5 g (0.0468 mole) of aluminum isopropylate in 100 ml of isopropanol and 40 ml of dioxane for 6 hours at reflux, 1.9 g of isopropyl hydroxy ester ($MP_K$=145° C.) was obtained after recrystallization in hexane. This was placed in 10 ml of water, 17 m with 0.45 g of sodium bicarbonate. The medium was brought to reflux for 4 hours 30 minutes, evaporated and the residue was replaced in water. The insoluble material was filtered, acidified with acetic acid, dried, and recrystallized in dioxane. Weight obtained: 0.7 g $MP_G$=198°-202° C.; IR V OH=3350 $cm^{-1}$, $V_{c=o}$ (acid)=1700 $cm^{-1}$, $V_{c=o}$ (pyrone)=1620 $cm^{-1}$; NMR (DMSO) δ in ppm in relation to TMS: 4H from 1.7 to 2.9 (m), 2H from 5.3 to 5.8 (m, of which 1H is exchangeable), 1H to 7.1 (s), 8H from 7.4 to 8.4 (m), 1H to 11.8 (exchangeable).

| | Elemental analysis | | |
|---|---|---|---|
| | C% | H% | O% |
| calculated: | 70.36 | 4.97 | 24.67 |
| found: | 70.56 | 4.72 | |

Example 32

ACETAMIDO-2-ETHOXYCARBONYL-2-(OXO-4-PHENYL-2-4H-[1]-BENZOPYRAN-8-YL)-2 ETHYL PROPIONATE $C_{25}H_{25}NO_7$ MW = 451.46 [Formula 103]

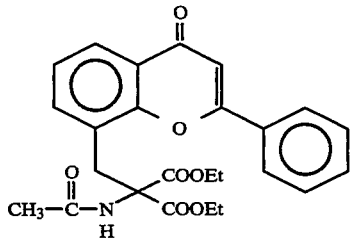

17.5 g (0.08 mole) of diethyl acetamidomalonate was added at 20° C. in 20 minutes to a suspension of 3 g (0.08 mole) of sodium hydride in 100 ml of toluene. This was left under stirring for 1 hour, then 25 g (0.08 mole) of bromomethyl-8-phenyl-2-4H-[1]benzppyranone-4 were added in one hour. This was brought to a reflux for 8 hours and then hot filtered. the filtrate was evaporated under a vacum, the residue was replaced in water, the solid was dried and recrystallized in ethanol. Weight obtained: 24.4 g (Yield: 67.6%); $MP_K$=200° C.; IR V NH=3370 $cm^{-1}$ $V_{c=o}$ (ester)=1720 $cm^{-1}$ and 1760 $cm^{-1}$, $V_{c=o}$ (amide)=7670 $cm^{-1}$, $V_{c=o}$ (pyrone)=1640 $cm^{-1}$.

Example 33

AMINO-2-(OXO-4-PHENYL-2-4H-[1]-BENZOPYRAN-8-YL)-3-PROPIONIC ACID HYDROCHLORATE

-continued $C_{18}H_{16}ClNO_4$ MW = 345.78 [Formula 104]

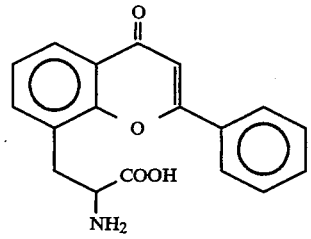

A mixture of 10 g (0.022 mole) of the compound of Example 32 and 400 ml of ½ HCl was brought to reflux for 4 hours. After a night of rest, the precipitate formed was dried and recrystallized in the ACOH-water mixture. Weight obtained: 4.4 g (Yield: 57.6%), $MP_G$=243° C.; IR V OH, $NH_3(+)$=3500-2500 $cm^{-1}$, $V_{c=o}$ (acid)=1740 $cm^{-1}$, $V_{c=o}$ (pyrone)=1625 $cm^{-1}$; NMR (DMSO) δ in ppm in relation to TMS: 3H from 3.4 to 4.4 (m), 1H to 7.1 (s), 12H from 7.4 to 10 (m, of which 4H are exxchangeable).

| | Elemental analysis | | | | |
|---|---|---|---|---|---|
| | C% | H% | Cl% | N% | O% |
| calculated: | 62.52 | 4.66 | 10.26 | 4.05 | 18.51 |
| found: | 62.66 | 4.89 | 10.35 | 4.11 | |

Following the experimental protocol outlined in Example 1 supra, the following compounds were prepared.

2-(2-AMINOPHENYL)-4-OXO-4H-[1]-BENZOPYRAN-8-ACETIC ACID $C_{17}H_{13}NO_4$ MW = 295.28 [Formula 105]

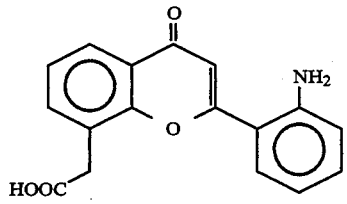

$PF_G$=189° $V_c$; IR νC=o (acid) 1710 $cm^{-1}$, $V_{c=0}$ (pyrone)=1610 $cm^{-1}$

| | Elemental analysis | | | |
|---|---|---|---|---|
| | C% | H% | N% | O% |
| calculated: | 69.14 | 4.44 | 4.74 | 21.61 |
| found: | 68.92 | 4.25 | 4.45 | |

2-(2-CHLOROPHENYL)-4-OXO-4H-[1]-BENZOPYRAN-8-ACETIC ACID $C_{17}H_{11}ClO_4$ MW = 314.715 [Formula 106]

-continued

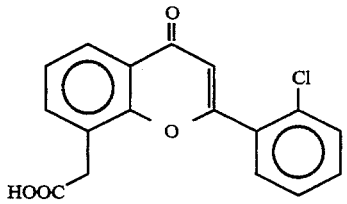

$PF_G$=169° C.; IR $V_{c=o}$ (acid)=1710 $cm^{-1}$, $V_{c=o}$ (pyrone)=1620 $cm^{-1}$; NMR (DMSO) δ in ppm relative to TMS: 2 H at 4.3 (s), 8 H from 7.5 to 8.7 (m), 1 H at 11.7 (exchangeable).

| | Elemental analysis | | | |
|---|---|---|---|---|
| | C% | H% | Cl% | O% |
| calculated: | 64.87 | 3.52 | 11.27 | 20.34 |
| found: | 65.09 | 3.48 | 11.53 | |

2-(3-CHLOROPHENYL)-4-OXO-4H-[1]-BENZOPYRAN-8-ACETIC ACID $C_{17}H_{11}ClO_4$ MW = 314.715 [Formula 107]

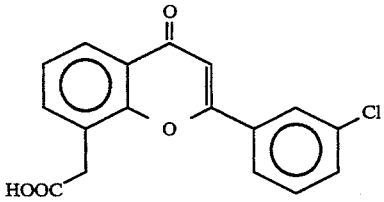

$PF_G$=220°-222° C.; IR $V_{c=o}$ (acid)=1730 $cm^{-1}$; $V_{c=o}$ (pyrone)=1620 $cm^{-1}$; NMR (DMSO) δ in ppm relative to TMS: 2 H at 4 (s), 1 H from 7.5 (s), 7 H from 7.3 to 8.3 (m), 1 H at 13 (exchangeable).

| | Elemental analysis | | | |
|---|---|---|---|---|
| | C% | H% | Cl% | O% |
| calculated: | 64.87 | 3.52 | 11.27 | 20.34 |
| found: | 64.59 | 3.53 | 11.28 | |

2-(2-ACETAMIDOPHENYL)-4-OXO-4H-[1]-BENZOPYRAN-8-ACETIC ACID $C_{19}H_{15}NO_5$ MW = 337.318 [Formula 108]

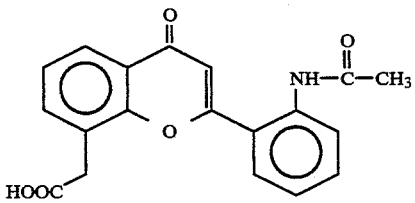

$PF_G$=196°-201° C.; IR $V_{c=o}$ (acid)=1720 $cm^{-1}$; $V_{c=o}$ (amide)=1660 $cm^{-1}$; $V_{c=o}$ (pyrone)=1620 $cm^{-1}$; NMR (DMSO) δ in ppm relative to TMS: 3 H at 2 (s), 2 H at 3.8 (s), 1 H at 6.5 (s), 7 H from 7.3 to 8.2 (m), 1 H at 8.8 (exchangeable), 1 H at 11.5 (exchangeable).

| | Elemental analysis | | | |
|---|---|---|---|---|
| | C% | H% | Cl% | O% |
| calculated: | 67.65 | 4.48 | 4.15 | 23.72 |

-continued

| | Elemental analysis | | | |
|---|---|---|---|---|
| | C% | H% | Cl% | O% |
| found: | 67.42 | 4.24 | 4.11 | |

2-(4-ACETYLPHENYL)-4-OXO-4H-[1]-BENZOPYRAN-8-ACETIC ACID $C_{19}H_{14}O_5$ MW = 322.302 [Formula 110]

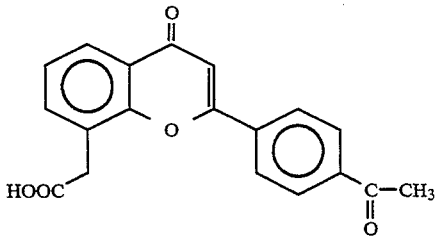

$PF_G$=253°-255° C.; IR $V_{c=o}$ (pyrone)=1620 $cm^{-1}$; NMR ($CF_3COOD$) δ in ppm relative to TMS: 3 H at 2.8 (s), 2 H at 4.3 (m), 8 H from 7.7 to 8.5 (m).

| | Elemental analysis | | |
|---|---|---|---|
| | C% | H% | O% |
| calculated: | 70.80 | 4.38 | 24.82 |
| found: | 70.61 | 4.31 | |

2-(4-ACETAMIDOPHENYL)-4-OXO-4H-[1]-BENZOPYRAN-8-ACETIC ACID $C_{19}H_{15}NO_5$ MW = 337.318 [Formula 111]

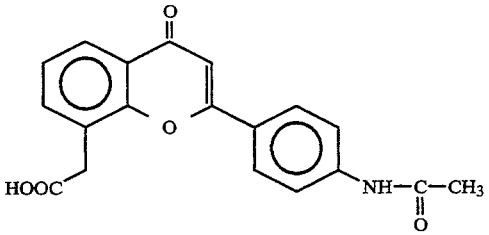

$PF_G$=284°-288° C. IR $V_{c=o}$ (acid)=1720 $cm^{-1}$; $V_{c=o}$ (amide+pyrone)=1630 $cm^{-1}$; NMR (DMSO) δ in ppm relative to TMS: 3 H at 2 (s), 2 H at 4 (s), 1 H at 6.8 (s), 7 H from 7.1 to 8.1 (m), 1 H at 9.8 (exchangeable), 1 H at 12 (exchangeable).

| | Elemental analysis | | | |
|---|---|---|---|---|
| | C% | H% | N% | O% |
| calculated: | 67.65 | 4.48 | 4.15 | 23.72 |
| found: | 67.70 | 4.40 | 4.12 | |

2-(2-DIETHYLAMINOETHOXYPHENYL)-4-OXO-4H-[1]-BENZOPYRAN-8-ACETIC ACID $C_{23}H_{25}ClNO_5$ MW = 431.903 [Formula 112]

(chlorhydrate)

-continued

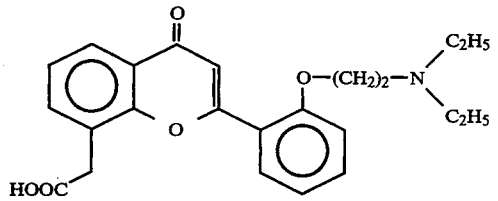

$PF_G$=1780°-182° C. $C_1$ (chlorhydrate); IR $V_{c=o}$ (acid)=1720 $cm^{-1}$; $V_{c=o}$ (pyrone)=1640 $cm^{-1}$; NMR (DMSO) δ in ppm relative to TMS: 6 H at 1 (t), 6 H from 2.8 to 3.8 (m), 4 H from 3.9 to 4.2 (m), 8 H from 6.8 to 8 (m), 1 H at 11 (exchangeable).

| | Elemental analysis | | | | |
|---|---|---|---|---|---|
| | C% | H% | Cl% | N% | O% |
| calculated: | 63.96 | 6.07 | 8.21 | 3.24 | 18.52 |
| found: | 63.96 | 6.12 | 8.19 | 3.24 | |

| | Elemental anelysis | | | | |
|---|---|---|---|---|---|
| | C% | H% | Cl% | N% | O% |
| calculated: | 56.76 | 2.80 | 9.86 | 3.89 | 26.69 |
| found: | 56.82 | 2.69 | 9.78 | 3.90 | |

$PF_G$=232°-234° C.; IR $V_{c=o}$ (acid)=1720 $cm^{-1}$; $V_{c=o}$ (pyrone)=1640 $cm^{-1}$; NMR (DMSO) δ in ppm relative to TMS: 2 H at 4 (s), 7 H from 7 to 8.8 (m), 1 H at 12.1 (exchangeable).

| | Elemental anelysis | | | | |
|---|---|---|---|---|---|
| | C% | H% | Cl% | N% | O% |
| calculated: | 56.76 | 2.80 | 9.86 | 3.89 | 26.69 |
| found: | 56.82 | 2.69 | 9.78 | 3.90 | |

2-(2-4-DIMETHOXYPHENYL)-4-OXO-4H-[1]-BENZOPYRAN-8-ACETIC ACID $C_{19}H_{16}O_6$ MW = 340.185 [Formula 114]

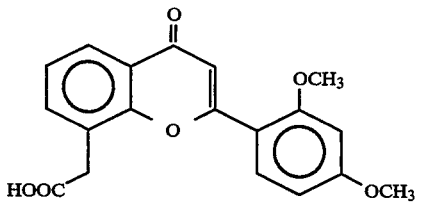

$PF_G$=225°-227° C.; IR $V_{c=o}$ (acid)=1710 $cm^{-1}$; $V_{c=o}$ (pyrone)=1620 $cm^{-1}$; NMR (DMSO) δ in ppm relative to TMS: 2 H at 3.5 (s), 3 H at 3.9 (s), 3 H at 4 (s), 7 H from 6.8 to 8, 1 H at 12.2 (exchangeable).

| | Elemental analysis | | |
|---|---|---|---|
| | C% | H% | O% |
| calculated: | 67.05 | 4.74 | 28.21 |
| found: | 67.23 | 4.63 | |

2-(4-DIETHYLAMINOETHOXYPHENYL)-4-OXO-4H-[1]-BENZOPYRAN-8-ACETIC ACID

-continued $C_{23}H_{26}ClNO_2$ MW = 431.92 [Formula 115]

(chlorhydrate)

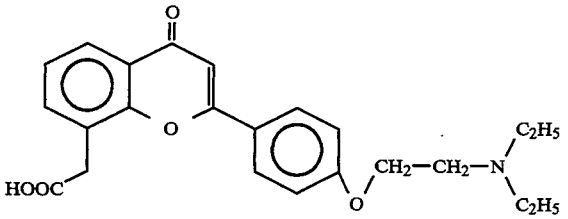

$PF_G$=194°-199° C. (chlorhydrate); IR $V_{c=o}$ (acid)=1720 $cm^{-1}$; $V_{c=o}$ (pyrone)=1630 $cm^{-1}$; NMR (DMSO) δ in ppm relative to TMS: 6H at 1 (t), 6H from 2.8 to 3.8 (m), 4H from 3.9 to 4.7 (m), 8H from 6.8 to 8.2 (m), 2H from 10 to 12 (exchangeable).

| | Elemental analysis | | | | |
|---|---|---|---|---|---|
| | C% | H% | Cl% | N% | O% |
| calculated: | 63.96 | 6.07 | 8.21 | 3.24 | 18.57 |
| found: | 63.50 | 6.04 | 8.30 | 3.45 | |

2-(4-CARBAMOYLPHENYL)-4-OXO-4H-[1]-BENZOPYRAN-8-ACETIC ACID $C_{18}H_{13}NO_5$ MW = 323.292 [Formula 116]

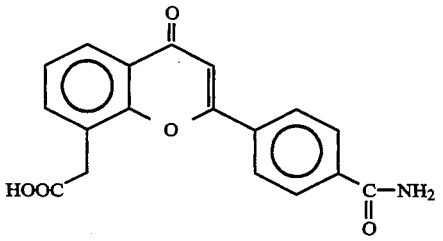

$PF_G$=228°-290° ; IR $V_{c=o}$ (acid)=1710 $cm^{-1}$; $V_{c=o}$ (amide+pyrone)=1640 $cm^{-1}$

| | Elemental analysis | | | |
|---|---|---|---|---|
| | C% | H% | N% | O% |
| calculated: | 66.87 | 4.05 | 4.33 | 24.75 |
| found: | 66.35 | 4.35 | 4.46 | |

(METHYL-2-THIAZOLYL-4)-4-PHENYL-2-OXO-4-4H[1]BENZOPYRAN-8-ACETIC ACID $C_{21}H_{15}NO_4S$ MW = 377.398 [Formula 117]

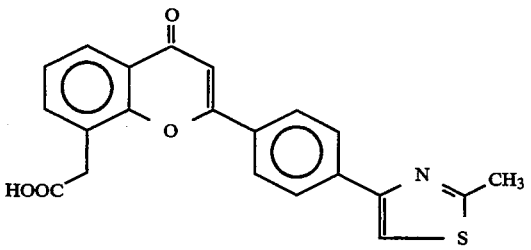

$PF_G$=246.248° C.; IR $V_{c=o}$ (acid)=1720 $cm^{-1}$; $V_{c=o}$ (pyrone)=1620 $cm^{-1}$; NMR (DMSO) δ in ppm relative to TMS: 3H at 4 (s), 2H at 3.8, 8H from 7.1 to 8.1 (m), 1 H at 12.6 (exchangeable).

| | Elemental analysis | | | | |
|---|---|---|---|---|---|
| | C% | H% | N% | O% | S% |
| calculated: | 66.83 | 4.01 | 3.71 | 16.96 | 8.50 |
| found: | 66.73 | 3.95 | 3.66 | | 8.56 |

2-(3-DIMETHYLTRIAZENYLPHENYL)-4-OXO-4H-[1]-BENZOPYRAN-8-ACETIC ACID $C_{19}H_{17}N_3O_4$ MW = 351.35 [Formula 118]

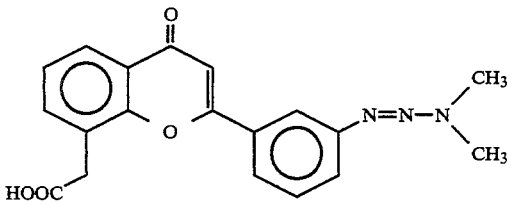

$PF_G$=173°-175° C.; IR $V_{c=o}$ (acid)=1710 $cm^{-1}$; $V_{c=o}$ (pyrone)=1620 $cm^{-1}$; NMR (DMSO) δ in ppm relative to TMS: 6 H at 3.25 (s), 2 H at 4 (s), 1 H at 7 (s), 7 H from 7.2 to 8 (m), 1 H at 12.3 (exchangeable).

| | Elemental analysis | | | |
|---|---|---|---|---|
| | C % | H % | N % | O % |
| calculated: | 64.95 | 4.88 | 11.96 | 18.22 |
| found: | 64.72 | 4.85 | 12.04 | |

2-(2-AMINO-4-THIAZOLYLPHENYL)-4-OXO-4H-[1]-BENZOPYRAN-8-ACETIC ACID $C_{20}H_{14}O_4S$ MW = 378.388 [Formula 119]

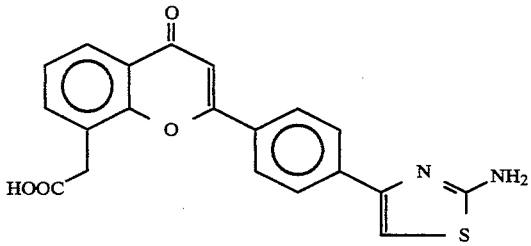

$PF_G$=263°-265° C.; IR $V_{c=o}$ (acid)=1710 $cm^{-1}$; $V_{c=o}$ (pyrone)=1620 $cm^{-1}$; NMR (DMSO) δ in ppm relative to TMS: 2 H at 4 (s), 11 H from 7 to 8.2 (m, with 2 H exchangeabe), 1 H at 12.9 (exchangeable).

| | Elemental analysis | | |
|---|---|---|---|
| | C % | H % | O % |
| calculated: | 67.05 | 4.75 | 28.21 |
| found: | 67.70 | 4.54 | 7.12 |

2-(3,5-DIMETHOXYPHENYL)-4-OXO-4H-[1]-BENZOPYRAN-8-ACETIC ACID $C_{19}H_{16}O_6$ MW = 340.318 [Formula 120]

-continued

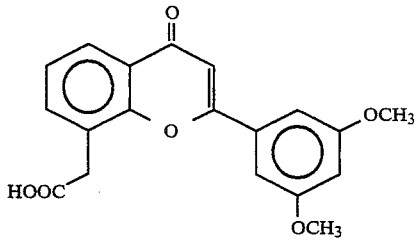

$PF_G$=261°-263° C.; IR $V_{c=o}$ (acid)=1720 $cm^{-1}$; $V_{c=o}$ (pyrone)=1630 $cm^{-1}$; NMR (DMSO) δ in ppm relative to TMS: 6 H at 3.9 (s), 2 H at 4 (s), 7 H from 6.5 to 8 (m), 1 H at 12.9 (exchangeable).

| | Elemental analysis | | |
|---|---|---|---|
| | C % | H % | O % |
| calculated: | 67.05 | 4.74 | 28.21 |
| found: | 67.20 | 4.54 | |

2-(4-PYRIDYL)-4-OXO-4H-[1]-BENZOPYRAN-8-ACETIC ACID $C_{16}H_{11}NO_4$ MW = 281.256 [Formula 121]

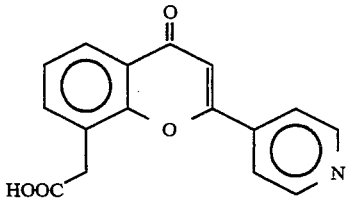

$PF_G$=275°-277° C.; IR $V_{c=o}$ (acid) 1720 $cm^{-1}$; $V_{c=o}$ (pyrone)=1600 $cm^{-1}$; NMR (DMSO+$CF_3$-COOD) δ in ppm relative to TMS: 2 H at 4 (s), 8 H from 7.3 to 8.8 (m).

| | Elemental analysis | | | |
|---|---|---|---|---|
| | C % | H % | N % | O % |
| calculated: | 68.32 | 3.94 | 4.98 | 22.76 |
| found: | 67.94 | 4.09 | 5.12 | |

2-(2-PYRIDYL)-4-OXO-4H-[1]-BENZOPYRAN-8-ACETIC ACID $C_{16}H_{11}NO_4$ MW = 281.256 [Formula 122]

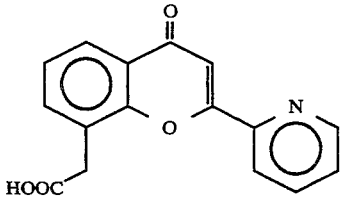

$PF_G$=221°-223° C.; IR $V_{c=o}$ (acid)=172-1740 $cm^{-1}$; $V_{c=o}$ (pyrone)=1640 $cm^{-1}$; NMR (DMSO) δ in ppm relative to TMS: 2 H at 4.1 (s), 1 H at 7.2 (s), 7 H from 7.25 to 9 (m), 1 H at 13 (exchangeable).

| | Elemental analysis | | | |
|---|---|---|---|---|
| | C % | H % | N % | O % |
| calculated: | 68.32 | 3.94 | 4.98 | 22.76 |
| found: | 68.50 | 3.89 | 4.86 | |

2-(4-HEXYLPHENYL)-4-OXO-4H-[1]-BENZOPYRAN-8-ACETIC ACID $C_{23}H_{24}O_4$ MW = 364.422 [Formula 123]

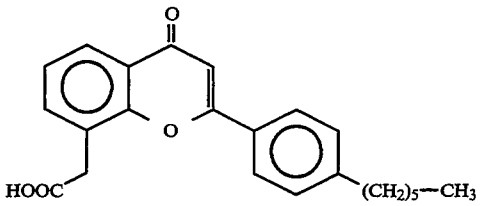

$PF_G$=154°-156° C.; IR $V_{c=o}$ (acid)=1720 $cm^{-1}$; $V_{c=o}$ (pyrone)=1620 $cm^{-1}$; NMR (DMSO) δ in ppm relative to TMS: 13 H from 0.7 to 2.8 (m), 2 H at 4 (s), 1 H at 7 (s), 7 H from 7.2 to 8.1 (m), 1 H at 12.9 (exchangeable).

| | Elemental analysis | | |
|---|---|---|---|
| | C % | H % | O % |
| calculated: | 75.80 | 6.64 | 17.56 |
| found: | 75.50 | 6.49 | |

2-(3-METHYLPHENYL)-4-OXO-H-[1]-BENZOPYRAN-8-ACETIC ACID $C_{18}H_{14}O_4$ MW = 294.292 [Formula 124]

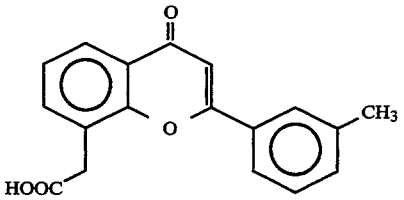

$PF_G$=252°-254° C.; IR $V_{c=o}$ (acid)=1720 $cm^{-1}$; $V_{c=o}$ (pyrone)=1620 $cm^{-1}$; NMR ($CF_3COOD$) δ in ppm relative to TMS: 3 H at 2.55 (s), 2 H at 4.5 (m), 8 H from 7.5 to 8.6 (m).

| | Elemental analysis | | |
|---|---|---|---|
| | C % | H % | O % |
| calculated: | 73.46 | 4.80 | 21.75 |
| found: | 73.74 | 4.86 | |

2-(4-BENZOYLPHENYL)-4-OXO-4H-[1]-BENZOPYRAN-8-ACETIC ACID $C_{24}H_{16}O_4$ MW = 384.368 [Formula 125]

-continued

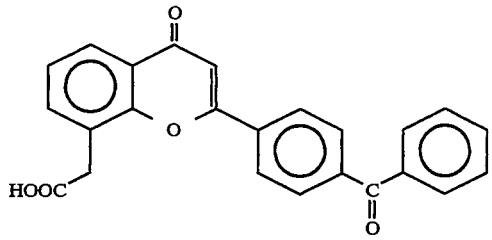

$PF_G$=257°-259° C.; IR $V_{c=o}$ (acid)=1720 $cm^{-1}$; $V_{c=o}$ (benzoyl)=1650 $cm^{-1}$; $V_{c=o}$ (pyrone)=1620 $cm^{-1}$; NMR ($CF_3COOD$) δ in ppm relative to TMS: 2 H at 4.5 (s), 13 H from 7.5 to 8.7 (m).

| | Elemental analysis | | |
|---|---|---|---|
| | C % | H % | O % |
| calculated: | 74.99 | 4.20 | 20.81 |
| found: | 75.11 | 4.09 | |

2-(4-UNDECYLPHENYL)-4-OXO-4H-[1]-BENZOPYRAN-8-ACETIC ACID $C_{28}H_{26}ClNO_5$ MW = 434.552 [Formula 126]

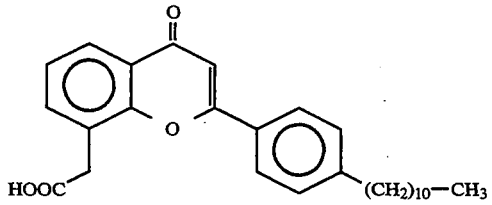

$PF_G$=150°-152° C.; IR $V_{c=o}$ (acid)=1710 $cm^{-1}$; $V_{c=o}$ (pyrone)=1620 $cm^{-1}$; NMR ($CF_3COOD$) δ in ppm relative to TMS: 23 H from 0.6 to 1.7 (m), 2 H at 4.5 (s), 8 H from 7.5 to 8.4 (m).

| | Elemental analysis | | |
|---|---|---|---|
| | C % | H % | O % |
| calculated: | 77.39 | 7.89 | 14.73 |
| found: | 77.34 | 7.87 | |

(NITRO-3-PHENYL-4-PHENYL)-2-OXO-4-4H-[1]-BENZOPYRAN-8-ACETIC ACID $C_{23}H_{15}NO_6$ MW = 401.358 [Formula 127]

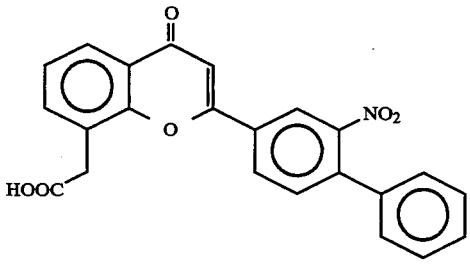

$PF_G$=270°-272° C.; IV $V_{c=o}$ (acid)=1720 $cm^{-1}$ $C_{c=o}$ (pyrone)=1620 $cm^{-1}$; NMR (DMSO) δ in ppm relative to TMS: 2 H at 4 (s), 12 H from 7.2 to 8.7 (m), 1 H at 12.9 (exchangeable).

| | Elemental analysis | | | |
|---|---|---|---|---|
| | C % | H % | N % | O % |
| calculated: | 68.88 | 3.77 | 3.49 | 23.92 |
| found: | 68.72 | 3.66 | 3.34 | |

2-(4-TRIFLUOROMETHYLPHENYL)-4-OXO-4H-[1]-BENZOPYRAN-8-ACETIC ACID $C_{18}H_{11}F_3O_4$ MW = 348.268 [Formula 128]

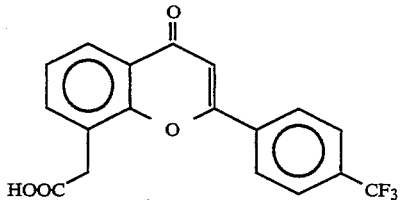

$PF_G$=216°-218° C.; IR $V_{c=o}$ (acid)=1720 $cm^{-1}$; $V_{c=o}$ (pyrone)=1640 $cm^{-1}$; NMR (DMSO) δ in ppm relative to TMS: 2 H at 4 (s), 8 H from 7.1 to 8.4 (m), 1 H at 12.8 (exchangeable).

| | Elemental analysis | | | |
|---|---|---|---|---|
| | C % | H % | F % | O % |
| calculated: | 63.07 | 3.18 | 16.37 | 18.38 |
| found: | 63.02 | 3.32 | 16.37 | |

2-(4-DIMETHYLTRIAZENYLPHENYL)-4-OXO-4H-[1]-BENZOPYRAN-8-ACETIC ACID $C_{19}H_{17}N_3O_4$ MW = 351.35 [Formula 129]

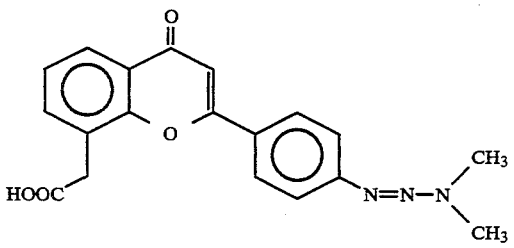

$PF_G$=209°-211° C.; IR $V_{v=o}$ (aci)=1720 $cm^{-1}$; $V_{c=o}$ (pyrone)=1620 $cm^{-1}$; NMR (DMSO) δ in ppm relative to TMS: 6 H at 3.3 (m), 2 H at 4 (s), 1 H at 79 (s), 7 H from 7.2 to 8.1 (m), 1 H at 12.8 (exchangeable).

| | Elemental analysis | | | |
|---|---|---|---|---|
| | C % | H % | N % | O % |
| calculated: | 64.95 | 4.88 | 11.96 | 18.22 |
| found: | 64.75 | 4.95 | 12.25 | |

2-(3-NITRO-4-METHOXYPHENYL)-4-OXO-4H-[1]-BENZOPYRAN-8-ACETIC ACID $C_{18}H_{13}NO_7$ MW = 355.292 [Formula 130]

-continued

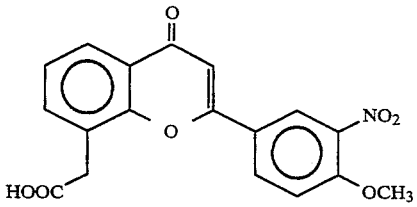

$PF_G$=254°-256° C.; IR $V_{c=o}$ (acid)=1720 $cm^{-1}$; $V_{c=o}$ (pyrone)=1620 $cm^{-1}$; NMR ($CF_3COOD$): 3 H at 4.1 (s), 2 H at 4.3 (s), 8 H from 7.1 to 9 (m).

| | Elemental analysis | | | |
|---|---|---|---|---|
| | C % | H % | N % | O % |
| calculated: | 60.85 | 3.69 | 3.94 | 31.94 |
| found: | 61.07 | 3.68 | 4.16 | |

2-(4-TERBUTYLPHENYL)-4-OXO-4H-[1]-BENZOPYRAN-8-ACETIC ACID $C_{21}H_{20}O_4$ MW = 336.37 [Formula 131]

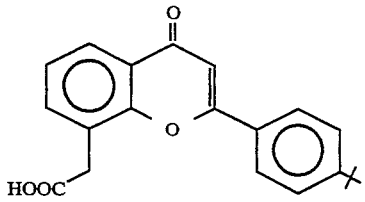

$PF_G$=240°-242° C.; IR $V_{c=o}$ (acid)=1720 $cm^{-1}$; $V_{c=o}$ (pyrone)=1610 $cm^{-1}$; NMR (DMSO) δ in ppm relative to TMS: 9 H at 1.2 (s), 2 H at 4.5 (s), 8 H from 7.1 to 8.3 (m), 1 H at 12.9 (exchangeable).

| | Elemental analysis | | |
|---|---|---|---|
| | C % | H % | O % |
| calculated: | 74.98 | 5.99 | 19.03 |
| found: | 74.76 | 5.85 | |

EXAMPLE

[OXO-4-(THENYL-2)-2-4H-[1]-BENZOPYRAN-8-YL]ACETIC ACID $C_{15}H_{10}O_4S$ MW = 286.31 [Formula 312]

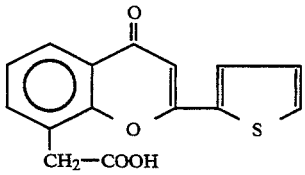

This compound is prepared using the procedure outlined in example 2 of U.S. Pat. No. 4,602,034 using 21.7 g (0/081 mole) of [oxo-4-thenyl-2)-4H-[1]-benzopyran-8-yl]acetonitrile. After treating with sodium bicarbonate, a substance is obtained which is recrystallized in dioxane. Weight obtained: 13.9 g (Yield: 60%), $MP_G$=247°-255° C.

IR: $V_{c=o}$ (pyrone): 1630 $cm^{-1}$, $V_{c=o}$ (acid): 1710 $cm^{-1}$; OH: 2400-2800 $cm^{-1}$, NMR (DMSO) δ in ppm compared with TMS, 2H at 4 (singlet), 1H at 7 (singlet), 6H from 7.3 to 8.2 (multiplet), 1H at 12 (exchangeable with $D_2O$).

EXAMPLE

[METHOXY-3-PHENYL)-2-OXO-4-4H-[1]-BENZOPYRAN-8-YL]ACETIC ACID $C_{18}H_{14}O_5$ MW = 310.31 [Formula 329]

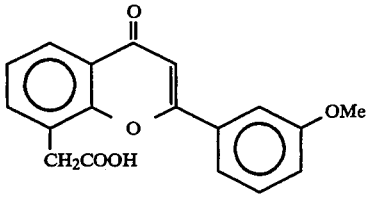

This substance is prepared using the procedure outlined in example 2 of U.S. Pat. No. 4,602,034, from 9.1 g (0.031 mole) of [(methoxy-3-phenyl)-2-oxo-4-4H-[1]-benzopyran-8-yl]-acetonitrile. Weight obtained: 2.2 g. $MP_G$=238°-241° (MiBk). IR: $V_{c=o}$ (pyrone)=1635 $cm^{-1}$, $V_{c=o}$(acid)=1710 $cm^{-1}$. NMR (DMSO), 1H at 3.4 (exchangeable with $D_2O$), 3H at 3.9 (singlet), 2H at 4.02 (singlet), 1H at 7.1 (singlet), 7H from 7.1 to 8.1 (multiplet).

| | Elemental analysis | | |
|---|---|---|---|
| | C % | H % | O % |
| calculated: | 69.67 | 4.55 | 25.78 |
| found: | 69.91 | 4.61 | |

EXAMPLE

[(FURYL-2)-2-OXO-4-4H-[1]-BENZOPYRAN-8-YL]-ACETIC ACID $C_{15}H_{10}O_5$ MW = 270.23 [Formula 339]

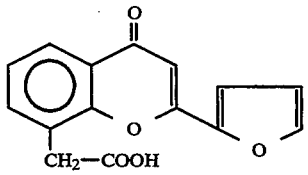

This substance is prepared using the procedure outlined in example 2 of U.S. Pat. No. 4,602,034, from 16 g (0.063 mole) of [(furyl-2)-2-oxo-4-4H-[1]-benzopyran-8-yl]acetonitrile. Weight obtained: 8.5 g (Yield: 49%). $MP_G$=240°-242° C. IR: OH=2800-3200 $cm^{-1}$, $V_{c=o}$ (acid)=1720 $cm^{-1}$, $V_{c=o}$(pyrone)=1650 $cm^{-1}$. NMR (DMSO) δ in ppm compared with TMS, 2H at 4 (singlet), 1H at 6.7 (singlet), 1H from 6.8 to 7 (multiplet), 5H from 7.3 to 8.1 (multiplet), 1H at 12.6 (exchangeable with $D_2O$).

| | Elemental analysis | | |
|---|---|---|---|
| | C % | H % | O % |
| calculated: | 66.67 | 3.73 | 29.60 |
| found: | 66.81 | 3.74 | |

EXAMPLE

[METHYL-4-PHENYL)-2-OXO-4-4H-[1]-BENZOPYRAN-8-YL]ACETIC ACID

-continued $C_{18}H_{14}O_4$ MW = 294.29 [Formula 341]

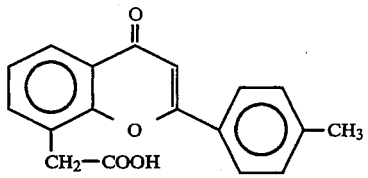

This substance is prepared as in example 2 of U.S. Pat. No. 4,602,034, from 23.5 g (0.085 mole) of [(methyl-4-phenyl)-2-oxo-4-4H-[1]-benzopyran-8-yl]acetonitrile. After treatment with sodium bicarbonate and recrystallization in acetic acid, 15 g of the substance are obtained. (Yield: 59%). $MP_G$=250°-252° C.

IR: V OH=2800-3200 $cm^{-1}$; $V_{c=o}$ (acid)=1720 $cm^{-1}V_{c=o}$(pyrone)=1630 $cm^{-1}$. NMR (DMSO) δ in ppm compared with TMS, 3H at 2.2 (singlet), 2H at 4 (singlet), 1H at 7 (singlet), 7H from 7.2 to 8.1 (multiplet), 1H at 12.7 (exchangeable with $D_2O$).

| | Elemental analysis | | |
|---|---|---|---|
| | C % | H % | O % |
| calculated: | 73.46 | 4.80 | 21.74 |
| found: | 73.77 | 4.94 | |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for treating cancer in a patient in need thereof, comprising coadministering to said patient an effective amount of (i) interleukin-2 or a protein having the in vivo activity of interleukin-2, and (ii) at least one flavonoid compound which has the immunomodulatory activity of (iia) boosting natural activity and (iib) inducing interferon, and (iic) belongs to the family of flavonoids of the formula (I):

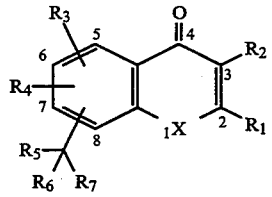

(I)

wherein

X is N, O, Se, or $S(O)_n$, wherein n is 0, 1 or 2;

$R_1$ is H; $C_{1-7}$ alkyl; naphthyl; phenyl; phenyl substituted by at least one member selected from the group consisting of halogens, $C_{1-12}$ alkyl, trifluoromethyl, hydroxyl, $C_{1-6}$ alkoxy, —($C_{1-6}$-alkylene)-$COOR_{10}$, nitro, $C_{1-6}$—(alkyl)-carboylamino, benzoyl, $C_{1-6}$—(alkyl)-carboyl, $CONR_{10}R_{11}$, , where $R_{10}$ and $R_{11}$ are each independently H or $C_{1-6}$ alkyl, $NR_{10}R_{11}$, —N=N—$NR_{10}R_{11}$, phenyl substituted by at least one halogen atom, phenol, —O—($C_{1-6}$ alkylene)—$NR_{10}R_{11}$, thiazolyl, and thiazolyl substituted by $C_{1-6}$ alkyl or amino; or $R_1$ is pyridyl; pyridyl substituted by at least one member selected from the group consisting of $C_{1-6}$ alkyls and halogens; trifluoromethyl; benzoyl or benzyl;

$R_2$ is H; phenyl; OH; $C_{1-3}$ alkyl; or $C_{1-3}$ alkoxy;

$R_3$ and $R_4$ are each, independently of each other, H; $C_{1-6}$ alkyl; OH; $C_{1-6}$ alkoxy; or halogen;

$R_5$ is H; $C_{1-3}$ alkyl; CN; or $COOR_{10}$ $R_6$ is H; $C_{1-6}$ alkyl; OH; —($C_{1-3}$ alkylene)—CN; $COOR_{10}$; —O—CO—($C_{1-6}$ alkyl);

or $R_5$ and $R_6$ together are a group $=CR_{10}R_{11}$, or a group =NOH, or a group =O or a group $=CHR_{12}$, where $R_{12}$ is phenyl, pyridyl, phenyl substituted by at least one member selected from the group consisting of halogen atoms, trifluoromethyl and $C_{1-3}$ alkyls or pyridyl substituted by at least one member selected from the group consisting of halogen atoms, trifluoromethyl and $C_{1-3}$ alkyls;

$R_7$ is H; CHO; $COOR_{10}$; $CH_2HC_2COOR_{10}$; —CH=CH—$COOR_{10}$; —P(O)($OR_{10}R_{11}$)$_2$; $NR_{13}R_{14}$ (where $R_{13}$ and $R_{14}$ are independently H; phenyl; phenyl substituted by a halogen atom or a $C_{1-3}$ alkyl group or a group —$COOR_{10}$, —CO—O—CH($CH_3$)—$COOR_{10}$, morpholinyl, —C($CH_2OH$)$_2$($CH_3$), imidazolinyl, —($C_{1-6}$ alkylene)—OH, —($C_{1-6}$ alkylene)—$COOR_{10}$, or $C_{1-3}$ alkoxy, or wherein $R_{13}$ and $R_{14}$ together with the nitrogen atom to which they are both bound form an imidazole or a N—($C_{1-3}$ alkyl)piperazinyl, or $R_7$ is —CO—($C_{1-6}$ alkyl); —S—($C_{1-6}$ alkyl); —SH; —S—CO—($C_{1-3}$ alkyl); —S—($CH_2$)$_m$$COOR_{10}$ (with $0<m\leqq 6$); —CO—O—($C_{1-6}$ alkylene)—$NR_{10}$ $R_{11}$; —O—($C_{1-6}$ alkylene—$NR_{10}R_{11}$; —$NR_{10}NR_{10}R_{11}$; $C_{1-6}$ alkyl; —$CONR_{10}R_{11}$; —$CSNR_{10}R_{11}$; thiazolyl; thiazolyl substituted by at least one member selected from the group consistin of —$NH_2$, $C_{1-3}$ alkyl, phenyl, and $COOR_{10}$; —NH—CO—($C_{1-3}$-alkyl); or —($C_{1-3}$-alkylene)—CH($NH_2$(COOH); or —$CR_5R_6R_7$ is a group of one of the formulae

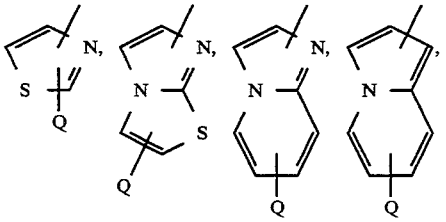

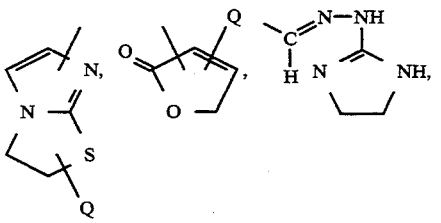

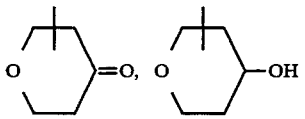

wherein Q is at least one member selected from the group consisting of H; $COOR_{10}$; phenyl; —O—($C_{1-3}$-alkylene)—$COOR_{10}$; $C_{1-3}$ alkyl; —O—C—S—$NR_{10}R_{11}$; —O—($C_{1-3}$-alkylene)—$NR_{10}R_{11}$; OH; $C_{1-3}$ alkoxy; and $NR_{10}R_{11}$; or wherein any two of $R_3$, $R_4$, $R_5$, $R_6$ and $R_7$ together —($C_{1-3}$—alkylene)—$COOR_{10}$; —($C_{1-3}$-alkyl)—OH, $COOR_{10}$, or —($C_{1-3}$-form a benzene ring; or a benzene ring substituted by alkylene)—O—CO—($C_{1-3}$-alkyl); or a naphthalene system; or a naphthalene system substituted by —($C_{1-3}$-alkylene)—$COOR_{10}$, —($C_{1-3}$-alky)—OH, $COOR_{10}$, or —($C_{1-3}$-alkylene)—O—CO—($C_{1-3}$-alkyl); and physiologically acceptable salts thereof, with the proviso that when —$CR_5R_6R_7$ is situated at the 8-position of formula (I) and X is O, (i) when $R_2$, $R_3$, $R_4$, $R_5$ and $R_6$ are all H and $R_7$ is CN, $R_1$ is other than phenyl, 2-thenyl, 3,4-dimethoxy phenyl, 3-methoxy phenyl, para-tolyl, 2-furyl, 2-naphthyl, 4-methoxy phenyl, benzyl, methyl, or cyclohexyl;

(ii) when $R_2$, $R_3$, $R_4$, $R_5$ and $R_6$ are all H and $R_7$ is COOH, $R_1$ is other than phenyl, 2-thenyl, 3-methoxy phenyl, 3,4-dimethoxy phenyl, 2-furyl, para-tolyl, 2-naphthyl, 4-methoxy phenyl, cyclohexyl, benzyl, or methyl;

(iii) when $R_2$, $R_3$, $R_4$, $R_5$ and $R_6$ are all H and $R_7$ is —CO—O—$CH_2CH_2$—N($C_2H_5$)$_2$, $R_1$ is other than phenyl, 2-thenyl, para-tolyl, or 4-methoxy phenyl;

(iv) when $R_2$, $R_3$, $R_4$, $R_5$ and $R_6$ are all H and $R_7$ is

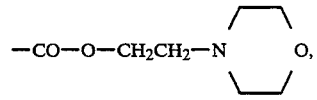

$R_1$ is other than phenyl;

(v) when $R_2$, $R_3$, $R_4$, $R_5$ and $R_6$ are all H and $R_7$ is —CO—O—($CH_2$)$_3$N($CH_3$)$_2$, $R_7$ is other than phenyl;

(vi) when $R_2$, $R_3$, $R_4$, $R_5$ and $R_6$ are all H and $R_7$ is —CO—O—$C_2H_5$, $R_1$ is other than phenyl;

(vii) when $R_2$, $R_3$, $R_4$, $R_5$ and $R_6$ are all H and $R_7$ is —CO—O—$CH_3$, $R_1$ is other than phenyl or 2-thenyl;

(viii) when $R_2$, $R_3$, $R_4$, $R_5$ and $R_6$ are all H and $R_7$ is —CO—O—Na, $R_1$ is other than phenyl;

(ix) when $R_2$, $R_3$, $R_4$, $R_5$ and $R_6$ are all H and $R_7$ is —CO—O—$CH_2CH_2OH$, $R_1$ is other than phenyl;

(x) when $R_2$, $R_3$, $R_4$, $R_5$ and $R_6$ are all H and $R_7$ is —CO—NH—$CH_2CH_2N(C_2H_5)_2$, $R_1$ is other than phenyl;

(xi) when $R_2$, $R_4$, $R_5$ and $R_6$ are all H, $R_3$ is methyl at the 6-position of formula (I) (6-$CH_3$) and $R_7$ is COOH, $R_1$ is other than phenyl;

(xii) when $R_2$, $R_4$, $R_5$ and $R_6$ are all H, $R_3$ is 6-$CH_3$ and $R_7$ is $COOH_3$, $R_1$ is other than phenyl;

(xiii) when $R_2$, $R_4$, $R_5$ and $R_6$ are all H, $R_3$ is 6-$CH_3$ or 6-$OCH_3$ and $R_7$ is —CO—O—$CH_2CH_2$—N($CH_2H_5$)$_2$, $R_1$ is other than phenyl;

(xiv) when $R_2$ and $R_3$ are H, $R_4$ is H or 6-$CH_3$, $R_5$ is methyl, $R_6$ is —$COOC_2H_5$, and $R_7$ is —$COOC_2H_5$, $R_1$ is other than phenyl;

(xv) when $R_2$ and $R_3$ are H, $R_4$ is H or 6—$CH_3$, $R_5$ is H, $R_6$ is $CH_3$ and $R_7$ is COOH, $R_1$ is other than phenyl;

(xvi) when $R_2$, $R_3$, $R_4$ and $R_5$ are all H, $R_6$ is $CH_3$ and $R_7$ is —CO—O—$CH_2CH_2N(C_2H_5)_2$, $R_1$ is other than phenyl;

(xvii) when $R_2$, $R_3$, $R_4$ and $R_7$ are all H, $R_5$ and $R_6$ are =O, $R_1$ is other than phenyl;

(xviii) when $R_2$, $R_3$, $R_4$, and $R_5$ are all H and —$CR_5R_6R_7$ is —CH=CH—COOH, —CH=CH—$COOCH_2CH_2N(C_2H_5)_2$,

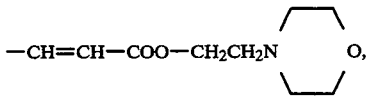

—$CH_2CH(COOC_2H_5)_2$, or —$CH_2CH_2COOH$, $R_1$ is other than phenyl;

(xix) when $R_2$ and $R_3$ are both H, $R_4$ is 6-$CH_3$ or 6-$OCH_3$, $R_6$ and $R_7$ are H and $R_5$ is CN, $R_1$ is other than phenyl; (xx) when $R_2$ and $R_3$ are H, $R_4$ is 6-$OCH_3$ or 6-OH, and $R_5$ and $R_6$ are H and $R_7$ is COOH, $R_1$ is other than phenyl;

(xxi) when $R_2$ is phenyl, $R_3$ and $R_4$ are H, $R_5$ and $R_6$ are =O, or $R_6$ is CN or COOH, $R_1$ is other than phenyl.

2. The method of claim 1, wherein $R_7$ is —CHO, —$COOR_{10}$, $P(O)(OR_{10}R_{11})_2$, —$CH_2CH_2COOR_{10}$ or —$CONR_{10}R_{11}$.

3. A method for treating cancer in a patient in need thereof, comprising coadministering to said patient an effective amount of (i) interleukin-2 or a protein having the in vivo activity of interleukin-2, and (ii) a flavonoid compound which is at least one member selected from the group consisting of

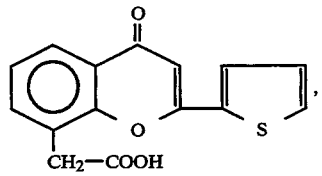

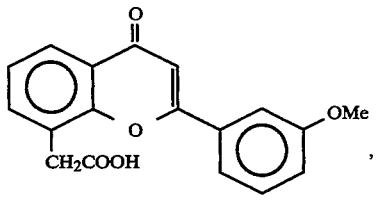

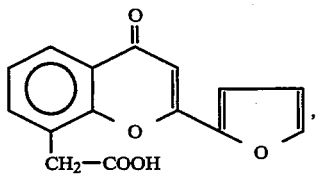

and

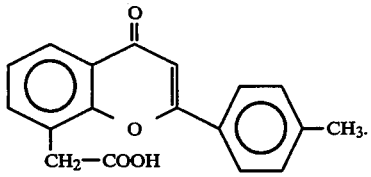

4. A method for treating cancer in a patient in need thereof, comprising coadministering to said patient an effective amount of (i) interleukin-2 or a protein having the in vivo activity of interleukin-2, and (ii) at least one flavonoid compound which has the immunolodulatory activity of (iia) boosting natural activity and (iib) inducing interferon, wherein said flavonoid compound belongs to the family of flavonoids of the formula (II):

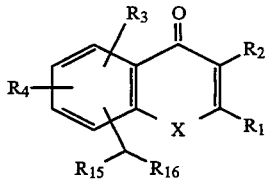

(II)

wherein:

X is N, O, Se, or $S(O)_n$, wherein n is 0, 1 or 2;

$R_1$ is methyl, phenyl, or substituted phenyl, biphenyl, or trifluoromethyl;

$R_2$ is hydrogen, OH; or $R_1$ and $R_2$ together form a naphthalene system fused to the flavonoid nucleus;

$R_3$ and $R_4$ are hydrogen, $C_{1-6}$-alkyl, $C_{1-6}$ alkoxyhydroxyl, halogen; or $R_3$ and $R_4$ together form a benzene system fused to the flavonoid nucleus;

$R_{15}$ is hydrogen when $R_{16}$ is a carboxylic radical, a carboamyl radical, a mercapto radical, a carboxymethythio radical, an aminoether radical, a phosphonic group, a substituted hydrazine group, an amino group, a substituted amino group, a lower alkyl group, a group —$CONHR_{17}$ or —$CSNHR_{18}$, where $R_{17}$ and $R_{18}$ are $C_{1-6}$ alkyl, an oximino group, a substituted thiazolyl group, or a group —$NR_{19}R_{20}$, where $R_{19}$ and $R_{20}$ are independently hydrogen, an aromatic group, a substituted aromatic group, a $C_{1-6}$ hydroxyalkyl group, a carboxymethylene group, or $R_{19}$ and $R_{20}$ together form imidazolyl or N-methylpiperazinyl; or when $R_{15}$ is R—CH=, $R_1$ is hydrogen, phenyl, 3-pyridyl or 4-pyridyl and $R_{16}$ is COOH; or $R_{15}$ and $R_{16}$ together are a tetronic moiety substituted tetronic moiety of the formula:

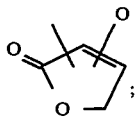

when $R_{16}$ is =O, $R_{15}$ is COOH, —CHCOOH, —$CH_3$, —$CH_3$, —$CH_2Br$ or —CH=CHAr, with Ar being H, phenyl, 3-pyridyl or 4-pyridyl; or $R_{15}$ and $R_{16}$ together are indolizinyl, imidazo[2,1-b]thiazolyl, imidazo[1,2-a]pyridino, tetrahydropyrane which is substituted or a cyclic lactonic moiety; or when $R_4$ and $R_{15}$ together form a benzene system, $R_{16}$ is —COOH or —$CH_2COOH$; or when $R_1$ and $R_2$ together form a naphthalene system, $R_{15}$ is H and $R_{16}$ is —COOH; or when $R_3$ and $R_4$ form a benzene system, $R_{15}$ is H and $R_{16}$ COOH; or when $R_{15}$ hydroxyl, $R_{16}$ is —COOH or —$CH_2CH_2COOH$; or when $R_{15}$ is =O, $R_{16}$ is —COOh, —$CH_2CH_2COOH$ or —CH=CHCOOH.

5. A method for treating cancer in a patient in need thereof, comprising coadministering to said patient an effective amount of (i) interleukin-2 or a protein having the in vivo acitivity of interleukin-2, and (ii) at least one flavonoid compound which as the immunomodulatory activity of (iia) boosting natural activity and (iib) inducing interferon, wherein said flavonoid compound belongs to the family of flavonoinds of the formula (IV):

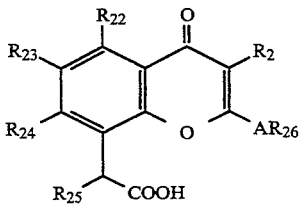

(IV)

wherein:

$AR_{26}$ is phenyl, substituted phenyl, biphenyl, pyridyl, or trifluoromethyl $R_2$ is hydrogen, hydroxyl, or $C_{1-3}$ alkoxy;

$R_{22}$ is hydrogen, hydroxyl, or $C_{1-6}$ alkoxy;

$R_{23}$ is hydrogen or fluoro;

$R_{24}$ is hydrogen or hydroxy;

$R_{25}$ is hydrogen, 2-methylpyridyl, benzylidene, 4-methylenepyridyl or methylene; or $R_{22}$ and $R_{23}$ together form a benzene ring fused to the flavonoid nucleus; or $R_{23}$ and $R_{24}$ together form a benzene ring fused to the flavonoid nucleus; or $R_{25}$ and $R_{24}$ together form a benzene ring fused to the flavonoid nucleus.

* * * * *